US011226290B2

(12) United States Patent
Rothberg et al.

(10) Patent No.: US 11,226,290 B2
(45) Date of Patent: Jan. 18, 2022

(54) PHOTONIC STRUCTURES AND INTEGRATED DEVICE FOR DETECTING AND ANALYZING MOLECULES

(71) Applicant: Quantum-Si Incorporated, Guilford, CT (US)

(72) Inventors: Jonathan M. Rothberg, Guilford, CT (US); Ali Kabiri, Madison, CT (US); Gerard Schmid, Guilford, CT (US); Keith G. Fife, Palo Alto, CA (US); James Beach, Austin, TX (US); Jason W. Sickler, Madison, CT (US); Lawrence C. West, San Jose, CA (US); Paul E. Glenn, Wellesley, MA (US); Kyle Preston, Guilford, CT (US); Farshid Ghasemi, Guilford, CT (US); Benjamin Cipriany, Branford, CT (US); Jeremy Lackey, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 862 days.

(21) Appl. No.: 15/611,583

(22) Filed: Jun. 1, 2017

(65) Prior Publication Data

US 2017/0350818 A1    Dec. 7, 2017

Related U.S. Application Data

(60) Provisional application No. 62/344,123, filed on Jun. 1, 2016.

(51) Int. Cl.
*G01N 21/64* (2006.01)
*C12Q 1/68* (2018.01)
(Continued)

(52) U.S. Cl.
CPC ....... *G01N 21/6428* (2013.01); *C12Q 1/6869* (2013.01); *C12Q 1/6874* (2013.01);
(Continued)

(58) Field of Classification Search
CPC .............. G01N 21/6428; G01N 21/64; G01N 21/6454; G01N 21/6452; G01N 21/645;
(Continued)

(56) References Cited

U.S. PATENT DOCUMENTS

| 5,961,924 A | 10/1999 | Reichert et al. |
| 6,787,308 B2 | 9/2004 | Balasubramanian et al. |

(Continued)

FOREIGN PATENT DOCUMENTS

| CN | 101960293 A | 1/2011 |
| CN | 102066997 A | 5/2011 |

(Continued)

OTHER PUBLICATIONS

Invitation to Pay Additional Fees for International Application No. PCT/US2017/035412 dated Sep. 8, 2017.
(Continued)

*Primary Examiner* — John R Lee
(74) *Attorney, Agent, or Firm* — Wolf, Greenfield & Sacks, P.C.

(57) ABSTRACT

System and methods for analyzing single molecules and performing nucleic acid sequencing. An integrated device may include multiple pixels with sample wells configured to receive a sample, which when excited, emits radiation. The integrated device includes a surface having a trench region recessed from a portion of the surface and an array of sample wells, disposed in the trench region. The integrated device also includes a waveguide configured to couple excitation energy to at least one sample well in the array and positioned at a first distance from a surface of the trench region and at
(Continued)

a second distance from the surface in a region separate from the trench region. The first distance is smaller than the second distance. The system also includes an instrument that interfaces with the integrated device. The instrument may include an excitation energy source for providing excitation energy to the integrated device by coupling to an excitation energy coupling region of the integrated device.

20 Claims, 53 Drawing Sheets

(51) Int. Cl.
  G01N 21/77    (2006.01)
  G01N 33/543   (2006.01)
  C12Q 1/6869   (2018.01)
  C12Q 1/6874   (2018.01)
(52) U.S. Cl.
  CPC ....... *G01N 21/648* (2013.01); *G01N 21/6408* (2013.01); *G01N 21/6454* (2013.01); *G01N 21/6486* (2013.01); *G01N 21/7743* (2013.01); *G01N 33/54373* (2013.01); *G01N 2021/6419* (2013.01); *G01N 2021/6421* (2013.01)
(58) Field of Classification Search
  CPC ... G01N 2021/6463; G01N 2021/6482; G01N 2021/6484; G01N 2021/6419; G01N 2021/6421; G01N 2021/6417; G01N 21/648; G01N 21/6486; G01N 21/7743; G01N 33/54373; C12Q 1/6874; C12Q 1/68; C12Q 1/6879
  See application file for complete search history.

(56) References Cited

U.S. PATENT DOCUMENTS

| | | |
|---|---|---|
| 6,917,726 B2 | 7/2005 | Levene et al. |
| 7,175,811 B2 | 2/2007 | Bach et al. |
| 7,426,322 B2 | 9/2008 | Hyde |
| 7,738,086 B2 | 6/2010 | Shepard et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 8,053,742 B2 | 11/2011 | Lundquist et al. |
| 8,207,509 B2 | 6/2012 | Lundquist et al. |
| 8,274,040 B2 | 9/2012 | Zhong et al. |
| 8,278,728 B2 | 10/2012 | Murshid |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,502,169 B2 | 8/2013 | Rigneault et al. |
| 8,618,507 B1 | 12/2013 | Lundquist et al. |
| 9,029,802 B2 | 5/2015 | Lundquist et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,060 B2 | 3/2017 | Chen et al. |
| 9,617,594 B2* | 4/2017 | Rothberg ............ H01S 3/0941 |
| 9,658,161 B2 | 5/2017 | Saxena et al. |
| 9,666,748 B2 | 5/2017 | Leobandung |
| 9,678,012 B2* | 6/2017 | Rothberg ............ C12Q 1/6869 |
| 9,719,138 B2 | 8/2017 | Zhong et al. |
| 9,765,395 B2 | 9/2017 | Goldsmith |
| 9,784,679 B2* | 10/2017 | Rothberg ........... G01N 21/6428 |
| 9,863,880 B2* | 1/2018 | Rothberg ........... G01N 21/7743 |
| 9,885,657 B2* | 2/2018 | Rothberg ........... G01N 21/6428 |
| 9,921,157 B2* | 3/2018 | Rothberg ........... G01N 21/6452 |
| 9,946,017 B2 | 4/2018 | Saxena et al. |
| 9,983,135 B2* | 5/2018 | Rothberg ............ C12Q 1/6874 |
| 10,018,764 B2 | 7/2018 | Grot et al. |
| 10,048,208 B2* | 8/2018 | Rothberg ............ C12Q 1/6874 |
| 10,090,429 B2 | 10/2018 | Leobandung |
| 10,138,515 B2 | 11/2018 | Fehr et al. |
| 10,246,742 B2* | 4/2019 | Rothberg ............ H01S 3/1118 |
| 10,280,457 B2 | 5/2019 | Zhong et al. |
| 10,288,565 B2* | 5/2019 | Rothberg ............ C12Q 1/6874 |
| 10,288,566 B2* | 5/2019 | Rothberg ............ G01N 21/648 |
| 10,310,178 B2 | 6/2019 | Saxena et al. |
| 10,371,634 B2* | 8/2019 | Rothberg ........... G01N 21/6408 |
| 10,487,356 B2 | 11/2019 | Lundquist et al. |
| 10,502,684 B2* | 12/2019 | Rothberg ........... G01N 21/6454 |
| 10,551,624 B2* | 2/2020 | Rothberg ........... G02B 27/0966 |
| 10,578,788 B2 | 3/2020 | Grot et al. |
| 10,655,172 B2 | 5/2020 | Rank et al. |
| 10,724,090 B2 | 7/2020 | McCaffrey et al. |
| 2002/0182716 A1 | 12/2002 | Weisbuch et al. |
| 2003/0174992 A1 | 9/2003 | Levene et al. |
| 2008/0081769 A1* | 4/2008 | Hassibi ................ C40B 30/04 506/9 |
| 2008/0212102 A1* | 9/2008 | Nuzzo ................ G01N 21/554 356/445 |
| 2008/0220509 A1* | 9/2008 | Segawa ..................... B01L 7/00 435/287.2 |
| 2009/0111207 A1* | 4/2009 | Choumane ......... G01N 21/6454 438/70 |
| 2009/0146076 A1* | 6/2009 | Chiou .................. C12Q 1/6804 250/458.1 |
| 2009/0303475 A1* | 12/2009 | Jayaraman ................ G01J 3/02 356/320 |
| 2010/0065726 A1 | 3/2010 | Zhong et al. |
| 2012/0014837 A1* | 1/2012 | Fehr ...................... G01N 21/05 422/82.11 |
| 2013/0116153 A1 | 5/2013 | Bowen et al. |
| 2013/0338013 A1* | 12/2013 | Zhong ...................... C12Q 1/68 506/3 |
| 2014/0199016 A1* | 7/2014 | Grot .................... G01N 21/6486 385/11 |
| 2015/0141267 A1 | 5/2015 | Rothberg et al. |
| 2015/0141268 A1* | 5/2015 | Rothberg ........... G01N 21/6452 506/2 |
| 2015/0177150 A1* | 6/2015 | Rothberg ........... G01N 21/6486 506/2 |
| 2015/0268160 A1 | 9/2015 | Liu et al. |
| 2015/0309261 A1* | 10/2015 | Kobyakov ............. G02B 6/305 385/14 |
| 2015/0376694 A1* | 12/2015 | McCaffrey ........... G01N 21/645 506/2 |
| 2016/0041095 A1* | 2/2016 | Rothberg ............. G01N 21/648 506/4 |
| 2016/0047749 A1* | 2/2016 | Lee ......................... H01L 31/18 422/82.08 |
| 2016/0061740 A1* | 3/2016 | Grot .................... G02B 27/4238 506/16 |
| 2016/0084761 A1 | 3/2016 | Rothberg et al. |
| 2016/0178568 A1* | 6/2016 | Cheng ................. G01N 27/4145 257/253 |
| 2016/0211390 A1* | 7/2016 | Chen .................... G01N 21/7703 |
| 2017/0016851 A1* | 1/2017 | Cheng ................. G01N 27/4145 |
| 2017/0067829 A1* | 3/2017 | Duer .................... G01N 21/648 |
| 2017/0102530 A1* | 4/2017 | Chang ................. G01N 21/6452 |
| 2017/0146479 A1 | 5/2017 | Levine et al. |
| 2017/0349944 A1* | 12/2017 | Rothberg .............. G16B 30/00 |
| 2017/0350818 A1* | 12/2017 | Rothberg ............. C12Q 1/6869 |
| 2018/0088052 A1* | 3/2018 | Rothberg ............. G01N 21/645 |
| 2018/0172906 A1* | 6/2018 | Rothberg ............. G01N 21/253 |
| 2018/0173000 A1* | 6/2018 | Rothberg ........... G02B 27/0944 |
| 2018/0239087 A1* | 8/2018 | Saxena ................. B29D 17/007 |
| 2019/0256911 A1* | 8/2019 | Lundquist .......... G01N 21/6428 |
| 2019/0292590 A1* | 9/2019 | Zhong ................. C12Q 1/6874 |
| 2020/0003613 A1* | 1/2020 | Brueck ................. H01L 31/103 |

FOREIGN PATENT DOCUMENTS

| | | |
|---|---|---|
| CN | 102077124 A | 5/2011 |
| CN | 103001120 A | 12/2012 |
| CN | 105209883 A | 12/2015 |

(56) References Cited

FOREIGN PATENT DOCUMENTS

| EP | 1773011 A2 | 4/2007 |
| JP | 2016-65878 A | 4/2016 |
| JP | 2017-537850 A | 12/2017 |
| WO | WO 2011/153962 | 12/2011 |
| WO | WO 2014/031157 A1 | 2/2014 |

OTHER PUBLICATIONS

International Search Report and Written Opinion for International Application No. PCT/US2017/035412 dated Nov. 7, 2017.
Hale, Fibre Optic Sensors using Adiabatically Tapered Single Mode Fibres. Dissertation submitted to the University of Cambridge. Feb. 1994. 209 pages.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Taitt et al., Evanescent wave fluorescence biosensors. Biosens Bioelectron. Jun. 2005;20(12):2470-87. Epub Dec. 8, 2004.

\* cited by examiner

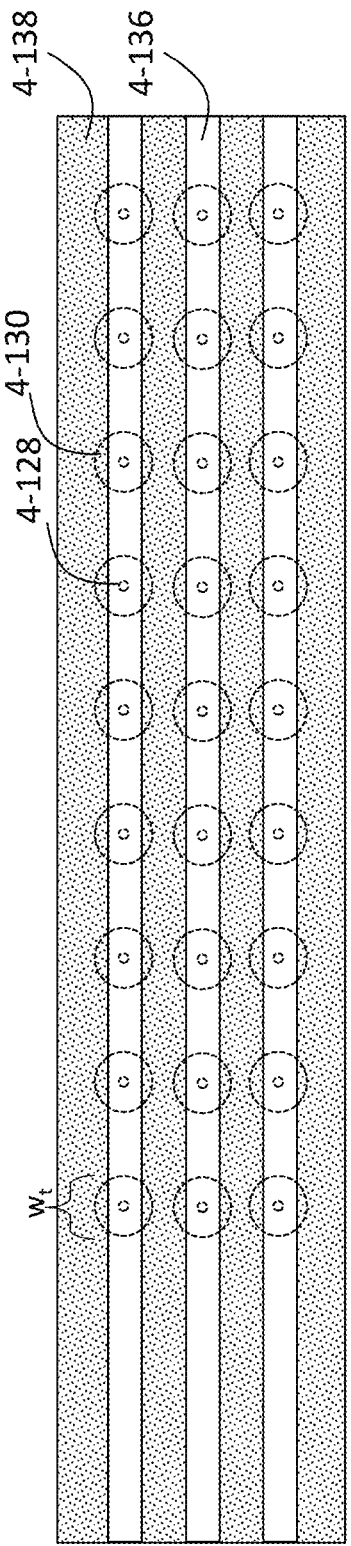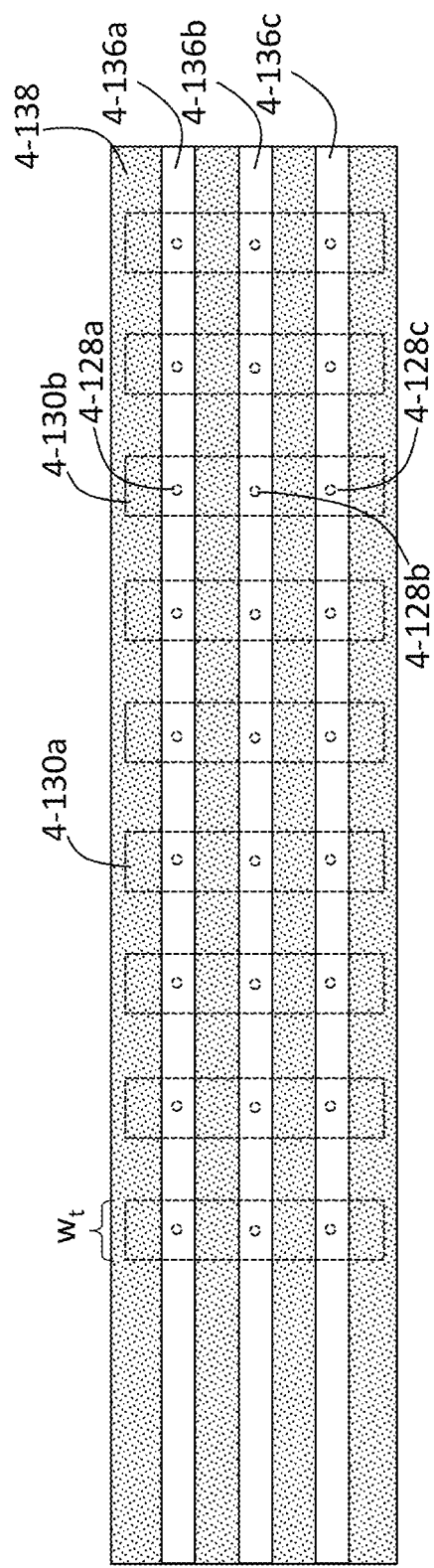
FIG 4-1C
FIG 4-1D

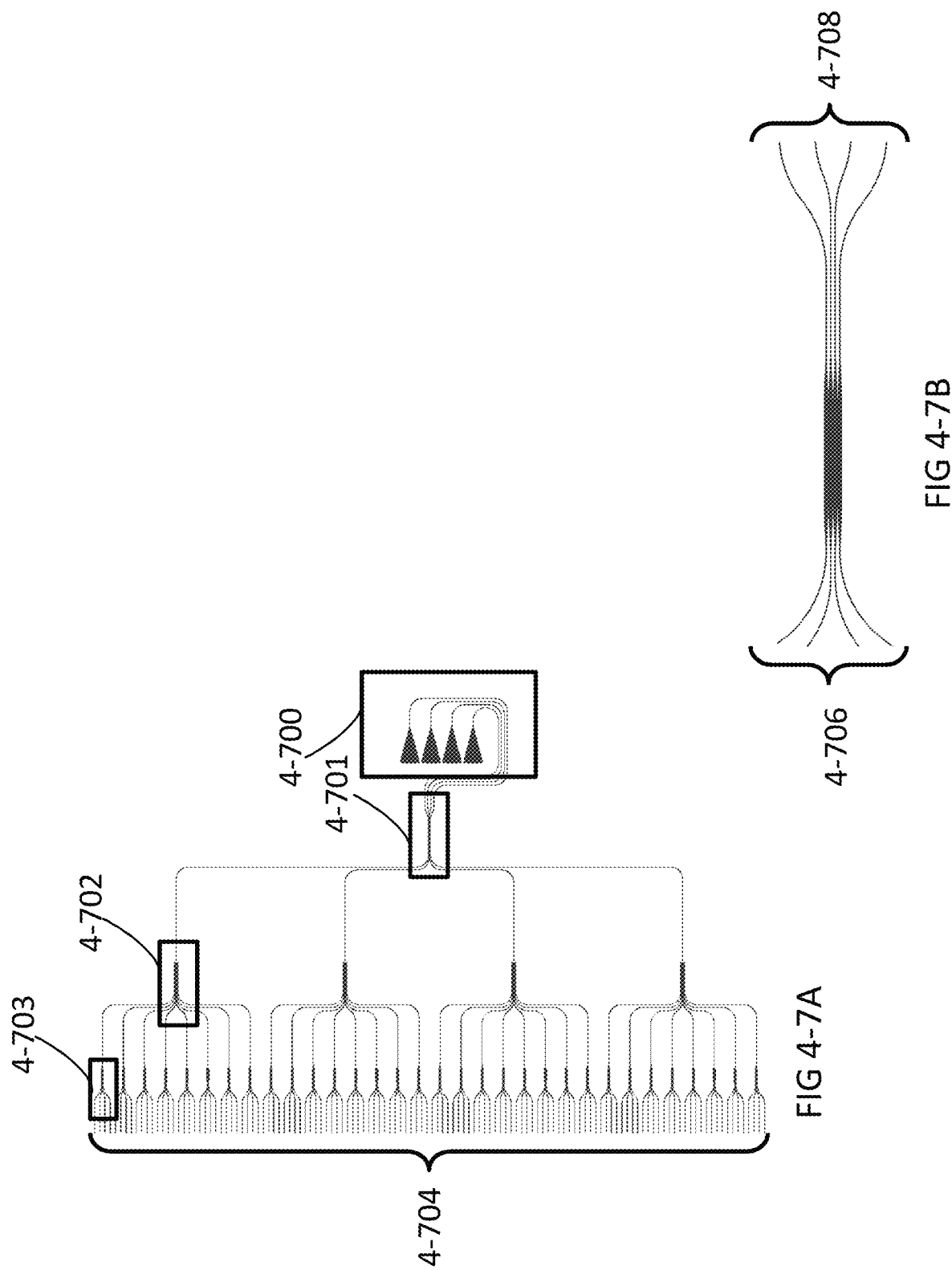

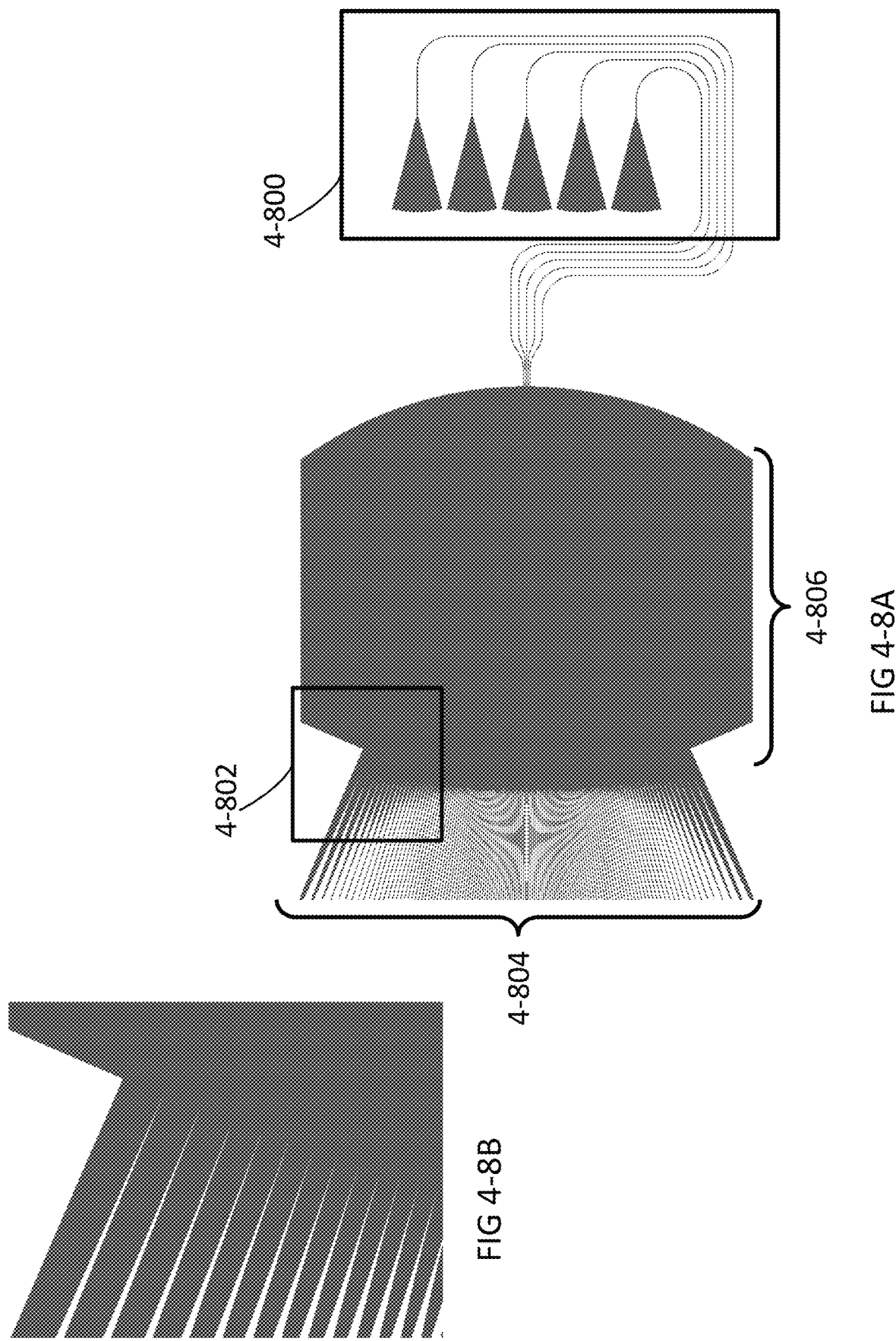

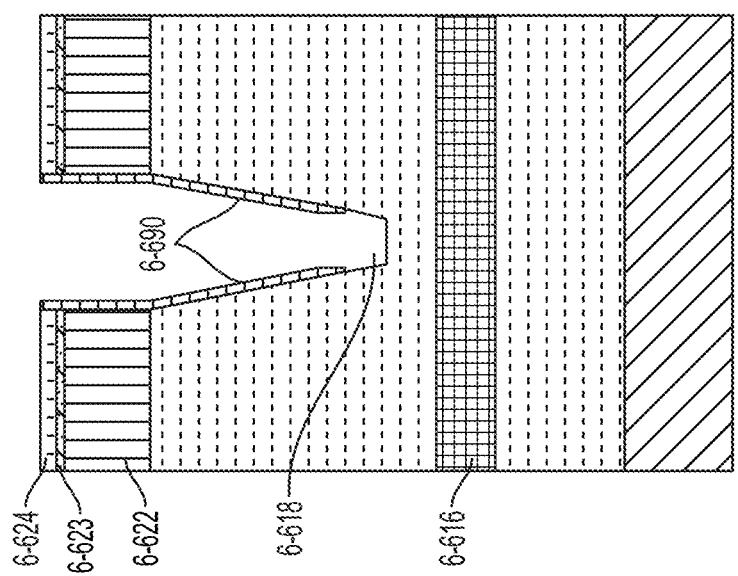

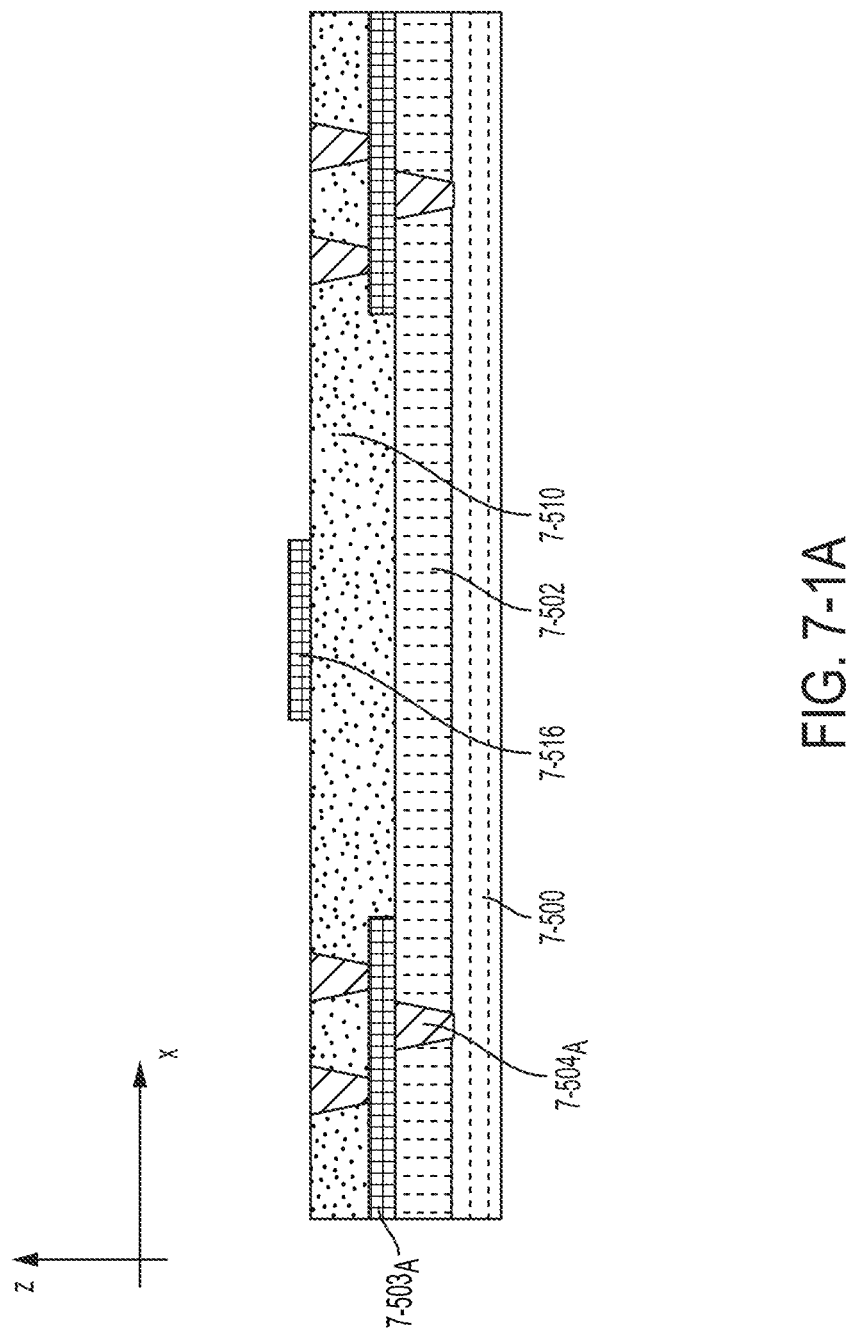

PHOTONIC STRUCTURES AND INTEGRATED DEVICE FOR DETECTING AND ANALYZING MOLECULES

RELATED APPLICATIONS

This application claims priority to U.S. Provisional Patent Application 62/344,123, titled "PHOTONIC STRUCTURES AND INTEGRATED DEVICE FOR DETECTING AND ANALYZING MOLECULES," filed Jun. 1, 2016, which is hereby incorporated by reference in its entirety.

FIELD OF THE APPLICATION

The present application is directed generally to devices, methods and techniques for performing rapid, massively parallel, quantitative analysis of biological and/or chemical samples, and methods of fabricating said devices.

BACKGROUND

Detection and analysis of biological samples may be performed using biological assays ("bioassays"). Bioassays conventionally involve large, expensive laboratory equipment requiring research scientists trained to operate the equipment and perform the bioassays. Moreover, bioassays are conventionally performed in bulk such that a large amount of a particular type of sample is necessary for detection and quantitation.

Some bioassays are performed by tagging samples with luminescent markers that emit light of a particular wavelength. The markers are illuminated with a light source to cause luminescence, and the luminescent light is detected with a photodetector to quantify the amount of luminescent light emitted by the markers. Bioassays using luminescent markers conventionally involve expensive laser light sources to illuminate samples and complicated luminescent detection optics and electronics to collect the luminescence from the illuminated samples.

SUMMARY

Some embodiments relate to an integrated device that includes a surface having a trench region recessed from a portion of the surface and an array of sample wells, disposed in the trench region. A sample well of the array of sample wells may be configured to receive a sample. The integrated device further includes a waveguide configured to couple excitation energy to at least one sample well in the array and positioned at a first distance from a surface of the trench region and at a second distance from the surface in a region separate from the trench region. The first distance may be smaller than the second distance.

The first distance may be between 150 nm and 600 nm. The second distance may be between 250 nm and 2000 nm. The sample well may have a surface at a distance less than 300 nm from the waveguide. The integrated device may further include at least one grating coupler configured to receive excitation energy from an excitation source separate from the integrated device and to direct excitation energy to the waveguide. The integrated device may further include a reflector configured to reflect excitation energy towards the at least one grating coupler.

The integrated device may further include a splitter structure configured to receive excitation energy from the at least one grating coupler and direct excitation energy to a plurality of waveguides. The splitter structure may include at least one multi-mode interference splitter. The splitter structure may include a star coupler. The splitter structure may include a sliced grating coupler.

The waveguide may have a tapered dimension in a direction perpendicular to the direction of light propagation along the waveguide such that the dimension is larger at a location proximate to the grating coupler than at a distal location. The sample well may include a sidewall spacer formed on at least a portion of a sidewall of the sample well. A surface of the sample well proximate to the waveguide may be configured to interact with the sample in a different manner than the sidewall spacer.

The integrated device further include a metal stack formed on a bottom surface of the trench region, such that the metal stack has an opening that overlaps with an aperture of a sample well of the array. The metal stack may include an aluminum layer and a titanium nitride layer, and the aluminum layer is proximate to the waveguide. The waveguide may include silicon nitride. The integrated device may further include a sensor configured to receive emission energy emitted by the sample located in the sample well.

Some embodiments relate to an integrated device that includes a substrate, a waveguide having a first side facing the substrate and a second side opposite the first side, and a plurality of metal layers configured to support a plurality of electrical signals. A first metal layer of the plurality of metal layers may be positioned at a distance closer to the substrate than the first side of the waveguide.

The waveguide may be positioned at a distance closer to the substrate than a second metal layer of the plurality of metal layers.

The integrated device may further include a surface having a trench region recessed from a portion of the surface and an array of sample wells, disposed in the trench region. A sample well of the array of sample wells may be configured to receive a sample. The waveguide may be positioned at a first distance from a surface of the trench region and at a second distance from the surface in a region separate from the trench region. The first distance may be smaller than the second distance.

Some embodiments relate to a method of forming an integrated device that includes forming an waveguide over a substrate, forming a top cladding over the waveguide, forming a trench region in the top cladding, forming a metal stack on a surface of the top cladding, and forming at least one sample well at a surface of the trench region proximate to the waveguide.

The method may further include planarizing the top cladding to a distance from a surface of the top cladding to the waveguide. The distance between a surface of top cladding to the waveguide at a location within the trench region may be between 150 nm and 600 nm. Forming the at least one sample well may include selectively etching the metal layer to form openings that extend to the top cladding layer. Selectively etching the metal layer may include selectively etching the metal layer using a photoresist mask and selectively etching the top cladding using a photoresist mask or a hard mask. Forming the at least one sample well may include performing a timed etch of the top cladding. Forming the at least one sample well may include forming at least one etch stop layer on the top cladding, forming a dielectric layer over the top cladding and the etch stop layer, and removing the dielectric layer at locations that overlap with the at least one etch stop layer to expose the etch stop layer. The method may further include forming a spacer on at least a portion of a sidewall of a sample well of the at least one sample well. Forming the spacer may be performed with an atomic layer deposition (ALD) process. Forming the spacer may include etching the spacer from a surface of the sample well proximate the waveguide.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 1-2A is a plot of exemplary emission timing spectra.

FIG. 1-2B is a plot exemplary absorption wavelength spectra.

FIG. 1-2C is a plot of exemplary emission wavelength spectra.

FIG. 1-3A is a phase space diagram for emission wavelength and emission lifetime.

FIG. 1-3B is a phase space diagram for absorption wavelength and emission lifetime.

FIG. 1-4 is a phase space diagram for emission wavelength, absorption wavelength, and emission lifetime.

FIG. 2-A is a block diagram representation of an apparatus that may be used for rapid, mobile analysis of biological and chemical specimens, in accordance with some embodiments.

FIG. 2-1B is a block diagram of an integrated device and an instrument, in accordance with some embodiments.

FIG. 3-1A is a schematic of an integrated device, in accordance with some embodiments.

FIG. 3-1B is a schematic of excitation energy coupling to sample wells in a row of pixels and emission energy from each sample well directed towards sensors, in accordance with some embodiments.

FIG. 3-2A is a planar view of optical components of an integrated device, in accordance with some embodiments.

FIG. 3-2B is a planar view of optical components of an integrated device, in accordance with some embodiments.

FIG. 3-2C is a planar view of a test structure, in accordance with some embodiments.

FIG. 3-2D is a plot of relative power as a function of length obtained from measurements performed by the test structure shown in FIG. 3-2C.

FIG. 4-1A is a cross-sectional view of an integrated device having a plurality of sample wells, in accordance with some embodiments.

FIG. 4-1B is a cross-sectional view of an integrated device having a plurality of trench regions, in accordance with some embodiments.

FIG. 4-1C is a planar view of an integrated device having circular trench regions associated with individual sample wells, in accordance with some embodiments.

FIG. 4-1D is a planar view of an integrated device having rectangular trench regions that overlap with multiple waveguides, in accordance with some embodiments.

FIG. 4-2 is a cross-sectional view of an integrated device having a plurality of metal layers, in accordance with some embodiments.

FIG. 4-3 is a cross-sectional view of a pixel of an integrated device, in accordance with some embodiments.

FIG. 4-4 is a planar view of a grating coupler, in accordance with some embodiments.

FIG. 4-5 is a heat map illustrating a grating coupler's coupling efficiency as a function of the thickness of a top cladding and a bottom cladding, in accordance with some embodiments.

FIG. 4-6 is a planar view of a cascaded MMI splitter structure, in accordance with some embodiments.

FIG. 4-7A is a planar view of a cascaded MMI splitter structure, in accordance with some embodiments.

FIG. 4-7B is a planar view of an exemplary MMI, in accordance with some embodiments.

FIG. 4-7C is a planar view of an exemplary MMI, in accordance with some embodiments.

FIG. 4-8A is a planar view of an exemplary star coupler splitter structure, in accordance with some embodiments.

FIG. 4-8B is a planar view of region 4-802 of the star coupler splitter structure of FIG. 4-8A.

FIG. 4-9A is a planar view of an exemplary star coupler splitter structure, in accordance with some embodiments.

FIG. 4-9B is a planar view of region 4-900 of the star coupler splitter structure of FIG. 4-9A.

FIG. 4-9C is a planar view of region 4-902 of the star coupler splitter structure of FIG. 4-9A.

FIG. 4-10 is a planar view of an exemplary star coupler splitter structure, in accordance with some embodiments.

FIG. 4-11 is a planar view of a sliced grating coupler splitter structure, in accordance with some embodiments.

FIGS. 5-1A to 5-1C illustrate a fabrication sequence for fabricating an integrated device comprising a trench region, in accordance with some embodiments.

FIGS. 5-2A to 5-2F illustrate a fabrication sequence for fabricating an integrated device comprising a plurality of sample wells, in accordance with some embodiments.

FIGS. 5-3A to 5-3G illustrate a fabrication sequence for fabricating an integrated device comprising a plurality of sample wells, in accordance with some embodiments.

FIGS. 6-1A to 6-1F illustrate a fabrication sequence for fabricating a sample well, in accordance with some embodiments.

FIGS. 7-1A to 7-1E illustrate a fabrication sequence for fabricating an integrated device comprising a plurality of metal layers, in accordance with some embodiments.

FIGS. 7-2A and 7-2B illustrate a fabrication sequence for fabricating an integrated device comprising a plurality of metal layers, in accordance with some embodiments.

DETAILED DESCRIPTION

Figure 1:
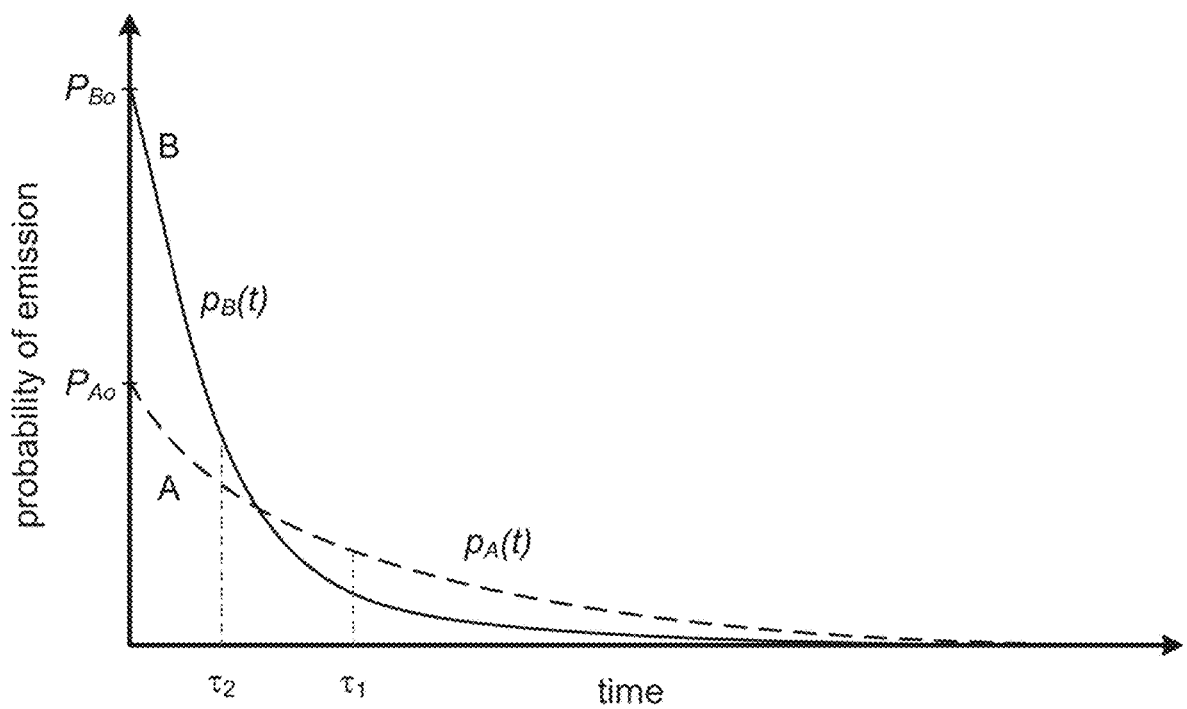
FIG. 1-1 is a plot of probability for emitting a photon from a marker as a function of time.

The inventors have recognized and appreciated that a compact, high-speed apparatus for performing detection and quantitation of single molecules or particles could reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, access to essential diagnostic tests that could dramatically improve their health and well-being. For example, embodiments described herein may be used for diagnostic tests of blood, urine and/or saliva that may be used by individuals in their home, or by a doctor in a remote clinic in a developing country.

A pixelated sensor device with a large number of pixels (e.g., hundreds, thousands, millions or more) allows for the detection of a plurality of individual molecules or particles in parallel. The molecules may be, by way of example and not limitation, proteins and/or DNA. Moreover, a high-speed device that can acquire data at more than one hundred frames per second allows for the detection and analysis of dynamic processes or changes that occur over time within the sample being analyzed.

The inventors have recognized and appreciated that one hurdle preventing bioassay equipment from being made more compact was the need to filter the excitation light from causing undesirable detection events at the sensor. Optical filters used to transmit the desired signal light (the luminescence) and sufficiently block the excitation light can be thick, bulky, expensive, and intolerant to variations in the incidence angle of light, preventing miniaturization. The inventors, however, recognized and appreciated that using a pulsed excitation source can reduce the need for such as filtering or, in some cases, remove the need for such filters altogether. By using sensors capable of determining the time a photon is detected relative to the excitation light pulse, the signal light can be separated from the excitation light based on the time that the photon is received, rather than the spectrum of the light received. Accordingly, the need for a bulky optical filter is reduced and/or removed in some embodiments.

The inventors have recognized and appreciated that luminescence lifetime measurements may also be used to identify the molecules present in a sample. An optical sensor capable of detecting when a photon is detected is capable of measuring, using the statistics gathered from many events, the luminescence lifetime of the molecule being excited by the excitation light. In some embodiments, the luminescence lifetime measurement may be made in addition to a spectral measurement of the luminescence. Alternatively, a spectral measurement of the luminescence may be completely omitted in identifying the sample molecule. Luminescence lifetime measurements may be made with a pulsed excitation source. Additionally, luminescence lifetime measurements may be made using an integrated device that includes the sensor, or a device where the light source is located in a system separate from the integrated device.

The inventors have also recognized and appreciated that integrating a sample well (which may include a nanoaperture) and a sensor in a single integrated device capable of measuring luminescent light emitted from biological samples reduces the cost of producing such a device such that disposable bioanalytical integrated devices may be formed. Disposable, single-use integrated devices that interface with a base instrument may be used anywhere in the world, without the constraint of requiring high-cost biological laboratories for sample analyses. Thus, automated bioanalytics may be brought to regions of the world that previously could not perform quantitative analysis of biological samples. For example, blood tests for infants may be performed by placing a blood sample on a disposable integrated device, placing the disposable integrated device into a small, portable base instrument for analysis, and processing the results by a computer for immediate review by a user. The data may also be transmitted over a data network to a remote location to be analyzed, and/or archived for subsequent clinical analyses.

The inventors have also recognized and appreciated that a disposable, single-use device may be made more simply and for lower cost by not including the light source on the integrated device. Instead, the light source may include reusable components incorporated into a system that interfaces with the disposable integrated device to analyze a sample.

The inventors have also recognized and appreciated that, when a sample is tagged with a plurality of different types of luminescent markers, any suitable characteristic of luminescent markers may be used to identify the type of marker that is present in a particular pixel of the integrated device. For example, characteristics of the luminescence emitted by the markers and/or characteristics of the excitation absorption may be used to identify the markers. In some embodiments, the emission energy of the luminescence (which is directly related to the wavelength of the light) may be used to distinguish a first type of marker from a second type of marker. Additionally, or alternatively, luminescence lifetime measurements may also be used to identify the type of marker present at a particular pixel. In some embodiments, luminescence lifetime measurements may be made with a pulsed excitation source using a sensor capable of distinguishing a time when a photon is detected with sufficient resolution to obtain lifetime information. Additionally, or alternatively, the energy of the excitation light absorbed by the different types of markers may be used to identify the type of marker present at a particular pixel. For example, a first marker may absorb light of a first wavelength, but not equally absorb light of a second wavelength, while a second marker may absorb light of the second wavelength, but not equally absorb light of the first wavelength. In this way, when more than one excitation light source, each with a different excitation energy, may be used to illuminate the sample in an interleaved manner, the absorption energy of the markers can be used to identify which type of marker is present in a sample. Different markers may also have different luminescent intensities. Accordingly, the detected intensity of the luminescence may also be used to identify the type of marker present at a particular pixel.

One non-limiting example of an application of a device contemplated by the inventors is a device capable of performing sequencing of a biomolecule, such as a nucleic acid or a polypeptide (e.g. protein) having a plurality of amino acids. Diagnostic tests that may be performed using such a device include sequencing a nucleic acid molecule in a biological sample of a subject, such as sequencing of cell free deoxyribonucleic acid molecules or expression products in a biological sample of the subject.

The present application provides devices, systems and methods for detecting biomolecules or subunits thereof, such as nucleic acid molecules. Such detection can include sequencing. A biomolecule may be extracted from a biological sample obtained from a subject. The biological sample may be extracted from a bodily fluid or tissue of the subject, such as breath, saliva, urine or blood (e.g., whole blood or plasma). The subject may be suspected of having a health condition, such as a disease (e.g., cancer). In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30, 50, 100 base pairs (bp) or more) that can be used to identify a larger sequence or region, e.g., that can be aligned to a location on a chromosome or genomic region or gene.

Individual subunits of biomolecules may be identified using markers. In some examples, luminescent markers are used to identify individual subunits of biomolecules. Luminescent markers (also referred to herein as "markers") may be exogenous or endogenous markers. Exogenous markers may be external luminescent markers used in a reporter and/or tag for luminescent labeling. Examples of exogenous markers may include, but are not limited to, fluorescent molecules, fluorophores, fluorescent dyes, fluorescent stains, organic dyes, fluorescent proteins, enzymes, species that participate in fluorescence resonance energy transfer (FRET), enzymes, and/or quantum dots. Such exogenous markers may be conjugated to a probe or functional group (e.g., molecule, ion, and/or ligand) that specifically binds to a particular target or component. Attaching an exogenous marker to a probe allows identification of the target through detection of the presence of the exogenous marker. Examples of probes may include proteins, nucleic acid (e.g. DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may include mass tags or electrostatic tags.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

While some embodiments may be directed to diagnostic testing by detecting single molecules in a specimen, the inventors have also recognized that some embodiments may use the single molecule detection capabilities to perform nucleic acid (e.g. DNA, RNA) sequencing of one or more nucleic acid segments such as, for example, genes, or polypeptides. Nucleic acid sequencing allows for the determination of the order and position of nucleotides in a target nucleic acid molecule. Nucleic acid sequencing technologies may vary in the methods used to determine the nucleic acid sequence as well as in the rate, read length, and incidence of errors in the sequencing process. For example, some nucleic acid sequencing methods are based on sequencing by synthesis, in which the identity of a nucleotide is determined as the nucleotide is incorporated into a newly synthesized strand of nucleic acid that is complementary to the target nucleic acid molecule. Some sequencing by synthesis methods require the presence of a population of target nucleic acid molecules (e.g., copies of a target nucleic acid) or a step of amplification of the target nucleic acid to achieve a population of target nucleic acids.

Having recognized the need for simple, less complex apparatuses for performing single molecule detection and/or nucleic acid sequencing, the inventors have conceived of a technique for detecting single molecules using sets of markers, such as optical (e.g., luminescent) markers, to label different molecules. A tag may include a nucleotide or amino acid and a suitable marker. Markers may be detected while bound to single molecules, upon release from the single molecules, or while bound to and upon release from the single molecules. In some examples, markers are luminescent tags. Each luminescent marker in a selected set is associated with a respective molecule. For example, a set of four markers may be used to "label" the nucleobases present in DNA—each marker of the set being associated with a different nucleobase to form a tag, e.g., a first marker being associated with adenine (A), a second marker being associated with cytosine (C), a third marker being associated with guanine (G), and a fourth marker being associated with thymine (T). Moreover, each of the luminescent markers in the set of markers has different properties that may be used to distinguish a first marker of the set from the other markers in the set. In this way, each marker is uniquely identifiable using one or more of these distinguishing characteristics. By way of example and not limitation, the characteristics of the markers that may be used to distinguish one marker from another may include the emission energy and/or wavelength of the light that is emitted by the marker in response to excitation and/or the wavelength and/or energy of the excitation light that excites a particular marker. Distinguishing a marker from among the set of four markers uniquely identifies the nucleobase associated with the marker.

Luminescent markers may vary in the wavelength of light they emit, the temporal characteristics of the light they emit (e.g., their emission decay time periods), and their response to excitation energy (e.g., their probability of absorbing an excitation photon). Accordingly, luminescent markers may be identified or discriminated from other luminescent markers based on detecting these properties. Such identification or discrimination techniques may be used alone or in any suitable combination.

In some embodiments, an integrated photodetector as described in the present application can measure or discriminate luminescence lifetimes, such as fluorescence lifetimes. Lifetime measurements are based on exciting one or more markers (e.g., fluorescent molecules), and measuring the time variation in the emitted luminescence. The probability that a marker emits a photon after the marker reaches an excited state decreases exponentially over time. The rate at which the probability decreases may be characteristic of a marker, and may be different for different markers. Detecting the temporal characteristics of light emitted by markers may allow identifying markers and/or discriminating markers with respect to one another. The decrease in the probability of a photon being emitted over time may be represented by an exponential decay function $p(t)=e^{\wedge}(-t/\tau)$, where $p(t)$ is the probability of photon emission at a time, $t$, and $\tau$ is a temporal parameter of the marker. The temporal parameter $\tau$ indicates a time after excitation when the probability of the marker emitting a photon is a certain value. The temporal parameter, $\tau$, is a property of a marker that may be distinct from its absorption and emission spectral properties.

Such a temporal parameter, $\tau$, is referred to as the luminescence lifetime, the fluorescence lifetime or simply the "lifetime" of a marker.

FIG. 1-1 plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, $\tau$, or lifetime than the marker represented by probability curve A. Markers may have lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, lifetime measurements may be performed in which a plurality of markers having different lifetimes is excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers.

Lifetime measurements may use relative intensity measurements by comparing how intensity changes over time, as opposed to absolute intensity values. As a result, lifetime measurements may avoid some of the difficulties of absolute intensity measurements. Absolute intensity measurements may depend on the concentration of markers present and calibration steps may be needed for varying marker concentrations. By contrast, lifetime measurements may be insensitive to the concentration of markers.

Figures 1, 2, 2A:
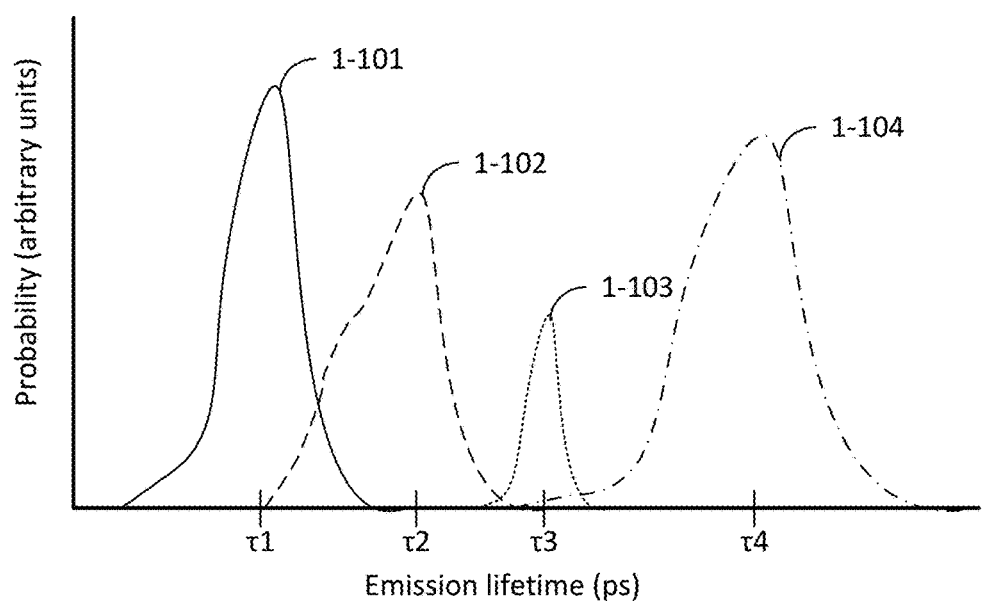

Embodiments may use any suitable combination of marker characteristics to distinguish a first marker in a set of markers from the other markers in the same set. For example, some embodiments may use only the timing information of the emission light from the markers to identify the markers. In such embodiments, each marker in a selected set of markers has a different emission lifetime from the other markers in the set and the luminescent markers are all excited by light from a single excitation source. FIG. 1-2A illustrates the emission timing from four luminescent markers according to an embodiment where the four markers exhibit different average emission lifetimes ($\tau$). The probability that a marker is measured to have a lifetime of a particular value is referred to herein as the marker's "emission timing." A first emission timing 1-101 from a first luminescent marker has a peak probability of having a lifetime of at $\tau 1$, a second emission timing 1-102 from a second luminescent marker has a peak probability of having a lifetime of at $\tau 2$, a third emission timing 1-103 from a third luminescent marker has a peak probability of having a lifetime of at $\tau 3$, and a fourth emission timing 1-104 from a fourth luminescent marker has a peak probability of having a lifetime of at $\tau 4$. In this embodiment, the lifetime probability peaks of the four luminescent markers may have any suitable values that satisfy the relation $\tau 1 < \tau 2 < \tau 3 < \tau 4$. The four timing emission graphs may or may not overlap due to slight variations in the lifetime of a particular luminescent marker, as illustrated in FIG. 1-2A. In this embodiment, the excitation wavelength at which each of the four markers maximally absorbs light from the excitation source is approximately equal, but that need not be the case. Using the above marker set, four different molecules may be labeled with a respective marker from the marker set, the markers may be excited using a single excitation source, and the markers can be distinguished from one another by detecting the emission lifetime of the markers using an optical system and sensors. While FIG. 1-2A illustrates four different markers, it should be appreciated that any suitable number of markers may be used.

Other embodiments may use any suitable combination of marker characteristics to determine the identity of the marker within a set of markers. Examples of the marker characteristics that may be used include, but are not limited to excitation wavelength, emission wavelength, and emission lifetime. The combination of marker characteristics form a phase space and each marker may be represented as a point within this phase space. Markers within a set of markers should be selected such that the "distance" between each marker within the set is sufficiently large that the detection mechanism can distinguish each marker from the other markers in the set. For example, in some embodiments a set of markers may be selected where a subset of the markers have the same emission wavelength, but have different emission lifetimes and/or different excitation wavelengths. In other embodiments, a set of markers may be selected where a subset of the markers have the same emission lifetime, but have different emission wavelengths and/or different excitation wavelengths. In other embodiments, a set of markers may be selected where a subset of the markers have the same excitation wavelength, but have different emission wavelengths and/or different emission lifetimes.

Figures 1, 2, 2B:
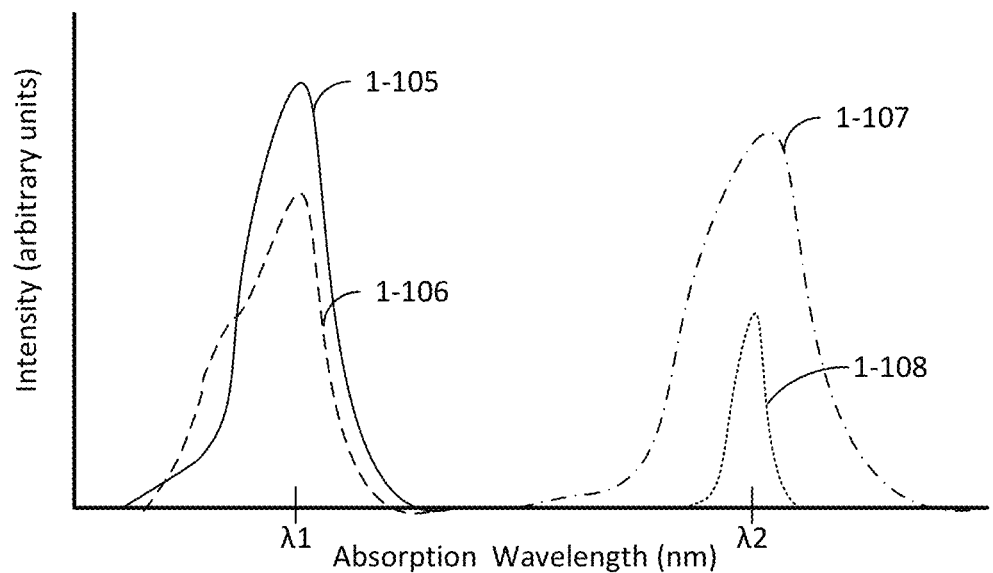

By way of example and not limitation, FIG. 1-2B illustrates the emission spectra from four luminescent markers according to an embodiment where two of the markers have a first peak emission wavelength and the other two markers have a second peak emission wavelength. A first emission spectrum 1-105 from a first luminescent marker has a peak emission wavelength at $\lambda 1$, a second emission spectrum 1-106 from a second luminescent marker also has a peak emission wavelength at $\lambda 1$, a third emission spectrum 1-107 from a third luminescent marker has a peak emission wavelength at $\lambda 2$, and a fourth emission spectrum 1-108 from a fourth luminescent marker also has a peak emission wavelength at $\lambda 2$. In this embodiment, the emission peaks of the four luminescent markers may have any suitable values that satisfy the relation $\lambda 1 < \lambda 2$. In embodiments such as this where the peak emission wavelength is the same for more than one luminescent marker, a separate characteristic of the markers that have the same emission wavelength must be different. For example, the two markers that emit at $\lambda 1$ may have different emission lifetimes. FIG. 1-3A illustrates this situation schematically in a phase space spanned by the emission wavelength and the emission lifetime. A first marker has an emission wavelength $\lambda 1$ and an emission lifetime $\tau 1$, a second marker has an emission wavelength $\lambda 1$ and a emission lifetime $\tau 4$, a third marker has an emission wavelength $\lambda 2$ and a emission lifetime $\tau 1$, and a fourth marker has an emission wavelength $\lambda 2$ and a emission lifetime $\tau 4$. In this way, all four markers in the marker set shown in FIG. 1-3A are distinguishable from one another. Using such a marker set allows distinguishing between four markers even when the absorption wavelengths for the four markers are identical. This is possible using a sensor that can detect the time of emission of the photoluminescence as well as the emission wavelength.

Figures 1, 2, 2C:
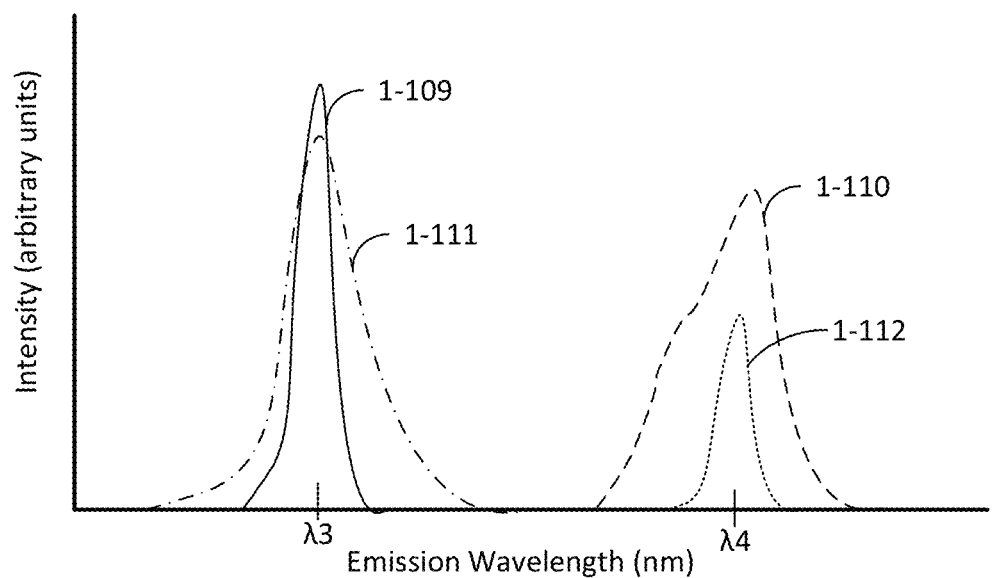

By way of example and not limitation, FIG. 1-2C illustrates the absorption spectra from four luminescent markers according to another embodiment. In this embodiment, two of the markers have a first peak absorption wavelength and the other two markers have a second peak absorption wavelength. A first absorption spectrum 1-109 for the first luminescent marker has a peak absorption wavelength at $\lambda 3$, a second absorption spectrum 1-110 for the second luminescent marker has a peak absorption wavelength at $\lambda 4$, a third absorption spectrum 1-111 for the third luminescent marker has a peak absorption wavelength at $\lambda 3$, and a fourth absorption spectrum 1-112 for the fourth luminescent marker has a peak absorption wavelength at $\lambda 4$. Note that the markers that share an absorption peak wavelength in FIG. 1-2C are distinguishable via another marker characteristic, such as emission lifetime. FIG. 1-3B illustrates this situation schematically in a phase space spanned by the absorption wavelength and the emission lifetime. A first marker has an absorption wavelength $\lambda 3$ and an emission lifetime $\tau 1$, a second marker has an absorption wavelength $\lambda 3$ and an emission lifetime $\tau 4$, a third marker has an absorption wavelength $\lambda 4$ and an emission lifetime $\tau 1$, and a fourth marker has an absorption wavelength $\lambda 4$ and an emission lifetime $\tau 4$. In this way, all four markers in the marker set shown in FIG. 1-3A are distinguishable from one another.

Using such a marker set allows for distinguishing between four markers even when the emission wavelengths for the four markers are indistinguishable. This is possible using two excitation sources that emit at different wavelengths or a single excitation source capable of emitting at multiple wavelengths in connection with a sensor that can detect the time of emission of the photoluminescence. If the wavelength of the excitation light is known for each detected emission event, then it can be determined which marker was present. The excitation source(s) may alternate between a first excitation wavelength and a second excitation wavelength, which is referred to as interleaving. Alternatively, two or more pulses of the first excitation wavelength may be used followed by two or more pulses of the second excitation wavelength.

The number of excitation sources or excitation wavelengths used to distinguish the markers is not limited to two, and in some embodiments more than two excitation wavelengths or energies may be used to distinguish the markers. In such embodiments, markers may be distinguished by the intensity or number of photons emitted in response to multiple excitation wavelengths. A marker may be distinguishable from among multiple markers by detecting the number of photons emitted in response to exposing the marker to a certain excitation wavelength. In some embodiments, a marker may be distinguished by illuminating the marker to one of multiple excitation energies at a time and identifying the excitation energy from among the multiple excitation energies where the marker emitted the highest number of photons. In other embodiments, the number of photons emitted from a marker in response to different excitation energies may be used to identify the marker. A first marker that has a higher probability of emitting photons in response to a first excitation energy than a second excitation energy may be distinguished from a second marker that has a higher probability of emitting photons in response to the second excitation energy than the first excitation energy. In this manner, markers having distinguishable probabilities of emitting certain amounts of photons in response to different excitation energies may be identified by measuring the emitted photons while exposing an unknown marker to the different excitation energies. In such embodiments, a marker may be exposed to multiple excitation energies and identification of the marker may be achieved by determining whether the marker emitted any light and/or a particular number of photons emitted. Any suitable number of excitation energy sources may be used. In some embodiments, four different excitation energies may be used to distinguish among different markers (e.g., four different markers). In some embodiments, three different excitation energies may be used to distinguish among different markers. Other characteristics of a marker may be used to distinguish the presence of a marker in combination with the amount of photons emitted in response to different excitation energies, including emission lifetime and emission spectra.

In other embodiments more than two characteristics of the markers in a marker set may be used to distinguish which marker is present. FIG. 1-4 illustrates an illustrative phase space spanned by the absorption wavelength, the emission wavelength and the emission lifetime of the markers. In FIG. 1-4, eight different markers are distributed in the phase space. Four of the eight markers have the same emission wavelength, a different four markers have the same absorption wavelength and a different four markers have the same emission lifetime. However, each of the markers is distinguishable from every other marker when all three characteristics of the markers are considered. Embodiments are not limited to any number of markers. This concept can be extended to include any number of markers that may be distinguished from one another using at least these three marker characteristics.

While not illustrated in the figures, other embodiments may determine the identity of a luminescent marker based on the absorption frequency alone. Such embodiments are possible if the excitation light can be tuned to specific wavelengths that match the absorption spectrum of the markers in a marker set. In such embodiments, the optical system and sensor used to direct and detect the light emitted from each marker does not need to be capable of detecting the wavelength of the emitted light. This may be advantageous in some embodiments because it reduces the complexity of the optical system and sensors because detecting the emission wavelength is not required in such embodiments.

As discussed above, the inventors have recognized and appreciated the need for being able to distinguish different luminescent markers from one another using various characteristics of the markers. The type of characteristics used to determine the identity of a marker impacts the physical device used to perform this analysis. The present application discloses several embodiments of an apparatus, device, instrument and methods for performing these different experiments.

The inventors have recognized and appreciated that a low-cost, single-use disposable integrated device that includes optics and sensors may be used in connection with an instrument that includes an excitation source to measure different characteristics of luminescent light emitted from one or markers used to label a biological sample in order to analyze the sample. Using a low-cost integrated device reduces the cost of performing a given bioassay. A biological sample is placed onto the integrated device and, upon completion of the bioassay, may be discarded. The integrated device interfaces with the more expensive, multi-use instrument, which may be used repeatedly with many different disposable integrated devices. A low-cost integrated device that interfaces with a compact, portable instrument may be used anywhere in the world, without the constraint of high-cost biological laboratories requiring laboratory expertise to analyze samples. Thus, automated bioanalytics may be brought to regions of the world that previously could not perform quantitative analysis of biological samples. For example, blood tests for infants may be performed by placing a blood sample on a disposable integrated device, placing the disposable integrated device into the small, portable instrument for analysis, and processing the results by a computer that connects to the instrument for immediate review by a user. The data may also be transmitted over a data network to a remote location to be analyzed, and/or archived for subsequent clinical analyses. Alternatively, the instrument may include one or more processors for analyzing the data obtained from the sensors of the integrated device.

I. Overview of the System

The system includes an integrated device and an instrument configured to interface with the integrated device. The integrated device includes an array of pixels, where a pixel includes a sample well and at least one sensor. A surface of the integrated device has a plurality of sample wells, where a sample well is configured to receive a sample from a specimen placed on the surface of the integrated device. A specimen may contain multiple samples, and in some embodiments, different types of samples. The plurality of sample wells may have a suitable size and shape such that at least a portion of the sample wells receive one sample from a specimen. In some embodiments, the number of samples within a sample well may be distributed among the sample wells such that some sample wells contain one sample with others contain zero, two or more samples.

In some embodiments, a specimen may contain multiple single-stranded DNA templates, and individual sample wells on a surface of an integrated device may be sized and shaped to receive a single-stranded DNA template. Single-stranded DNA templates may be distributed among the sample wells of the integrated device such that at least a portion of the sample wells of the integrated device contain a single-stranded DNA template. The specimen may also contain tagged nucleotides (e.g., dNTPs) which then enter in the sample well and may allow for identification of a nucleotide as it is incorporated into a strand of DNA complementary to the single-stranded DNA template in the sample well. In such an example, the "sample" may refer to both the single-stranded DNA and the tagged nucleotide (e.g., dNTP) currently being incorporated by a polymerase. In some embodiments, the specimen may contain single-stranded DNA templates and tagged nucleotides (e.g., dNTPs) may be subsequently introduced to a sample well as nucleotides are incorporated into a complementary strand of DNA within the sample well. In this manner, timing of incorporation of nucleotides may be controlled by when tagged nucleotides (e.g., dNTPs) are introduced to the sample wells of an integrated device.

Excitation energy is provided from an excitation source located separate from the pixel array of the integrated device. The excitation energy is directed at least in part by elements of the integrated device towards one or more pixels to illuminate an illumination region within the sample well. A marker or tag may then emit emission energy when located within the illumination region and in response to being illuminated by excitation energy. In some embodiments, one or more excitation sources are part of the instrument of the system where components of the instrument and the integrated device are configured to direct the excitation energy towards one or more pixels.

Emission energy emitted by a sample may then be detected by one or more sensors within a pixel of the integrated device. Characteristics of the detected emission energy may provide an indication of the marker that emitted the emission energy and may be used for identifying the marker associated with the emission energy. Such characteristics may include any suitable type of characteristic of light, including an arrival time of photons detected by a sensor, an amount of photons accumulated over time by a sensor, and/or a distribution of photons across two or more sensors. In some embodiments, a sensor may have a configuration that allows for the detection of one or more timing characteristics associated with a sample's emission energy (e.g., fluorescence lifetime). The sensor may detect a distribution of photon arrival times after a pulse of excitation energy propagates through the integrated device, and the distribution of arrival times may provide an indication of a timing characteristic of the sample's emission energy (e.g., a proxy for fluorescence lifetime). In some embodiments, the one or more sensors provide an indication of the probability of emission energy emitted by the marker or tag (e.g., fluorescence intensity). In some embodiments, a plurality of sensors may be sized and arranged to capture a spatial distribution of the emission energy. Output signals from the one or more sensors may then be used to distinguish a marker from among a plurality of markers, where the plurality of markers may be used to identify a sample within the specimen. In some embodiments, a sample may be excited by multiple excitation energies, and emission energy and/or timing characteristics of the emission energy emitted by the sample in response to the multiple excitation energies may distinguish a marker from a plurality of markers.

Figures 1A, 2:
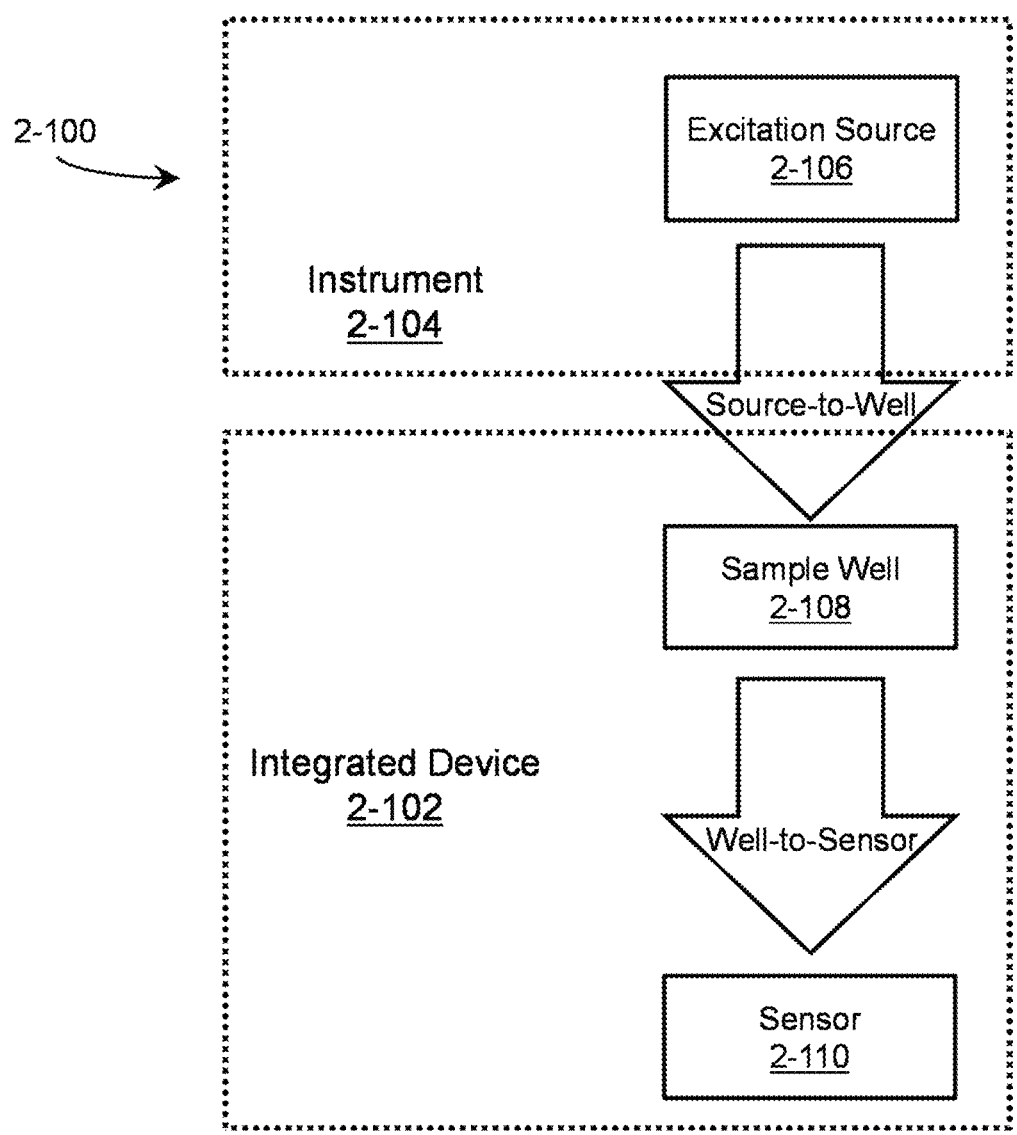
Figures 1B, 2:
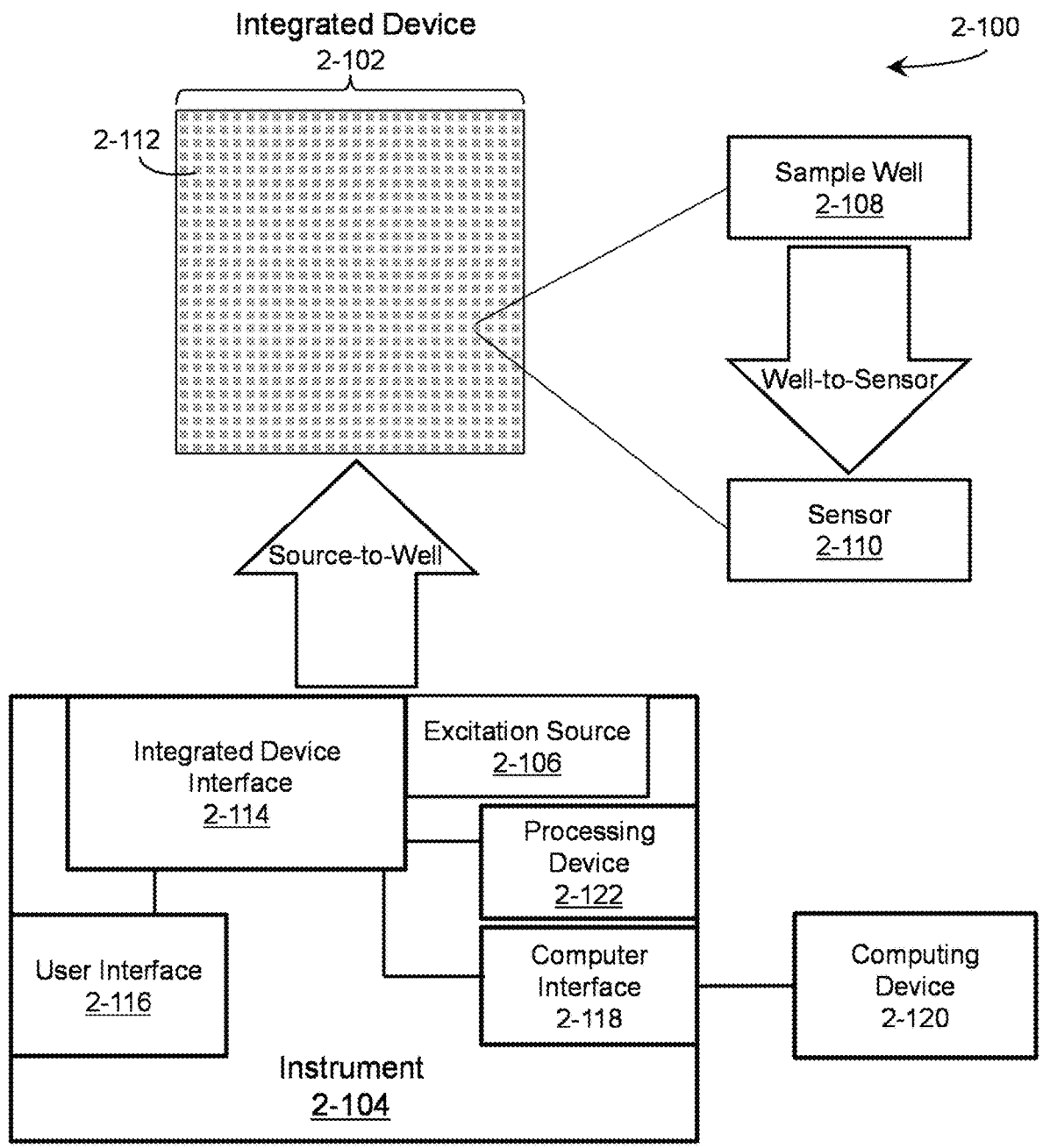

A schematic overview of the system 2-100 is illustrated in FIGS. 2-1A and 2-1B. The system comprises both an integrated device 2-102 that interfaces with an instrument 2-104. In some embodiments, instrument 2-104 may include one or more excitation sources 2-106 integrated as part of instrument 2-104. In some embodiments, an excitation source may be external to both instrument 2-104 and integrated device 2-102, and instrument 2-104 may be configured to receive excitation energy from the excitation source and direct it to the integrated device. The integrated device may interface with the instrument using any suitable socket for receiving the integrated device and holding it in precise optical alignment with the excitation source. The excitation source 2-106 may be configured to provide excitation energy to the integrated device 2-102. As illustrated schematically in FIG. 2-1B, the integrated device 2-102 has multiple pixels, where at least a portion of pixels 2-112 may perform independent analysis of a sample. Such pixels 2-112 may be referred to as "passive source pixels" since a pixel receives excitation energy from a source 2-106 separate from the pixel, where the source excites a plurality of pixels. A pixel 2-112 has a sample well 2-108 configured to receive a sample and a sensor 2-110 for detecting emission energy emitted by the sample in response to illuminating the sample with excitation energy provided by the excitation source 2-106. Sample well 2-108 may retain the sample in proximity to a surface of integrated device 2-102 to provide ease in delivery of excitation energy to the sample and detection of emission energy from the sample.

Optical elements for guiding and coupling excitation energy to the sample well 2-108 are located both on integrated device 2-102 and the instrument 2-104. Such source-to-well elements may comprise one or more grating couplers located on integrated device 2-102 to couple excitation energy to the integrated device and waveguides to deliver excitation energy from instrument 2-104 to sample wells in pixels 2-112. In some embodiments, elements located on the integrated device may act to direct emission energy from the sample well towards the sensor. Sample well 2-108, a portion of the excitation source-to-well optics, and the sample well-to-sensor optics may be located on integrated device 2-102. Excitation source 2-106 and a portion of the source-to-well components may be located in instrument 2-104. In some embodiments, a single component may play a role in both coupling excitation energy to sample well 2-108 and delivering emission energy from sample well 2-108 to sensor 2-110. Examples of suitable components, for coupling excitation energy to a sample well and/or directing emission energy to a sensor, to include in an integrated device are described in U.S. patent application Ser. No. 14/821,688 entitled "INTEGRATED DEVICE FOR PROBING, DETECTING AND ANALYZING MOLECULES," and U.S. patent application Ser. No. 14/543,865 entitled "INTEGRATED DEVICE WITH EXTERNAL LIGHT SOURCE FOR PROBING, DETECTING, AND ANALYZING MOLECULES," both of which are incorporated by reference in their entirety.

As illustrated in FIG. 2-1B, the integrated device comprises a plurality of pixels where a pixel 2-112 is associated with its own individual sample well 2-108 and at least one sensor 2-110. The plurality of pixels may be arranged in an array, and there may be any suitable number of pixels in the array. The number of pixels in integrated device 2-102 may be in the range of approximately 10,000 pixels to 10,000,000 pixels or any value or range of values within that range. In some embodiments, the integrated device may have 512,000 pixels, 32,000 pixels, 64,000 pixels, or 8,000,000 pixels. In some embodiments, the pixels may be arranged in an array of 512 pixels by 512 pixels. Integrated device 2-102 and instrument 2-104 may include multi-channel, high-speed communication links for handling data associated with large pixel arrays (e.g., more than 10,000 pixels).

Instrument 2-104 interfaces with integrated device 2-102 through integrated device interface 2-114. Integrated device interface 2-114 may include components to position and/or align integrated device 2-102 to instrument 2-104 to improve coupling of excitation energy from excitation source 2-106 to integrated device 2-102. Excitation source 2-106 may be any suitable light source that is arranged to deliver excitation energy to at least one sample well. Examples of suitable excitation sources are described in U.S. patent application Ser. No. 14/821,688 entitled "INTEGRATED DEVICE FOR PROBING, DETECTING AND ANALYZING MOLECULES," which is incorporated by reference in its entirety. In some embodiments, excitation source 2-106 includes multiple excitation sources that are combined to deliver excitation energy to integrated device 2-102. The multiple excitation sources may be configured to produce multiple excitation energies and/or wavelengths. The integrated device interface 2-114 may receive readout signals from the sensors in the pixels located on the integrated device. The integrated device interface 2-114 may be designed such that the integrated device attaches to the instrument by securing the integrated device to the integrated device interface 2-114.

The instrument 2-104 includes a user interface 2-116 for controlling the operation of instrument 2-104. The user interface 2-116 is configured to allow a user to input information into the instrument, such as commands and/or settings used to control the functioning of the instrument. In some embodiments, the user interface 2-116 may include buttons, switches, dials, and a microphone for voice commands. Additionally, the user interface 2-116 may allow a user to receive feedback on the performance of the instrument and/or integrated device, such as proper alignment and/or information obtained by readout signals from the sensors on the integrated device. In some embodiments, the user interface 2-116 may provide feedback using a speaker to provide audible feedback, and indicator lights and/or display screen for providing visual feedback. In some embodiments, the instrument 2-104 includes a computer interface 2-118 used to connect with a computing device 2-120. Any suitable computer interface 2-118 and computing device 2-120 may be used. For example, the computer interface 2-118 may be a USB interface or a FireWire interface. The computing device 2-120 may be any general purpose computer, such as a laptop or desktop computer. The computer interface 2-118 facilitates communication of information between the instrument 2-104 and the computing device 2-120. Input information for controlling and/or configuring the instrument 2-104 may be provided through the computing device 2-120 connected to the computer interface 2-118 of the instrument. Output information may be received by the computing device 2-120 through the computer interface 2-118. Such output information may include feedback about performance of the instrument 2-104 and/or integrated device 2-112 and information from the readout signals of the sensor 2-110. The instrument 2-104 may also include a processing device 2-122 for analyzing data received from the sensor 2-110 and/or sending control signals to the excitation source 2-106. In some embodiments, the processing device 2-122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 2-110 may be performed by both the processing device 2-122 and the external computing device 2-120. In other embodiments, the computing device 2-120 may be omitted and processing of data from the sensor 2-110 may be performed solely by processing device 2-122.

Figures 1, 2, 3, 3A:
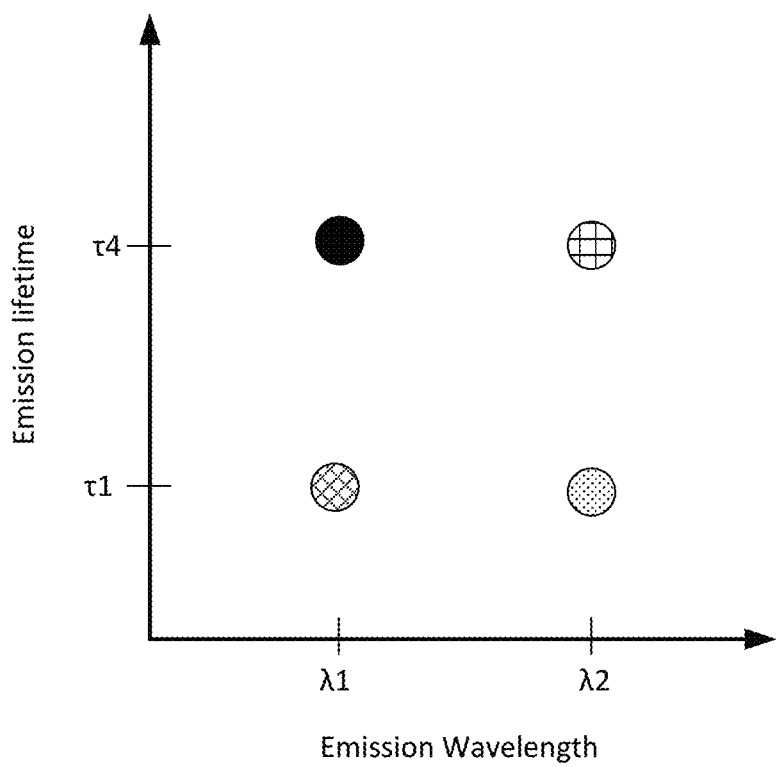

A cross-sectional schematic of the integrated device 3-102 illustrating a row of pixels is shown in FIG. 3-1A. A pixel 3-112 includes a sample well 3-108 and a sensor 3-110. The sensor 3-110 may be aligned and positioned to sample well 3-112 such that sensor 3-110 receives emission energy emitted by a sample within sample well 3-112. Examples of suitable sensors are described in U.S. patent application Ser. No. 14/821,656 entitled "INTEGRATED DEVICE FOR TEMPORAL BINNING OF RECEIVED PHOTONS," which is incorporated by reference in its entirety.

An excitation source coupled to the integrated device may provide excitation energy to one or more pixels of integrated device 3-102. FIG. 3-1B is a schematic illustrating coupling of excitation source 3-106 to integrated device 3-102 to provide excitation energy 3-130 (shown in dashed lines) to integrated device 3-102. FIG. 3-1B illustrates the path of excitation energy from excitation energy source 3-106 to a sample well 3-108 in pixel 3-112. Components located off of the integrated device may be used to position and align the excitation source 3-106 to the integrated device. Such components may include optical components including lenses, mirrors, prisms, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. Pat. Application 62/310,398 entitled "PULSED LASER AND SYSTEM," which is incorporated by reference in its entirety.

The integrated device includes components that direct the excitation energy 3-130 towards pixels in the integrated device. Within each pixel 3-112, excitation energy is coupled to the sample well 3-108 associated with the pixel. Although FIG. 3-1B illustrates excitation energy coupling to each sample well in a row of pixels, in some embodiments, excitation energy may not couple to all of the pixels in a row. In some embodiments, excitation energy may couple to a portion of pixels or sample wells in a row of pixels of the integrated device. Excitation energy may illuminate a sample located within a sample well. The sample may reach an excited state in response to being illuminated by the excitation energy. When a sample is in an excited state, the sample may emit emission energy and the emission energy may be detected by a sensor. FIG. 3-1B schematically illustrates the path of emission energy 3-140 (shown as solid lines) from sample well 3-108 to sensor 3-110 of pixel 3-112. Sensor 3-110 in pixel 3-112 may be configured and positioned to detect emission energy from sample well 3-108. In some embodiments, sensor 3-110 may include multiple sub-sensors.

A sample to be analyzed may be introduced into sample well 3-108 of pixel 3-112. The sample may be a biological sample or any other suitable sample, such as a chemical sample. The sample may include multiple molecules and the sample well may be configured to isolate a single molecule. In some instances, the dimensions of the sample well may act to confine a single molecule within the sample well, allowing measurements to be performed on the single molecule. An excitation source 3-106 may be configured to deliver excitation energy into the sample well 3-108, so as to excite the sample or at least one luminescent marker attached to the sample or otherwise associated with the sample while it is within an illumination area within the sample well 3-108.

When an excitation source delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

One or more components of an integrated device may direct emission energy towards a sensor. The emission energy or energies may be detected by the sensor and converted to at least one electrical signal. The electrical signals may be transmitted along conducting lines in the circuitry of the integrated device connected to the instrument through the integrated device interface, such as integrated device interface 2-114 of instrument 2-104 shown in FIG. 2-1B. The electrical signals may be subsequently processed and/or analyzed. Processing or analyzing of electrical signals may occur on a suitable computing device either located on the instrument 2-104 or off instrument, such as computing device 2-120 shown in FIG. 2-1B.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

In some embodiments, a sample may be labeled with one or more markers, and emission associated with the markers is discernable by the instrument. For example the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor.

A sample may contain multiple types of molecules and different luminescent markers may uniquely associate with a molecule type. During or after excitation, the luminescent marker may emit emission energy. One or more properties of the emission energy may be used to identify one or more types of molecules in the sample. Properties of the emission energy used to distinguish among types of molecules may include a fluorescence lifetime value, intensity, and/or emission wavelength. A sensor may detect photons, including photons of emission energy, and provide electrical signals indicative of one or more of these properties. In some embodiments, electrical signals from a sensor may provide information about a distribution of photon arrival times across one or more time intervals. The distribution of photon arrival times may correspond to when a photon is detected after a pulse of excitation energy is emitted by an excitation source. A value for a time interval may correspond to a number of photons detected during the time interval. Relative values across multiple time intervals may provide an indication of a temporal characteristic of the emission energy (e.g., lifetime). Analyzing a sample may include distinguishing among markers by comparing values for two or more different time intervals within a distribution. In some embodiments, an indication of the intensity may be provided by determining a number of photons across all time bins in a distribution.

II. Integrated Device

Performance of an integrated device in analyzing samples can depend on the amount of excitation energy (e.g., optical power) delivered to individual sample wells. As excitation energy propagates from an excitation source to a sample well, optical loss may occur which may reduce the amount of excitation energy that couples to the sample well and impact the performance of the pixel associated with the sample well in detecting the sample. For an array of sample wells, such optical loss may limit the number of pixels capable of sample detection. In some instances, such optical loss may reduce the uniformity in delivering excitation energy to individual sample wells in the array. A waveguide of the integrated device may couple excitation energy to a number of sample wells (e.g., 512 sample wells) positioned proximate to the waveguide. As excitation energy propagates along the waveguide, the amount of total optical loss may increase, reducing the amount of excitation energy that couples to sample wells positioned further along the waveguide. In this manner, optical loss along the waveguide may impact the uniformity in the amount of excitation energy coupled to individual sample wells positioned proximate to the waveguide. Aspects of the present application relate to integrated devices, and methods of forming integrated devices, that improve uniformity of excitation energy within the array of sample wells by reducing optical loss as excitation energy propagates along a waveguide.

One type of optical loss can arise from the proximity of a waveguide of the integrated device to a surface of the device. The optical loss can be enhanced when the surface is formed of a metal layer over a cladding layer of the integrated device. The waveguide of the integrated device may deliver excitation energy to multiple sample wells positioned on a surface of the integrated device where the sample wells are formed through the metal layer. The distance between an individual sample well and the waveguide may allow for coupling of excitation energy from the waveguide to the sample well, but the proximity of the waveguide to the metal layer may contribute to loss of excitation energy propagating along the waveguide. Accordingly, aspects of the present application relate to techniques of forming an integrated device where the distance between a waveguide and a metal layer of the integrated device varies along the waveguide. Some embodiments relate to portions of the metal layer that include one or more sample wells positioned at a distance closer to the waveguide than a portion of the metal layer that lacks a sample well. In this manner, sample wells can be positioned at a suitable distance to the waveguide for a desired level of excitation energy coupling while reducing optical loss that may arise from the proximity of the waveguide to the metal layer by having a thicker cladding elsewhere along the waveguide.

The region that includes at least one sample well may be recessed from another portion of the surface of the integrated device. In some embodiments, a first region of the surface that includes at least one sample well and overlaps with the waveguide is positioned at a smaller distance to the waveguide than a second region of the surface that overlaps with the waveguide but does not include a sample well. A recessed region of the surface may be formed by etching the region during formation of the integrated device and may be referred to as a "trench" region. In some embodiments, a trench region may include a single sample well such that individual trench regions are formed surrounding individual sample wells. In some embodiments, a trench region may include multiple sample wells, such as a row of sample wells (e.g., sample wells positioned along a waveguide) or multiple rows of sample wells (e.g., the entire sample well array).

Another type of optical loss can arise from the proximity of a waveguide to a component of the device that impacts the ability of light to propagate along the waveguide. In some embodiments, an integrated device may include metal components, which may contribute to optical loss along a waveguide. Some embodiments of the integrated device include sample wells formed within a metal layer on the surface of the integrated device. The metal layer may provide benefits in detecting emission energy from a sample well by one or more sensors. The metal layer may act to reduce background signals and to improve the amount of emission energy detected by the one or more sensors. Formation of a trench region, that includes one or more sample wells, may reduce optical loss that arises from the proximity of the metal layer to the waveguide.

In some embodiments, the integrated device may include metal layers configured to act as wiring to transmit and/or receive electrical signals. Such wiring may couple to a sensor and transmit signals to control the sensor and/or receive signals indicative of the emission energy detected by the sensor. Some embodiments relate to formation of a trench region to accommodate metal wiring while providing proximity of one or more sample wells to a waveguide and/or a sensor.

Some embodiments relate to techniques for improving uniformity across multiple sample wells in the amount of excitation energy that couples into each sample well. Optical components of the integrated device may be suitably sized and shaped such that the amount of excitation energy coupled to multiple sample wells has a level of power within a desired tolerance amount. An integrated device may include a grating coupler configured to receive excitation energy and direct the excitation energy into one or more waveguides. A waveguide may have a configuration that allows for coupling of excitation energy into one or more sample wells. In some embodiments, one or more optical splitter components (e.g., star coupler, multimode interference splitter) may be configured to receive light (e.g., excitation energy) from the grating coupler and direct light into two or more waveguides where each waveguide is positioned proximate to multiple sample wells. Such an optical splitter component may have a configuration that provides an approximately uniform distribution of light among multiple waveguides of the integrated device. Distributing excitation energy among multiple waveguides in a uniform manner may improve the uniformity of excitation energy received by the sample wells in the array.

In some embodiments, a waveguide of the integrated device may taper in one or more dimensions in a direction perpendicular to the direction of light propagation. Such a tapering of the waveguide may allow for the waveguide to couple approximately the same amount of excitation energy into a row of sample wells positioned proximate to the waveguide. As an excitation energy pulse propagates along the waveguide and couples excitation energy to the sample wells in the row, the amount of excitation energy may decrease. Decreasing a dimension of the waveguide may alter the propagation mode of the waveguide to account for the decreasing power such that each of the sample wells in the row receives approximately the same amount of excitation energy.

FIG. 3-2A is a schematic of a planar view of an integrated device, according to some embodiments. Excitation energy may couple to grating coupler 3-200 and propagate along a waveguide to splitter 3-202. Splitter 3-202 (e.g., star coupler, multimode interference (MMI) coupler) may couple excitation energy to a plurality of waveguides configured to direct excitation energy to pixel array 3-204 of the integrated device. Grating coupler 3-200 may have a configuration where coupling efficiency is improved by positioning a beam of excitation energy incident to grating coupler 3-200 in a direction at an angle from the normal to the xy-plane. Grating coupler 3-200 may be positioned relative to pixel array 3-204 such that excitation energy incident to grating coupler is directed away from pixel array 3-204. Such a configuration may reduce excitation energy from reaching and being detected by a sensor positioned within pixel array 3-204 of the integrated device, which may improve the signal-to-noise ratio of measurements performed by the integrated device. As shown in FIG. 3-2A, the waveguide that directs light from grating coupler 3-200 to splitter 3-202 has a U-turn shape 3-201 to allow for grating coupler 3-200 to receive excitation energy incident to grating coupler 3-220 while still couple excitation energy to splitter 3-202. The U-turn shape 3-201 allows for the efficiency of grating coupler 3-200 to be improved when a beam of excitation energy incident to grating coupler 3-200 is at an angle from the normal of the xy-plane in a direction of the negative x-direction. In this manner, the beam of excitation energy may arrive from an angle towards pixel array 3-204 such that excitation energy reaching the xy-plane shown in FIG. 3-2A is directed away from pixel array 3-204.

Splitter 3-202 may have a configuration that improves uniformity of excitation energy across the waveguides connected to splitter 3-202. In some embodiments, splitter 3-202 may provide approximately uniform amounts of excitation energy across 128 waveguides. Individual waveguides may be tapered in a dimension perpendicular to the direction of light propagation along a waveguide. In FIG. 3-2A, waveguides within pixel array 3-204 may have a tapering of dimension individual waveguides along the y-direction.

Pixel array 3-204 may overlap with a trench region, according to techniques described herein. In some embodiments, pixel array 3-204 may have a dimension of approximately 2.7 mm. Individual sensors associated with pixels of pixel array 3-204 may be formed to overlap with pixel array 3-204.

The integrated device may include an area for detecting excitation energy at the ends of individual waveguides. Monitoring region 3-206 may include a grating coupler coupled to individual waveguides. A grating coupler in region 3-206 may be configured to direct excitation energy from a waveguide to a monitoring sensor positioned to overlap, at least in part, with monitoring region 3-206. The detection of excitation energy by the monitoring sensor may provide an indication of the amount of excitation energy in a waveguide after a pulse of excitation energy travels along the waveguide (in the negative x-direction) and couples excitation energy into sample wells positioned proximate to the waveguide.

Some embodiments relate to an integrated device having duplicate structures and/or test structures to provide improved performance with operating the integrated device. In some embodiments, an integrated device may include multiple grating couplers coupled to an optical splitter component where each of the grating couplers is configured to receive excitation energy from an external source. FIG. 3-2B is a schematic of a planar view of an integrated device that includes input grating couplers 3-210 coupled to splitter 3-212. Multiple grating couplers 3-210 may provide redundancy in the number of inputs for excitation energy to couple with the integrated device. While only one of the grating couplers may be used during operation of the integrated device to analyze a sample, a grating coupler from among the multiple grating couplers 3-210 may be selected for use during operation based on a performance level for each of the multiple grating couplers 3-210. The performance level for an input grating coupler may be determined based on an indication related to the amount of excitation energy received across multiple sample wells in pixel array 3-214 and/or the amount of excitation energy received at one or more waveguide outputs. Once an integrated device is loaded into the instrument, the selected grating coupler may be identified by determining which of the grating couplers 3-210 provides a desired level of excitation energy distribution within the integrated device. In some embodiments, the multiple input grating couplers 3-210 may allow for continued use of the integrated device if the integrated device experiences performance below a desired threshold during operation of the integrated device. Rather than replacing with a different integrated device, the excitation energy beam may be positioned on a different grating coupler 3-210 to achieve improved performance and continue operation with the integrated device to analyze a sample.

An integrated device may also include optical structures configured to provide evaluation and/or testing capabilities of the integrated device prior to operation of the integrated device by a user. Such test structures may allow for evaluation of the integrated during fabrication and/or assembly as part of quality control measures. Some test structures may also be used as part of an evaluation process for an integrated device interfacing with the instrument that includes the excitation source. Test structures 3-216, 3-218, 3-220, and 3-224 may include spiral structures coupled to input and output grating couplers, which may be used to measure the amount of optical loss in the waveguide structures. A beam of light may be aligned to couple with a grating coupler at one end of a test structure and a sensor positioned to receive light emitted from another end of the test structure to provide an indication of the amount of light that remains after passing through the test structure.

Figures 1A, 3:
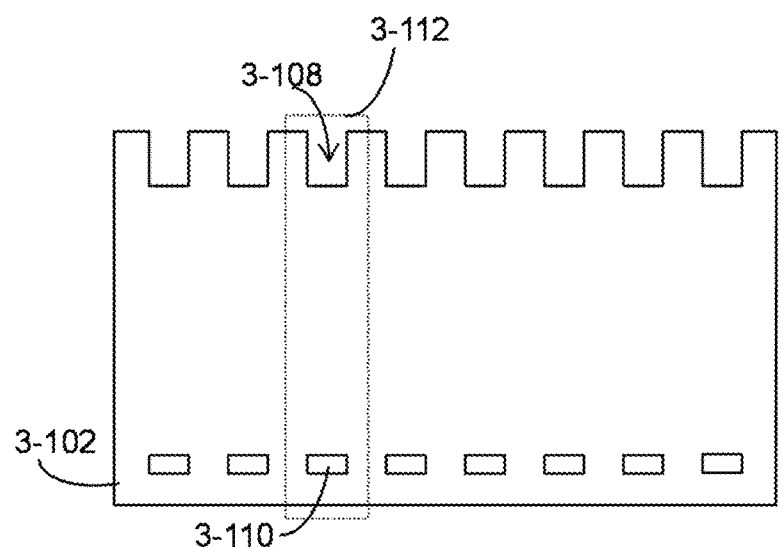
Figures 1B, 3:
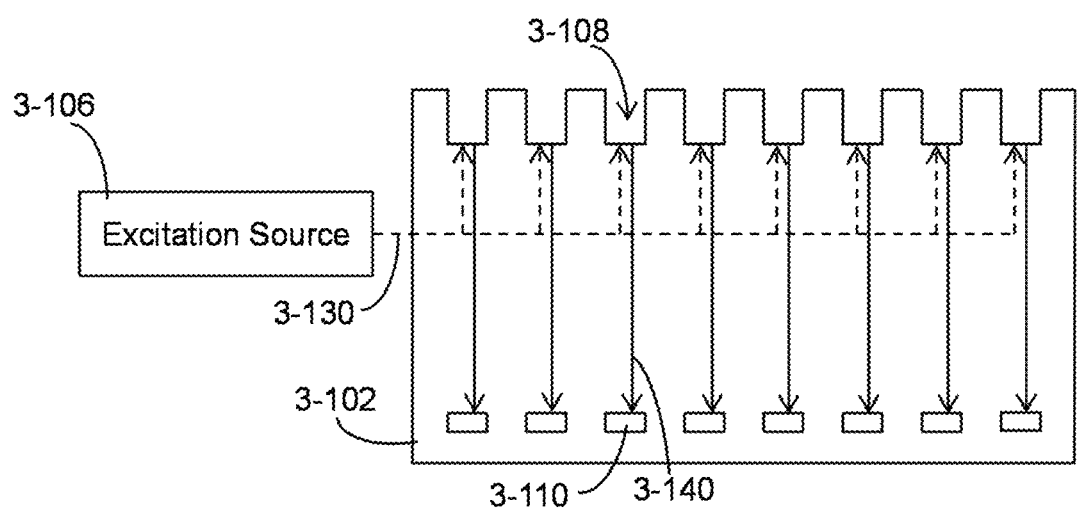
Figures 2A, 3:
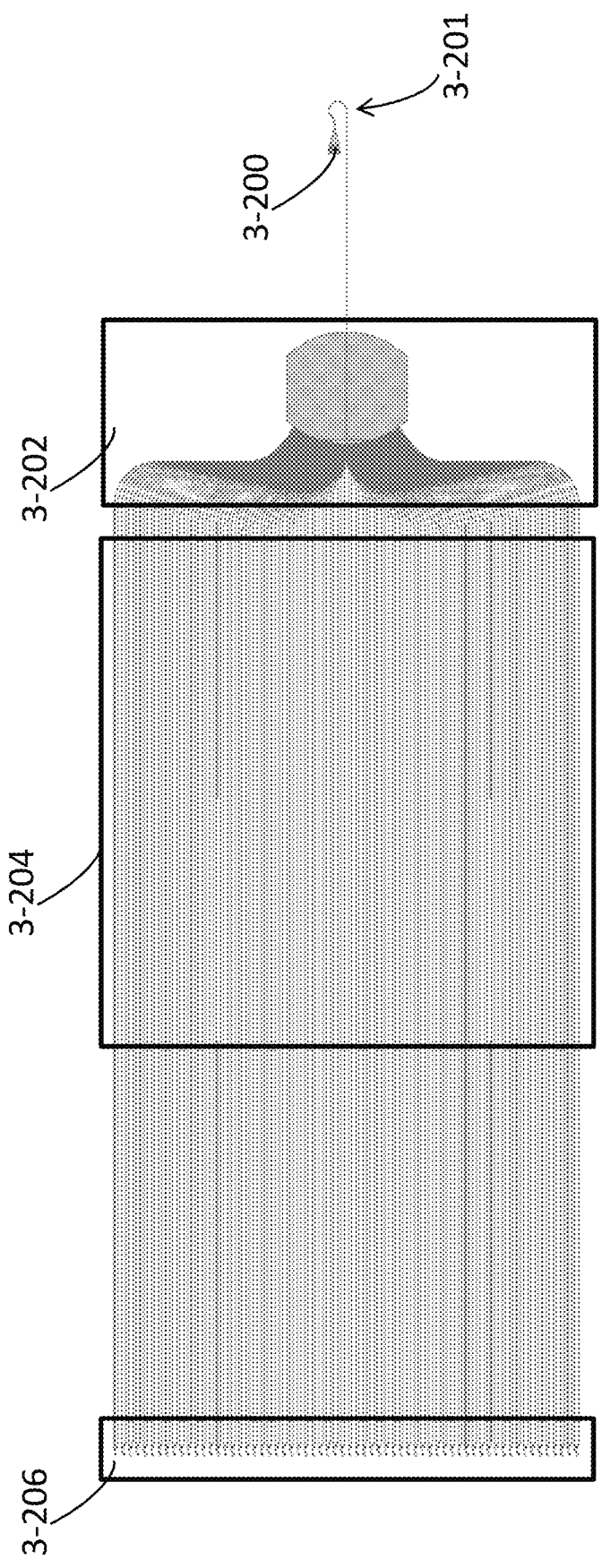
Figures 2B, 3:
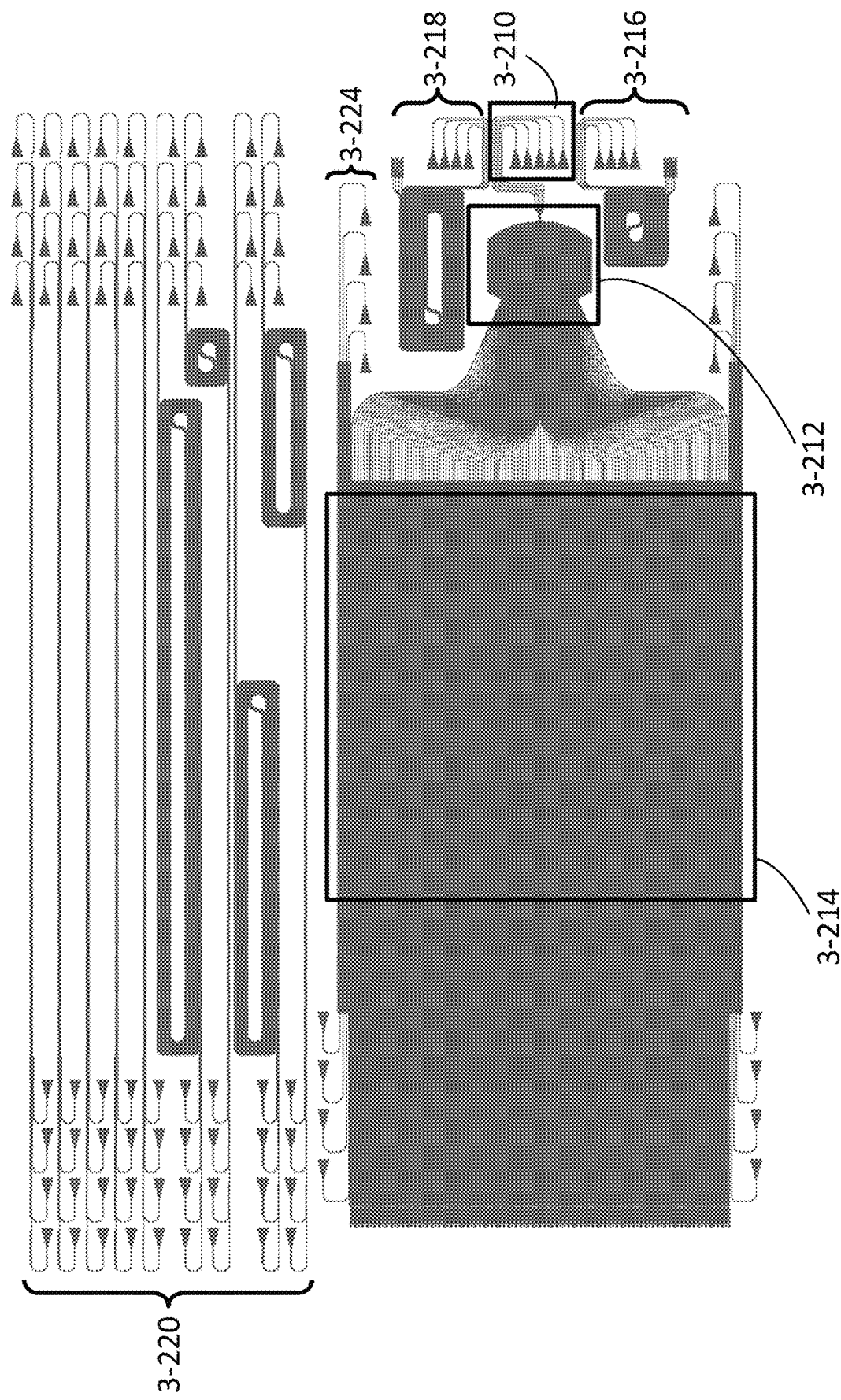
Figures 2C, 3:
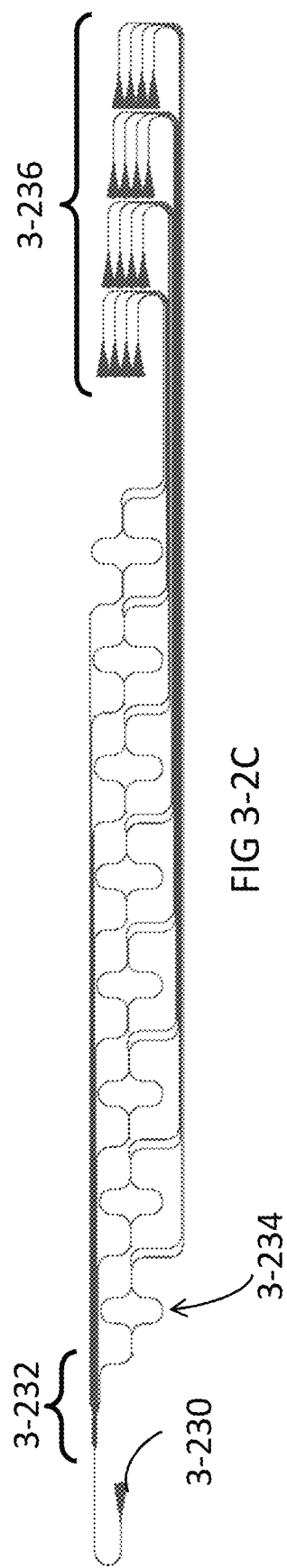
Figures 2D, 3:
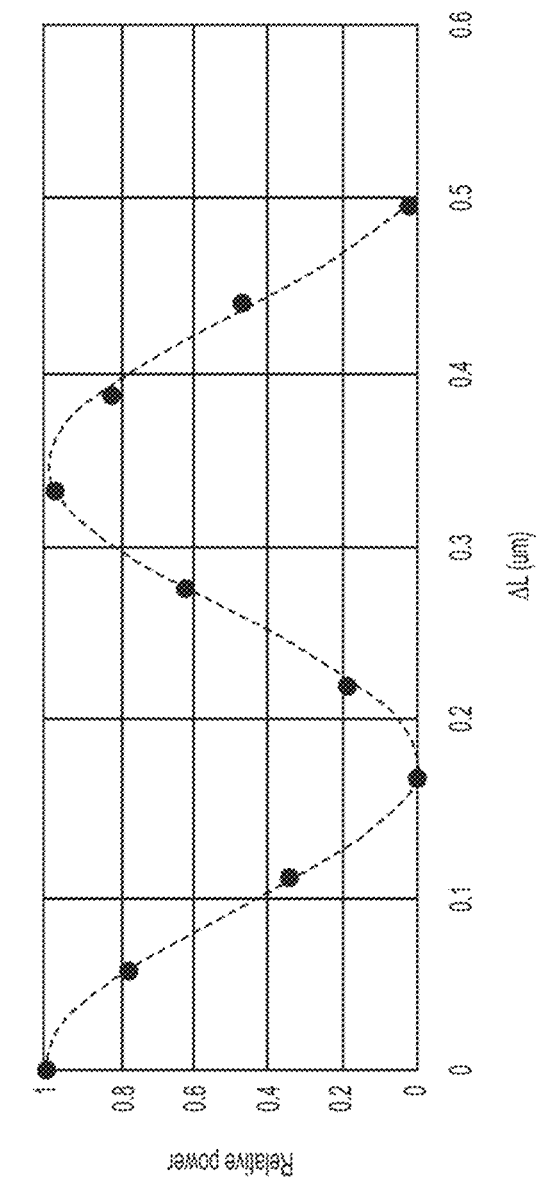

One type of photonic test structure of an integrated device may include multiple Mach-Zehnder Interferometers (MZIs), such as the test structure shown in FIG. 3-2C. The individual MZIs, including MZI 3-234, may have test arms with varying length and connect to the same MMI. As shown in FIG. 3-2C, MMI 3-232 may have one input to eight outputs, each output to a single MZI, although it should be appreciated that other combinations of MMIs and MZIs may be used in a test structure. This type of test structure may provide an indication for an effective value of the refractive index of the material used to form waveguides of the integrated device by aligning a light beam to input grating coupler 3-230 and measuring light detected by sensors positioned to receive light emitted from output grating couplers 3-236. A sensor pair may detect light from two individual output grating couplers 3-236 coupled to the same MZI. A comparison (e.g., difference, ratio) in the detected light between the two sensors may provide an indication of the relative power output of light for the two output grating couplers. The relative power may relate to the length of the test arm for the MZI and the effective index of refraction the waveguide. A value for the effective index of refraction of the waveguide may be determined by comparing the relative power to the length of the test arm for each individual MZIs. The relationship between relative power and test arm length may have a sinusoidal function where the period of the sinusoid is related to the effective refractive index. FIG. 3-2D is a plot of relative power as function of test structure length (indicated by $\Delta L$) for different MZIs included in a test structure, such as the test structure shown in FIG. 3-2C. By fitting data points to a sinusoidal function, the effective refractive index may be determined by identifying the period of the fitted sinusoidal curve. Such a test structure may also provide an indication of the uniformity and/or efficiency of MMI 3-232 in delivering a desired amount of light to each of the MZIs connected to MMI 3-232.

Figures 1, 2, 3, 3B:
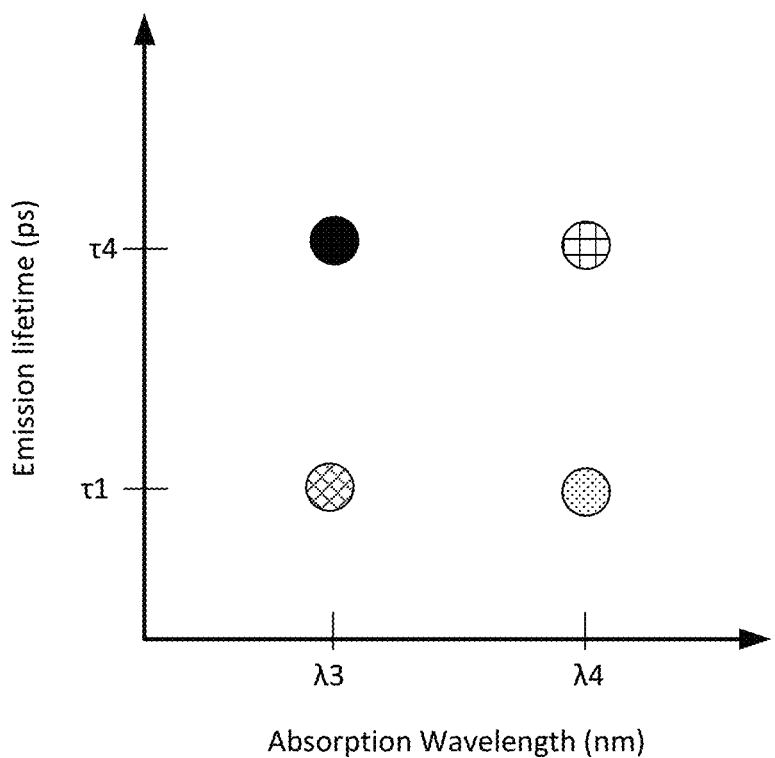
Figures 1, 2, 3, 4:
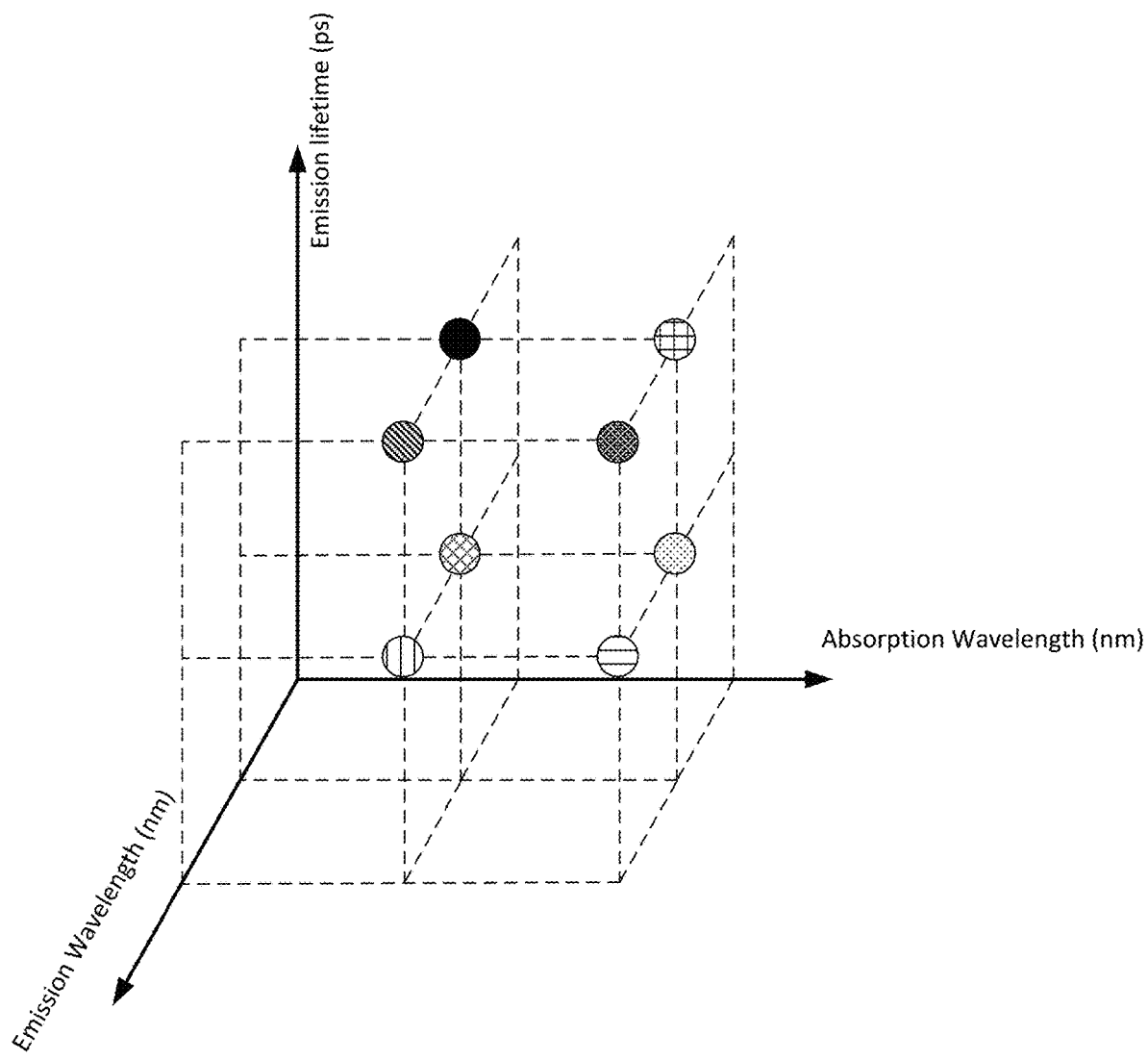

FIG. 4-1A illustrates schematically a cross-sectional view of integrated device 4-100, according to some non-limiting embodiments. Excitation energy may couple to grating coupler 4-114 and may travel along the propagation axis of waveguide 4-116 (for example from left to right of FIG. 4-1A along the x-axis). Waveguide 4-116 may support a mode of excitation energy that at least partially extends perpendicular to the propagation direction of waveguide 4-116. Such a mode may allow excitation energy to extend into top cladding 4-118 and evanescently couple to sample wells $4\text{-}108_1$, $4\text{-}108_2$, $4\text{-}108_3$, $4\text{-}108_4$, $4\text{-}108_5$, and $4\text{-}108_6$. Although only six sample wells are shown in FIG. 4-1A, any suitable number of sample wells may be positioned along a waveguide to evanescently couple with the waveguide. The number of sample wells positioned along a waveguide may be in the range of 100 to 5,000, or any value or range of values in that range. In some embodiments, the number of sample wells positioned along a waveguide may be in the range of 500 to 1,000, or any value or range of values in that range. A sample located in a sample well 4-108 may reach an excited state in response to being illuminated by the excitation energy and may emit emission energy. The shape and size of the sample well and/or the composition of metal layer 4-122 may act to direct emission energy towards a sensor. In some embodiments, a portion of the energy emitted by a sample in the form of emission energy may propagate downward through top cladding 4-118, waveguide layer 4-116, bottom cladding 4-110, and dielectric layer 4-102. A portion of the emission energy may be received by one or more sensors disposed on substrate 4-105 in a pixel associated with the sample well.

Integrated device 4-100 may comprise a lower stack 4-150, and an upper stack 4-151 disposed over lower stack 4-150. In some embodiments, upper stack 4-151 and lower stack 4-150 have an adjacent surface such that upper stack 4-151 and lower stack 4-150 are in contact with each other. In other embodiments, upper stack 4-151 and lower stack 4-150 are separated by one or more layers of materials.

Lower stack 4-150 may include components configured to provide an indication of the emission energy emitted from a sample located in a sample well of upper stack 4-151. Lower stack 4-150 may comprise substrate 4-105, which may include silicon in some embodiments. Substrate 4-105 may have any suitable height along the z-axis shown in FIG. 4-1A. By way of example and not limitation, substrate 4-105 may have a height between 0.001 mm and 0.01 mm in some embodiments, between 0.01 mm and 0.1 mm in some embodiments, between 0.1 mm and 1 mm in some embodiments. Substrate 4-105 may comprise sensors configured to detect emission energy emitted by one or more samples. Substrate 4-105 may also include sensors used to monitor excitation energy coupled to the integrated device. In some embodiments, one or more monitoring sensors positioned to overlap with grating coupler 4-114 may detect excitation energy that passes through grating coupler 4-114. Electrical signals from the sensors may provide an indication of the emission lifetime, intensity, and/or spectra. Substrate 4-105 may further comprise analog and/or digital electronic circuitry configured to read-out the electric signals provided by sensors. The electronic circuitry may comprise transistors, capacitors, amplifiers, switches, filters, integrators, timers, or any suitable combination thereof. Lower stack 4-150 may comprise dielectric layer 4-102. In some embodiments, dielectric layer 4-102 may be disposed on top of substrate 4-105. In some embodiments, dielectric layer 4-102 may comprise one or more dielectric sub-layers. The sub-layers be may be formed with any suitable dielectric that is at least partially transparent to emission energy, including silicon oxide, aluminum oxide, and titanium oxide.

In some embodiments, lower stack 4-150 may include one or more metal layers configured to act as electrical wiring within the integrated device. The metal layers may act as metal wires to route electrical signals within the integrated device and/or to circuitry located separate from the integrated device by coupling to the metal wires. The metal wires may be electrically coupled to substrate 4-105 through vias (e.g., tungsten vias). A metal layer may be disposed on or within a layer of material of the integrated device (e.g., dielectric layer). As shown in FIG. 4-1A, metal layers 4-103 and 4-104 are disposed within dielectric layer 4-102 and may act as metal wires within integrated device 4-100.

A metal layer of an integrated device may also act to reduce the amount of light that originates from sources other than samples located in sample wells of the array. In this manner, a metal layer may be considered a baffle. Such metal layers may improve the signal-to-noise ratio of the sensors by reducing noise artifacts that can arise from stray light (e.g., excitation light, background light). The metal layers may be positioned relative to the sample wells to allow for detection of emission energy. As shown in FIG. 4-1A, metal layers 4-103 and 4-104 are non-overlapping with sample wells 4-108$_k$, 4-108$_2$, 4-108$_3$, 4-108$_4$, 4-108$_5$, and 4-108$_6$. Metal layer 4-103 is positioned between substrate 4-105 and grating coupler 4-114 and may act to reduce the amount of excitation energy that passes through grating coupler 4-114 from reaching substrate 4-105 and/or a sensor of substrate 4-105. Metal layer 4-104 is positioned between a distal end of waveguide 4-116 and substrate 4-105 and may act to reduce excitation energy emitted from the distal end of waveguide 4-116 from reaching substrate 4-105 and/or a sensor of substrate 4-105.

Metal layers 4-103 and 4-104 may be formed of any suitable metal, such as aluminum in some embodiments. In some embodiments, a metal layer may include more than one metal. Materials used to form a metal layer may provide a desired level of adhesion with one or more surrounding materials of an integrated device. In some embodiments, a liner layer may be formed in contact with a metal layer and may improve adhesion of the metal layer with another component of integrated device 4-100. The liner layer may act as an adhesion layer between a metal layer and dielectric layer 4-102. Examples of suitable materials to be used as a liner layer include titanium and titanium nitride. In some embodiments, a liner layer may be formed on a surface of a metal layer proximate to the substrate of the integrated device. In some embodiments, a liner layer may be formed on a surface of a metal layer proximate to the surface of the integrated device that has the sample wells.

In some embodiments, an integrated device may comprise two or more metal layers that at least partially overlap in the integrated device (not shown in FIG. 4-1A). Any suitable number of over-lapping metal layers (e.g., 2, 3, 4, 5) may be used. Adjacent metal layers may be electrically connected through one or more vias (e.g., tungsten vias).

Upper stack 4-151 may include sample wells in the array and optical components configured to receive excitation energy from and external light source separate from integrated device 4-100 and direct excitation energy towards one or more of the sample wells. Upper stack 4-151 may include bottom cladding 4-110, which may be disposed on top of dielectric layer 4-102. Materials used to form bottom cladding 4-110 may have a desired level of transparency to light (e.g., emission energy, excitation energy). Bottom cladding 4-110 may be formed of any suitable dielectric material, such as silicon oxide, aluminum oxide, or titanium oxide, for example. In some embodiments, dielectric layer 4-102 and bottom cladding 4-110 may comprise the same dielectric materials, and may form a single dielectric stack. In other embodiments, dielectric layer 4-102 and bottom cladding 4-110 may comprise different dielectric materials.

Upper stack 4-151 may include one or more waveguides configured to propagate excitation energy having one or more characteristic wavelengths. Waveguide 4-116 may be formed by patterning a layer of material as part of upper stack 4-151 using suitable fabrication techniques (e.g., photolithography). Waveguide 4-116 may be formed of one or more materials having a refractive index larger than the refractive index of bottom cladding 4-110. Example materials used to form waveguide 4-116 include silicon and silicon nitride ($Si_xN_y$).

Waveguide 4-116 may have a width (defined along an axis perpendicular to the plane of FIG. 4-1A) and a height (defined along the z-axis) such that only a single mode may be defined within waveguide 4-116. In some embodiments, the single mode may be a transverse electric (TE) mode. In other embodiments, the single mode may be a traverse magnetic (TM) mode. Waveguide 4-116 may have a height that is in the range of 80 nm to 250 nm, or any value or range of values within that range. In some embodiments, waveguide 4-116 has a height in the range of 120 nm to 150 nm, or any value or range of values in that range. Waveguide 4-116 may have a width that is in the range of 200 nm to 1600 nm, or any value or range of values within that range. In some embodiments, the width of waveguide 4-116 may be tapered along its propagation axis such that waveguide 4-116 has a larger width proximate to grating coupler 4-114 than at a location distal from grating coupler 4-114. Accordingly, the waveguide may be configured to have increasing coupling coefficients to the various sample wells as the mode propagates away from the input grating coupler. In some embodiments, the width of waveguide 4-116 may be tapered linearly. Having a tapered waveguide may allow for a more uniform coupling of excitation energy to various sample wells 4-108 positioned to couple with the waveguide than if the waveguide lacked the taper configuration.

Upper stack 4-151 may include grating coupler 4-114 configured to receive excitation energy from an excitation source and optically couple excitation energy to waveguide 4-116. In some embodiments, grating coupler 4-114 may be formed from the same material (e.g., silicon, silicon nitride) as waveguide 4-116. During formation of the integrated device, the same photolithographic process step may form both grating coupler 4-116 and waveguide 4-116. Grating coupler 4-114 may be configured to receive an optical beam that is normally incident (along the z-direction shown in FIG. 4-1A) to the plane of grating coupler 4-114. In some embodiments, grating coupler 4-114 may be configured to receive an optical beam incident at an angle from the normal to the plane of grating coupler 4-114 (along the z-direction shown in FIG. 4-1A). Such an angle may be between 0.1° and 10°, or any value or range of values within that range. The coupling efficiency of grating coupler 4-114 may depend on the relative positioning of reflector 4-112 to grating coupler 4-114. In some embodiments, grating coupler 4-114 may have a coupling efficiency in the range of 40% to 70%, or any value or range of values within that range. FIG. 4-4 shows an exemplary structure for a grating coupler, such as grating coupler 4-114, a cavity region which couples to a waveguide. A grating coupler may have a radius of $R_g$ of the first grating and proximate a side of a cavity region having a width, $W_c$, along the y-direction. The cavity region may have a taper length along the x-direction of $L_c$. The cavity may have a region with a radius taper. As shown in FIG. 4-4, the cavity has region 4-404 with a radius taper between widths $W_e$ and $W_o$ of the cavity. Width $W_o$ may correspond to where the cavity outputs to a waveguide. The cavity may have a region with an adiabatic taper. As shown in FIG. 4-4, the cavity has region 4-402 with an adiabatic taper region between widths $W_g$ and $W_o$ of the cavity having a length along the x-direction of $L_t$. At width $W_g$, the dimensions of the cavity may correspond to a waveguide.

One or more monitoring sensors positioned proximate to grating coupler 4-114 may detect excitation energy that passes through a plane of grating coupler 4-114 without coupling to grating coupler 4-114. Electrical signals from the one or more monitoring sensors may provide an indication of alignment of excitation energy from the excitation source to the integrated device. In some embodiments, the one or more monitoring sensors are positioned to receive excitation energy that passes through a plane of grating coupler 4-114 but in a region separate from grating coupler 4-114. In some embodiments, a reflector positioned between grating coupler 4-114 and the one or more monitoring sensors may have one or more openings that allow for excitation energy to pass through the reflector. The one or more openings of the reflector may be positioned relative to grating coupler 4-114 such that grating coupler 4-114 is non-overlapping with the one or more openings of the reflector. In some embodiments, the one or more openings of the reflector are position proximate to the perimeter of grating coupler 4-114.

Integrated device 4-100 may include reflector 4-112 positioned to overlap, at least partially, with grating coupler 4-114 along the z-axis. Reflector 4-112 may improve coupling efficiency of grating coupler by reflecting at least a portion of the light that passes through grating coupler 4-114 back towards grating coupler 4-114, which may enhance the amount of light that couples to grating coupler 4-114 than if reflector 4-112 were not present. Reflector 4-112 may be formed using a material that reflects, at least partially, the excitation energy. Examples of suitable materials to be used as a reflector include aluminum and copper. In some embodiments, reflector 4-112 may comprise aluminum, and the aluminum layer may be in direct contact with bottom cladding 4-110.

The coupling efficiency of grating coupler 4-114 may depend on the degree to which the phase of the incident light differs from the phase of the reflected light from reflector 4-112. Coupling efficiency of grating coupler 4-114 may be improved where the phase of the incident light approximately aligns with the phase of the reflected light. The phase of the reflected light that combines with the incident excitation energy may depend on the optical path length between grating coupler 4-114 and reflector 4-112. Accordingly, some embodiments relate to an integrated device where distance $h_R$ between grating coupler 4-114 and reflector 4-112 provides an optical path length that reduces phase mismatch between light that passes through grating coupler 4-114 and is reflected by reflector 4-112 and the mode of light supported by grating coupler 4-114. To provide a suitable amount of phase matching between reflected light and incident light to grating coupler 4-114, the desired distance $h_R$ may depend on the refractive index of the material used to form bottom cladding 4-110 and/or the characteristic wavelength of the excitation energy. In some embodiments, $h_R$ may have a length such that an optical beam from grating coupler 4-114 and reflected by reflector 4-112 to grating coupler 4-114 is approximately in phase with the mode of grating coupler 4-114. In some embodiments, the phase accumulation experienced by a beam propagating from the plane of grating coupler 4-114, being reflected back by reflector 4-112, propagating towards the plane of grating coupler 4-114 may be approximately equal to or within a range of $2\pi$ (e.g., within a range of 5% of $2\pi$). Distance $h_R$ may be in the range of 400 nm to 1200 nm, or any value or range of values within that range. In some embodiments, distance $h_R$ may be approximately 1100 nm. In other embodiments, distance $h_R$ may be approximately 550 nm.

Reflector 4-112 may have a plurality of openings formed thereon (not shown). The openings may have circular shapes, elliptical shapes, rectangular shapes, square shapes, or any other suitable shape. The openings may have any suitable size. The openings may be formed during the same lithographic step by which reflector 4-112 is formed. For example, reflector 4-112 may be formed through a photomask having a shape corresponding to reflector 4-112, such that the shape may have openings formed thereon. The openings may be configured to allow a portion of the excitation energy propagating towards reflector 4-112 (approximately along the z-direction) to pass through reflector 4-112.

One or more monitoring sensors positioned to overlap with the openings of reflector 4-112 may receive excitation energy that passes through reflector 4-112 and generate an electrical signal corresponding to an amount of the excitation energy received. The measurements of the excitation energy by the monitor sensors may be used to align the incident radiation of the excitation energy to grating coupler 4-114 to achieve a desired level of power of excitation energy coupled into waveguide 4-116. In some embodiments, an operator may adjust, manually through knobs or electronically through actuators and motors coupled to optical components used to direct excitation energy from the excitation source, the amount of energy detected by a monitor sensor. In some embodiments, alignment of the excitation energy to grating coupler 4-114 may include identifying an orientation of an optical beam of excitation energy to grating coupler 4-114 where the amount of photons detected by individual monitor sensors is approximately the same. Any suitable number of monitor sensors may be included in an integrated device and used for alignment of the excitation source to the grating coupler of the integrated device. In some embodiments, the integrated device may include four monitor sensors arranged to form four quadrants, which may be referred to as a "quadrant" detector. The four monitor sensors may each individually overlap with an opening through reflector 4-112. Examples of suitable alignment mechanisms for aligning an excitation source to a grating coupler are described in U.S. Pat. Application 62/310,398 entitled "PULSED LASER AND SYSTEM," which is incorporated by reference in its entirety.

In some embodiments, alignment of an optical beam of excitation energy to grating coupler 4-114 may include measuring light detected by one or more additional sensors including one or more output sensors positioned to receive excitation energy coupled from an end of a waveguide distal from the excitation energy coupling region and/or one or more sensors associated with pixels of the integrated device. Alignment of the optical beam may include positioning the beam relative to grating coupler 4-114 such that a desired level of excitation energy is detected by one or more output sensors and/or one or more pixel sensors.

In some embodiments, alignment of the optical beam is achieved when a measurement by at least one output sensor and/or at least one pixel sensor provides an indication that the amount of excitation energy has increased from a different positioning of the optical beam. An alignment process may include positioning the beam at different orientations (e.g., angle of beam to grating coupler 4-114, incident beam locations on grating coupler 4-114) and detecting light by at least one output sensor and/or at least pixel sensor for the different orientations. A beam orientation may be identified as an alignment position for the optical beam by measurements indicating the detected light. In some embodiments, a beam orientation can be identified as an alignment position when a measurement of detected light by at least one output sensor and/or at least one pixel sensor is the maximum at that orientation relative to other beam orientations.

Once an alignment position of the optical beam is identified, measurements by the one or more monitoring sensors may provide an indication of whether the beam orientation varies from an initial alignment position. The measurements may provide information about how to correct for such a misalignment. Realignment of the optical beam may include positioning the beam such that measurements of excitation energy by the one or more monitoring sensors are approximately similar to the measurements associated with the initial alignment position. In this manner, the one or more monitoring sensors may provide information as part of a feedback process for maintaining alignment of the optical beam after an initial alignment has been achieved. The feedback process may be used during operation of the integrated device to improve stability of the measurements performed on a sample.

Integrated device 4-100 may include top cladding 4-118 formed over waveguide 4-116. Top cladding 4-118 may include a dielectric material having a refractive index lower than the refractive index of a material of waveguide 4-116. In some embodiments, top cladding 4-118 may comprise one or more sub-layers having a desired level of transparence to excitation energy and emission energy. Examples of suitable materials used to form top cladding 4-118 include silicon oxide, aluminum oxide, and titanium oxide. The desired level of transparency may be in the range of 50% to 100% or any value or range of values within that range.

Top cladding 4-118 may have a varying dimension in a direction perpendicular to waveguide 4-116 and parallel to the thickness of upper stack 4-151. As shown in FIG. 4-1A, top cladding 4-118 has a varying dimension along the z-axis that is smaller in a region that at least partially overlaps with the grating coupler 4-114 and in a region that at least partially overlaps with sample wells 4-108 than other regions of the integrated device. Such a region where the dimension of top cladding 4-118 is recessed from other areas of the integrated device may be considered as a trench region. The variation of top cladding 4-118 along the z-direction may allow for improved optical performance of integrated device 4-100 by having a larger thickness in some regions to reduce the amount of excitation energy scattered or absorbed by metal layer 4-122 and a smaller thickness in regions where excitation energy couples with surface 4-124, including excitation energy coupling region 4-115 and trench region 4-120 having sample wells 4-108. The variation in thickness of top cladding 4-118 may provide a larger distance between waveguide 4-116 and the interface between metal layer 4-122 and top cladding 4-118 for some regions along waveguide 4-116, which may reduce optical loss over those regions.

Top cladding 4-118 may have a dimension along the z-direction corresponding to distance $h_C$ in at least one region separate from one or more sample wells 4-108. A region of top cladding 4-118 having dimension $h_C$ may be located to not overlap with a sample well 4-108. Dimension $h_C$ may correspond to a distance between the top of waveguide 4-116 and the top surface of top cladding 4-118. Dimension $h_C$ may have a suitable value to reduce optical loss of light propagating along waveguide 4-116. In embodiments of the integrated device that include metal layer 4-122 over top cladding 4-118, dimension $h_C$ may reduce optical loss that arises from optical loss due to metal layer 4-122. Dimension $h_C$ may be in the range of 200 nm to 2000 nm, or any value or range of values within that range. In some embodiments, dimension $h_C$ may be in the range of 400 nm to 2000 nm, or any value or range of values within that range. In some embodiments, dimension $h_C$ may be in the range 250 nm to 2000 nm, or any value or range of values within that range.

Some embodiments relate to an integrated device that includes an excitation energy coupling region 4-115 of top cladding 4-118 positioned to overlap, at least partially, with grating coupler 4-114. Excitation energy coupling region 4-115 may have a dimension $h_G$ along the z-direction between surface 4-124 of integrated device 4-100 and a surface of grating coupler 4-114 proximate to surface 4-124. Dimension $h_G$ may have a value less than dimension $h_e$ of top cladding 4-118. Excitation energy coupling region 4-115 may be formed by partially etching top cladding 4-118. The dimension $h_G$ of excitation energy coupling region 4-115 may provide a desired level of coupling efficiency for a characteristic wavelength of excitation energy (e.g., 532 nm). Accordingly, a suitable dimension $h_G$ may vary depending on the characteristic wavelength of excitation energy used as an excitation source. Dimension $h_G$ may be in the range of 200 nm to 800 nm, or any value or range of values within that range. In embodiments where the characteristic wavelength of excitation energy is 532 nm, dimension $h_G$ is in the range of 250 nm to 350 nm.

Dimensions $h_G$ and $h_R$ may impact the grating coupler's coupling efficiency in directing excitation energy from an external source to one or more waveguides of an integrated device. A fabrication process used to form an integrated device may form top cladding 4-118 and/or bottom cladding 4-110 to have a dimension within a window of values for a target value used during the fabrication process. Such variation in the dimension of top cladding 4-118 and/or bottom cladding 4-110 introduced by the fabrication process may create variations in the coupling efficiency across multiple integrated devices. Applicants have recognized that some dimensions of $h_G$ and/or $h_R$ may broaden the range of suitable dimensions of top cladding 4-118 and/or bottom cladding 4-110 for achieving a desired level of coupling efficiency for the grating coupler. Accordingly, some aspects of the present application relate to fabrication techniques that use target values for dimensions $h_G$ and/or $h_R$ that may provide a degree of tolerance for deviation from dimension $h_G$ and/or $h_R$ in the resulting device to reduce the impact of the deviation on the grating coupler's coupling efficiency. In some instances, the fabrication process used to form excitation coupling region 4-115 of top cladding 4-118 may provide a more accurate dimension $h_G$ for top cladding 4-118 than the fabrication process used to form dimension $h_R$ of bottom cladding 4-110. In some embodiments, dimension $h_R$ may vary by approximately 10% across different integrated devices formed using the same fabrication process. Suitable target values for dimension $h_G$ may be selected based on their ability to provide a broad range of values for dimension $h_R$ such that the combination of dimension $h_G$ and dimension $h_R$ provides a desired coupling efficiency for grating coupler 4-114 that accounts for variation in dimensions that may arise during fabrication.

Figures 1A, 4:
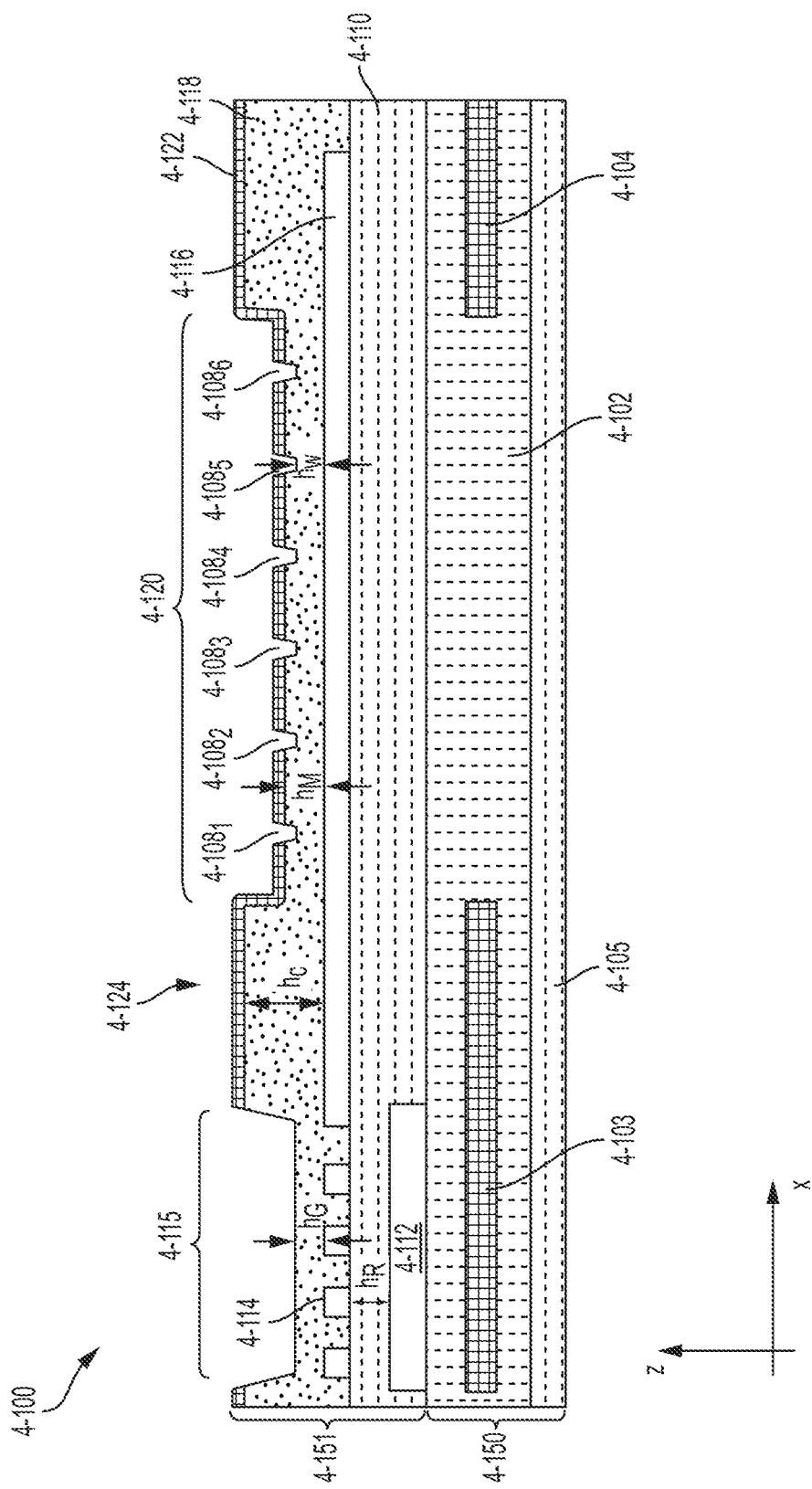
Figures 1B, 4:
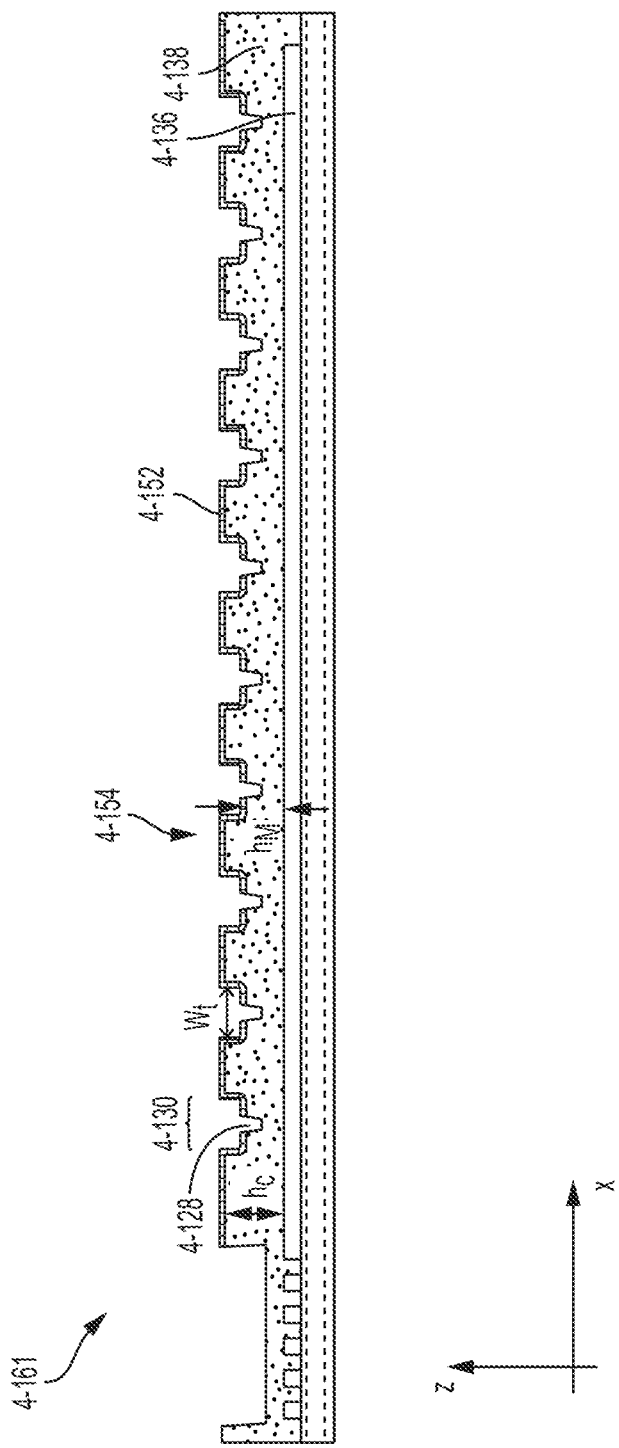
Figures 2, 4:
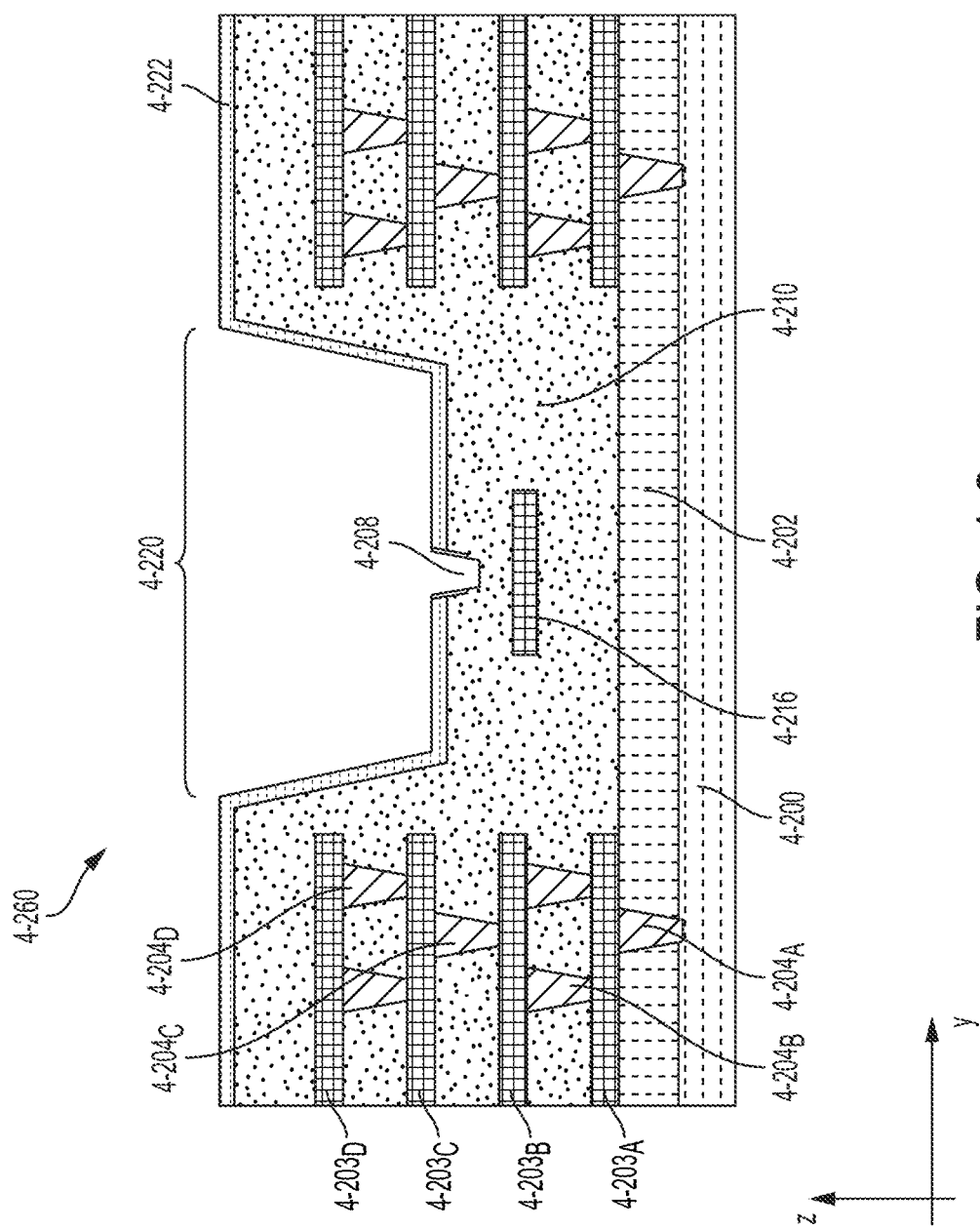
Figures 3, 4:
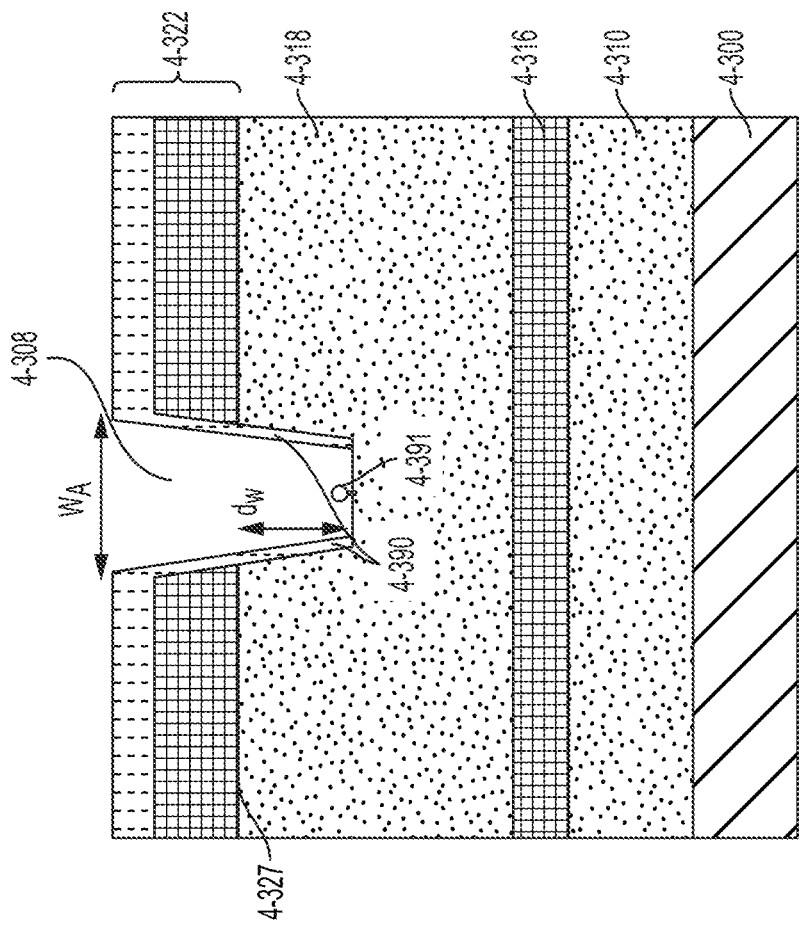
Figure 4:
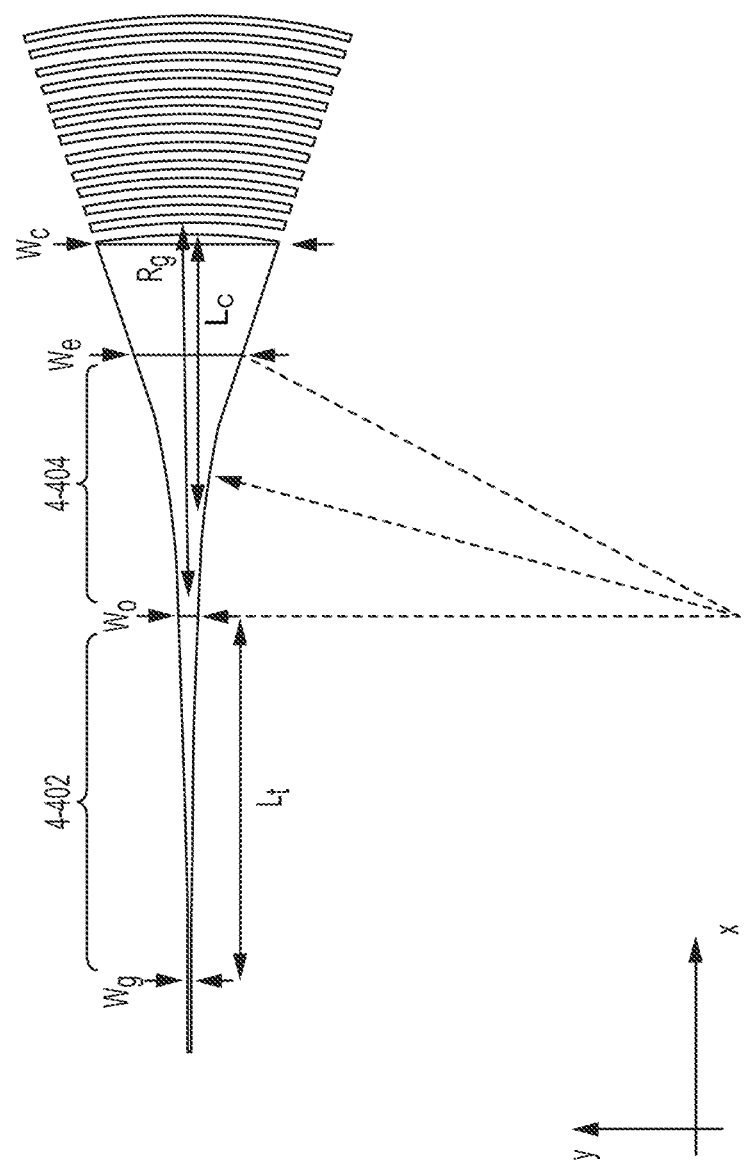
Figures 4, 5:
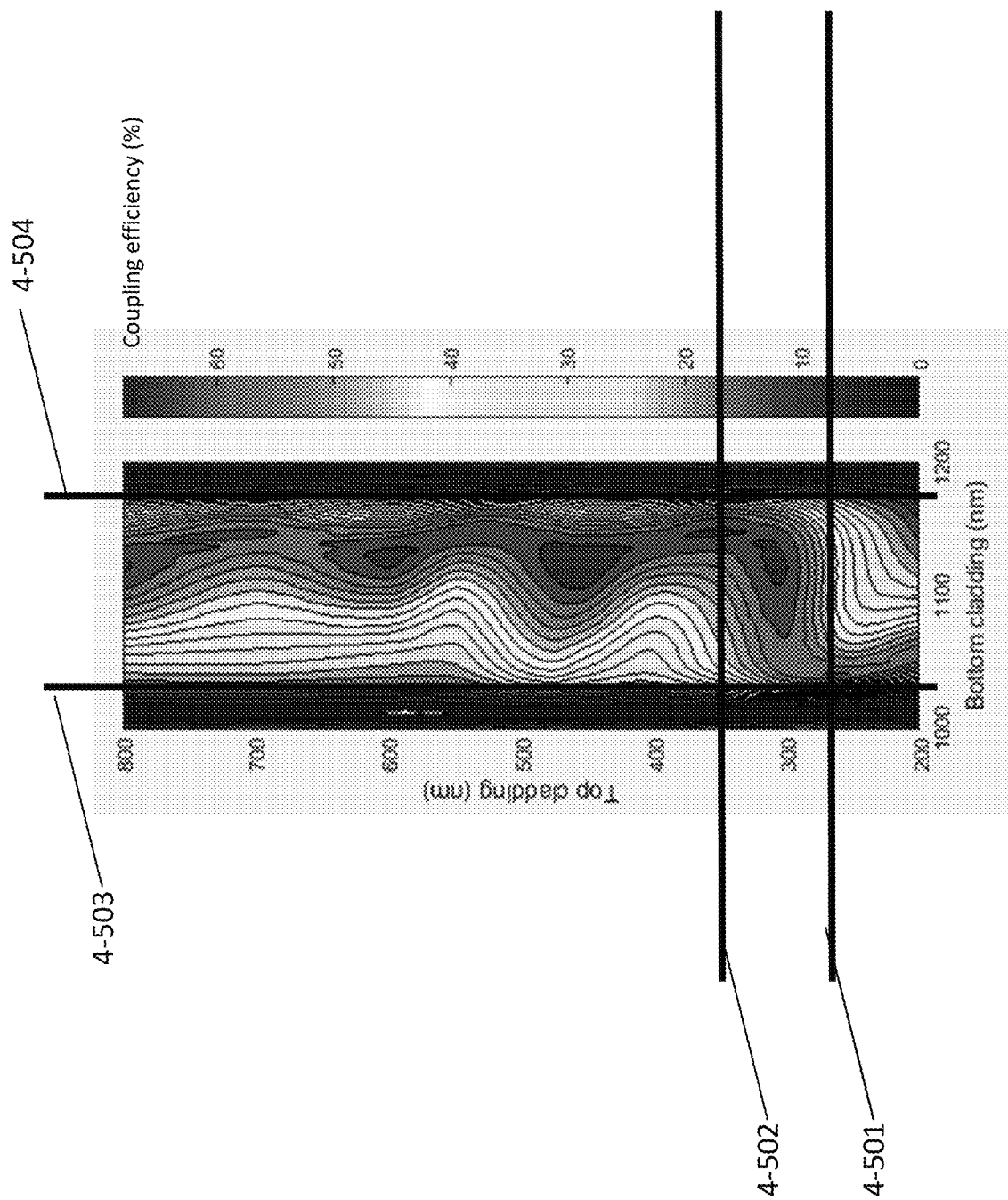

FIG. 4-5 is a plot (black and white conversion of a color heat map) illustrating the grating coupler's coupling efficiency, as a percentage, for different values of top cladding dimension $h_G$ (y-axis) and bottom cladding dimension $h_R$ (x-axis) and a wavelength of 532 nm. The darker regions of the plot between lines 4-503 and 4-504 depict combinations of dimensions $h_G$ and $h_R$ where the grating coupler has a coupling efficiency of at least 50%. FIG. 4-5 provides an indication of dimensions for bottom cladding and/or top cladding that provide a degree of tolerance during the fabrication process of an integrated device. In embodiments where the dimension $h_G$ of the top cladding may be more accurately fabricated than the dimension $h_R$ of the bottom cladding, a target value for dimension $h_G$ may be selected so as to provide a suitable fabrication tolerance for the resulting dimension $h_R$. As shown in FIG. 4-5 values for dimension $h_G$ of the top cladding within lines 4-501 and 4-502 provide a broad range of values for dimension $h_R$ that form a grating coupler of approximately 50% coupling efficiency. Selecting a target value for dimension $h_G$ within lines 4-501 and 4-502 may account for tolerances of the fabrication process of bottom cladding. In some embodiments, fabrication of an integrated device may include a target value for dimension $h_G$ within the range defined by lines 4-501 and 4-502 and a target value for dimension $h_R$ within the range defined by lines 4-503 and 4-504. Dimension $h_G$ may have a value in the range of 250 nm to 350 nm, or any value or range of values within that range. Dimension $h_R$ may have a value in the range of 1025 nm to 1175 nm, or any value or range of values within that range. In some embodiments, a target value for dimension $h_G$ is approximately 300 nm and a target value for dimension $h_R$ is approximately 1100 nm during fabrication of an integrated device.

A grating coupler may couple to one or more splitter structures to provide approximately uniform power distribution across the array of sample wells. Some embodiments relate to an integrated device that has a splitter structure configured to receive input excitation energy and direct the excitation energy into individual waveguides. The splitter structure may have a configuration that provides approximately uniform distribution of excitation energy among the individual output waveguides. In some embodiments, the splitter structure may have a configuration that reduces the area they occupy on the integrated device to provide an integrated device having a desired size and shape.

Figures 4, 5, 6:
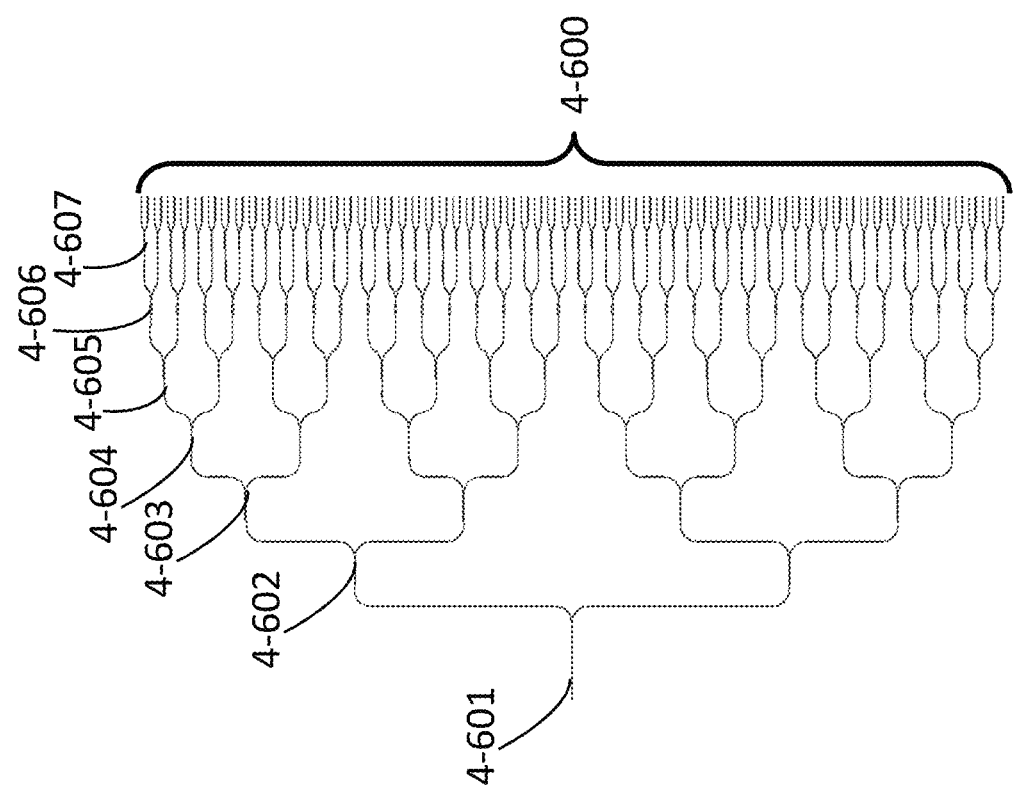

In some embodiments, an integrated device may have a splitter structure that includes multiple MMIs having a cascaded configuration. The splitter structure may include multiple MMIs that have one input to two outputs arranged to have seven cascaded levels to provide a desired power division from a single input to 128 outputs of the splitter structure. As shown in FIG. 4-6, a splitter structure having a series of cascaded MMIs may include first-level MMI 4-601 that receives input light and splits the light to two outputs, including an output that couples as an input to second-level MMI 4-602. An output of second-level MMI 4-602 may couple as an input to third-level MMI 4-603. An output of third-level MMI 4-603 may couple as an input to fourth-level MMI 4-604. An output of fourth-level MMI 4-604 may couple as an input to fifth-level MMI 4-605. An output of fifth-level MMI 4-605 may couple as an input to sixth-level MMI 4-606. An output of sixth-level MMI 4-606 may couple as an input to seventh-level MMI 4-607. Outputs 4-600 from the seventh-level MMIs, including seventh level MMI 4-607, may each couple to waveguides configured to direct excitation energy to multiple sample wells of the integrated device. An MMI having one input to two outputs may have a power efficiency of approximately 98%. A structure having cascaded MMIs, such as the structure shown in FIG. 4-6 that has seven levels of MMI structures, may have a total efficiency of approximately 87%. In some embodiments, the variation of power output across the different outputs of a cascaded MMI structure may be in the range of 2% to 20%, or any value or range of values within that range.

MMIs of a cascaded MMI splitter structure may have any suitable number of inputs and/or outputs to provide a desired number of levels for the MMI cascaded splitter. FIG. 4-7A is a schematic of a splitter structure having three levels of cascaded MMIs. At least one of grating couplers 4-700 may be configured to direct excitation energy from an incident beam of excitation energy to first-level MMI 4-701, which has a structure having four inputs and four outputs. FIG. 4-7B is an exemplary MMI having a four input 4-708 by four output 4-406 structure that may be used as first-level MMI 4-701. This MMI design provides multiple inputs that can equivalently couple excitation energy to subsequent MMI structures. Multiple grating couplers 4-700 may provide redundancy in the number of inputs for excitation energy to couple with the integrated device. While only one of the grating couplers may be used during operation of the integrated device to analyze a sample, a grating coupler from among the multiple grating couplers 4-700 may be selected for use during operation based on a performance level for each of the multiple grating couplers 4-700. Each of the outputs from first-level MMI 4-701 may couple with a second-level MMI including second-level MMI which has a one input by eight output configuration. Each output from a second-level MMI couples to a third-level MMI including third-level MMI 4-703 which has a one input by four output configuration. Outputs 4-704 from each of the third-level MMIs may couple to waveguides configured to couple excitation energy to individual sample wells of the integrated device.

Efficiency and uniformity of power division across multiple waveguides may depend on the thickness and/or refractive index of the material (e.g., silicon nitride) used to form the splitter structure and refractive index of the cladding material surrounding the splitter structure (e.g., silicon oxide). FIG. 4-7C shows an exemplary MMI structure having an input waveguide with width $WGbus_{in}$ which increases to width $WG_{in}$ to couple into a cavity of the MMI having $W_{MMI}$. The MMI structure shown in FIG. 4-7C has four output waveguides, each positioned relative to a center line of the MMI cavity. The output waveguides have an output width of $WG_{out}$ which decreases to $WGbus_{out}$. As shown in FIG. 4-7C, an outer waveguide is positioned at position P2 relative to the center line of the MMI cavity and an inner waveguide is positioned at position P1 relative to the center line of the MMI cavity.

In some embodiments, an integrated device may have a splitter structure that includes a star coupler configuration. The star coupler may have an input configured to couple with at least one input grating coupler and outputs configured to provide approximately uniform power distribution across the individual outputs. In some embodiments, a star coupler may have outputs having varying widths across the individual outputs to provide approximately uniform power distribution across the outputs. FIG. 4-8A is a schematic of an exemplary star coupler having input grating couplers 4-800 configured to receive light from an incident beam directed away from outputs 4-804 positioned at an opposite side to grating couplers 4-800. FIG. 4-8B is a zoomed-in schematic of the portion of the star coupler shown in region 4-802. Propagation region 4-806 receives input light and directs light to outputs 4-804. Divergence within propagation region 4-806 may depend on the thickness of the propagation region and refractive index of the material used to form the star coupler and/or cladding surrounding the star coupler. The size and shape of the input waveguide may also impact the level of divergence provided by propagation region 4-806. Outputs 4-804 may vary in width, which is a dimension in the plane shown in FIGS. 4-8A and 4-8B and perpendicular to the direction of light propagation along an output. Variation in the width of the individual waveguide outputs may provide approximately uniform power distribution across the individual outputs 4-804. A dimension between adjacent outputs 4-804 may be in the range of 100 nm to 200 nm, or any value or range of values within that range.

In some embodiments, a star coupler may have outputs positioned at varying radial distances from an input of the star coupler. Such a configuration may provide outputs having approximately uniform widths, which may reduce the amount of space needed to form the splitter structure and accommodate space constraints for the integrated device. FIG. 4-9A is a schematic of an exemplary star coupler having at least one input 4-904 coupled to a propagation region with outputs opposite to the at least one input 4-904. FIG. 4-9B is a zoomed view of the region of 4-900 and FIG. 4-9C is a zoomed view of region 4-902. Region 4-900 shows the arrangement of outputs from the propagation region at a closer radial distance to input 4-904 than the outputs shown in region 4-902.

In some embodiments, a star coupler may include a grating coupler embedded within a propagation region of the star coupler where the grating coupler may act as an input for an incident beam of excitation energy. The grating coupler may be curved, linear, or have any suitable shape or size to provide a desired level of coupling efficiency with star coupler. FIG. 4-10 is a schematic of an exemplary star coupler having input grating coupler 4-1000 positioned within propagation region 4-1004 which is coupled to outputs 4-1002.

In some embodiments, the grating coupler may be configured to receive two different characteristic wavelengths of excitation energy. In some embodiments, a star coupler may have two different grating couplers within a propagation region where each of the grating couplers is configured to receive a different characteristic wavelength of excitation energy.

In some embodiments, an integrated device may include a splitter structure configured as a sliced grating coupler configured to provide power distribution across multiple output waveguides from an input beam having a non-circular (e.g., elongated Gaussian profiles) cross-sectional area. FIG. 4-11 is a schematic of a splitter structure having sliced grating coupler 4-1100 configured to couple with outputs 4-1102. Sliced grating coupler 4-1100 may be configured to receive an input light having a Gaussian cross-sectional profile and provide approximately uniform power distribution across the individual outputs 4-1102. Individual slices may have varying width (along the y-direction) proximate to sliced grating coupler 4-1100 to improve the uniformity of power across the different outputs 4-1102. The width of individual slices may gradually taper to form uniform or approximately uniform width across all outputs 4-1102 in a region that overlaps with at least a portion of the pixel array of the integrated device. As shown in FIG. 4-11, width variation across slices may include outer slices 4-1104 having a larger width proximate to grating coupler 4-1100 than one or more inner slices 4-1106. In some embodiments the input beam intensity is approximately uniform along the length of the grating, in which case the individual slice widths are approximately similar.

Top cladding may have one or more regions that have a dimension less than distance $h_C$ and includes one or more sample wells. Such a region may be considered a trench region of suitable size and shape to include one or more sample wells of the integrated device. As shown in FIG. 4-1A, integrated device 4-100 includes trench region 4-120 where top cladding 4-118 has a dimension $h_M$ along the z-direction that is less than $h_C$. A value for dimension $h_M$ may balance proximity of one or more sample wells to waveguide 4-116 and optical loss that may arise from the proximity of metal layer 4-122 to waveguide 4-116. Optical loss of excitation energy propagating along waveguide 4-124 may arise from scattering and/or absorption with a surface of metal layer 4-122 proximate to waveguide 4-124. Accordingly, dimension $h_M$ may impact the uniformity of excitation energy to sample wells $4\text{-}108_1$, $4\text{-}108_2$, $4\text{-}108_3$, $4\text{-}108_4$, $4\text{-}108_5$, and $4\text{-}108_6$ positioned to couple with a waveguide 4-116. Dimension $h_M$ may have a value in the range of 150 nm to 600 nm, or any value or range of values within that range. In some embodiments, dimension $h_M$ may be approximately 400 nm. In some embodiments, dimension $h_M$ may have a value in the range of 300 nm to 600 nm, or any value or range of values within that range. In some embodiments, dimension $h_M$ may have a value in the range of 150 nm to 450 nm.

Trench region 4-120 may have an area in a plane perpendicular to the view shown in FIG. 4-1A of any suitable size and shape to include a desired number of sample wells. In some embodiments, trench 4-120 may have a rectangular shape (e.g., square). Trench 4-120 may have a plurality of sample wells, including sample wells $4\text{-}108_1$, $4\text{-}108_2$, $4\text{-}108_3$, $4\text{-}108_4$, $4\text{-}108_5$, and $4\text{-}108_6$. While FIG. 4-1A illustrates six sample wells, the application is not limited in this respect and any suitable number of sample wells may be formed in a trench region.

A trench region may include one or more sample wells where a surface of one of the sample wells may be positioned a distance $h_W$ from waveguide 4-116. Dimension $h_W$ between a sample well 4-108 of integrated device 4-100 and waveguide 4-116 may provide a desired level of coupling as excitation energy propagates along waveguide 4-116. Dimension $h_W$ may allow for excitation energy to evanescently couple to sample well 4-108. In this manner, dimension $h_W$ may impact the amount of excitation energy delivered to one or more sample wells of integrated device 4-100. Dimension $h_W$ may be in the range of 0 nm to 400 nm, or any value or range of values within that range. In some embodiments, $h_W$ is approximately 300 nm. In some embodiments, dimension $h_W$ is in the range 0 nm to 300 nm. In some embodiments, dimension $h_W$ is in the range 0 nm to 100 nm.

The optical path length between a sensor and a sample well in a pixel of an integrated device may impact the ability of the sensor to detect a photon emitted from the sample well. By shortening the optical path length between the sample well and the sensor, the numerical aperture may increase and improve the collection of emission energy emitted from a sample in the sample well. The dimension $h_W$ may also impact the directionality of emission energy in a pixel. A value of dimension $h_W$ may allow a sensor of the integrated device to detect a desired level of power of emission energy. In some embodiments, the distance between a sample well and a sensor in a pixel may be in the range of 4 µm to 9 µm, or any value or range of values within that range.

A dimension of a sample well corresponding to the depth of the sample well may be defined by the expression $h_M$-$h_W$. Dimension $h_M$-$h_W$ may be in a range of 50 nm to 450 nm, or any value or range of values within that range. In some embodiments, dimension $h_M$-$h_W$ is between 95 nm and 150 nm. In some embodiments, $h_M$-$h_W$ may be approximately 100 nm. In some embodiments, dimension $h_M$-$h_W$ is between 250 nm and 350 nm. In some embodiments, $h_M$-$h_W$ may be approximately 300 nm. The dimension $h_M$-$h_W$ may also impact the directionality of emission energy in a pixel. A value of dimension $h_M$-$h_W$ may allow a sensor of the integrated device to detect a desired level of power of emission energy. The distance between the bottom of the sample wells and the sensors in substrate 4-105 may be configured so as to control the amount of energy detected by one of the sensors and/or the crosstalk between adjacent pixels. The sensors may occupy a plane in substrate 4-105, and in some embodiments, the distance between the bottom of the sample wells and the plane of the sensors may be in the range of 4 µm to 9 µm, or any value or range of values within that range.

Integrated device 4-100 may include metal layer 4-122 over top cladding 4-118. Metal layer may act as a reflector for emission energy emitted by a sample in a sample well and may improve detection of emission energy by reflecting emission energy towards a sensor of the integrated device. Metal layer 4-122 may act to reduce the background signal due to photons that do not originate within the sample well. Metal layer may comprise one or more sub-layers. Examples of suitable materials to be used as a metal layer include aluminum, titanium and titanium nitride. Metal layer 4-122 may have one or more discontinuities corresponding to the etched portions of top cladding 4-118 to form sample wells $4\text{-}108_1$, $4\text{-}108_2$, $4\text{-}108_3$, $4\text{-}108_4$, $4\text{-}108_5$, and $4\text{-}108_6$. Metal layer 4-122 may have a discontinuity corresponding to excitation energy coupling region 4-115.

In some embodiments, a plurality of trenches of the type described herein may be formed to reduce optical loss due to the interaction of the optical mode traveling down waveguide 4-116 and metal layer 4-122. Some embodiments relate to an integrated device that has a trench region in the top cladding that overlaps with a waveguide and a row of sample wells proximate to the waveguide. In some embodiments, an integrated device may include a trench region for a single sample well. The integrated device may have multiple trench regions in the top cladding where each trench region corresponds to one sample well.

Some embodiments of the present application relate to an integrated device having a trench region for each sample well. FIG. 4-1B is a schematic of upper stack 4-161 having multiple trench regions 4-130 positioned proximate to waveguide 4-136. Such a configuration may improve the relative length of waveguide 4-136 along the x-direction where the thickness of top cladding 4-138 has a dimension $h_c$ than if one trench region was formed to include all of the sample wells 4-128, such as the exemplary integrated device shown in FIG. 4-1A. By having multiple trench regions 4-130, top cladding 4-138 may reduce the amount of length along waveguide 4-136 where top cladding has dimension $h_M$ from surface 4-154. Such a configuration for upper stack 4-161 may reduce overall optical loss in comparison to upper stack 4-151 because of the regions between adjacent sample wells have a top cladding thickness to reduce absorption losses of the excitation energy with metal layer 4-152. Trench region 4-130 may have a dimension along the x-direction of $W_t$. Dimension $W_t$ may be in the range of 300 nm to 2000 nm, or any value or range of values within that range. In some embodiments, dimension $W_t$ is between 500 nm and 1000 nm. In some embodiments, dimension $W_t$ is approximately 900 nm. In some embodiments, $W_t$ may be configured so as to provide resonance of the excitation energy and/or the emission energy.

Figures 1A, 5:
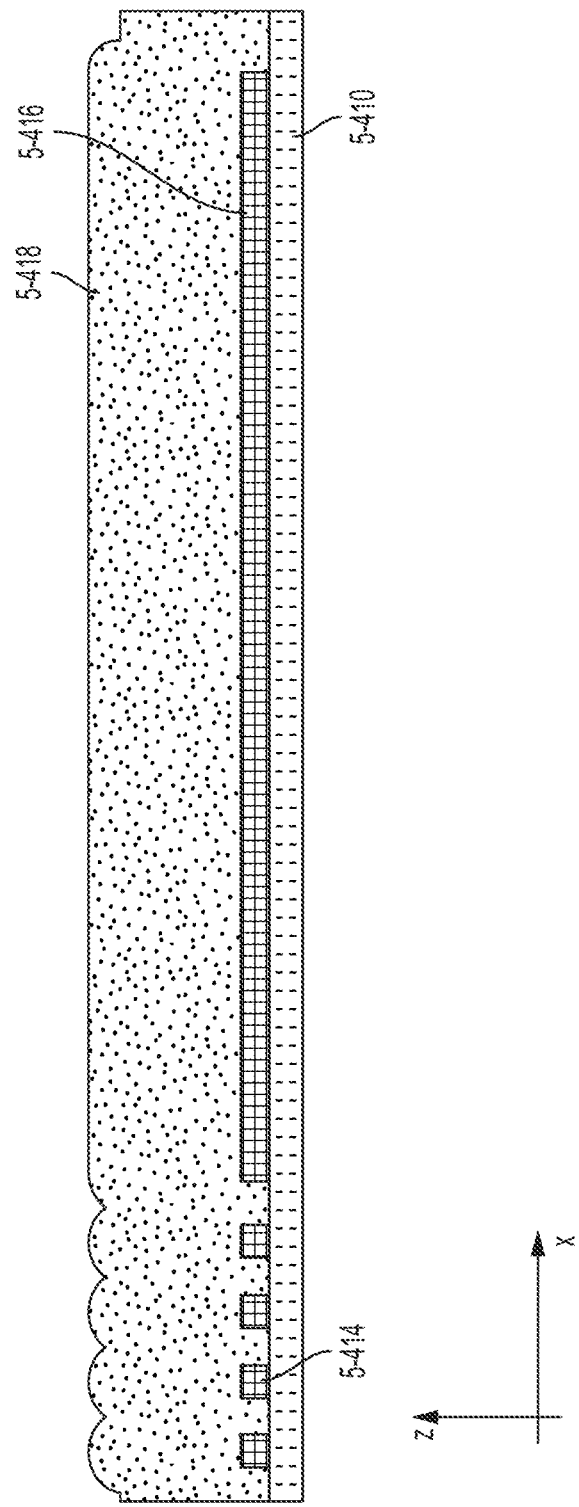
Figures 1B, 5:
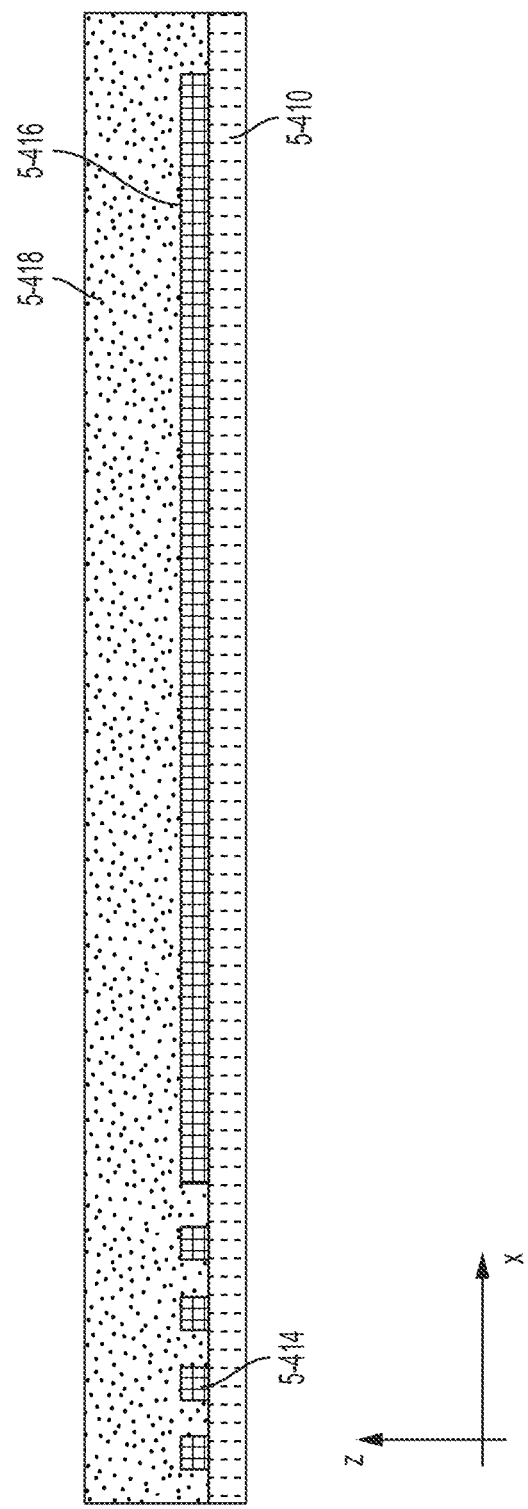
Figures 1C, 5:
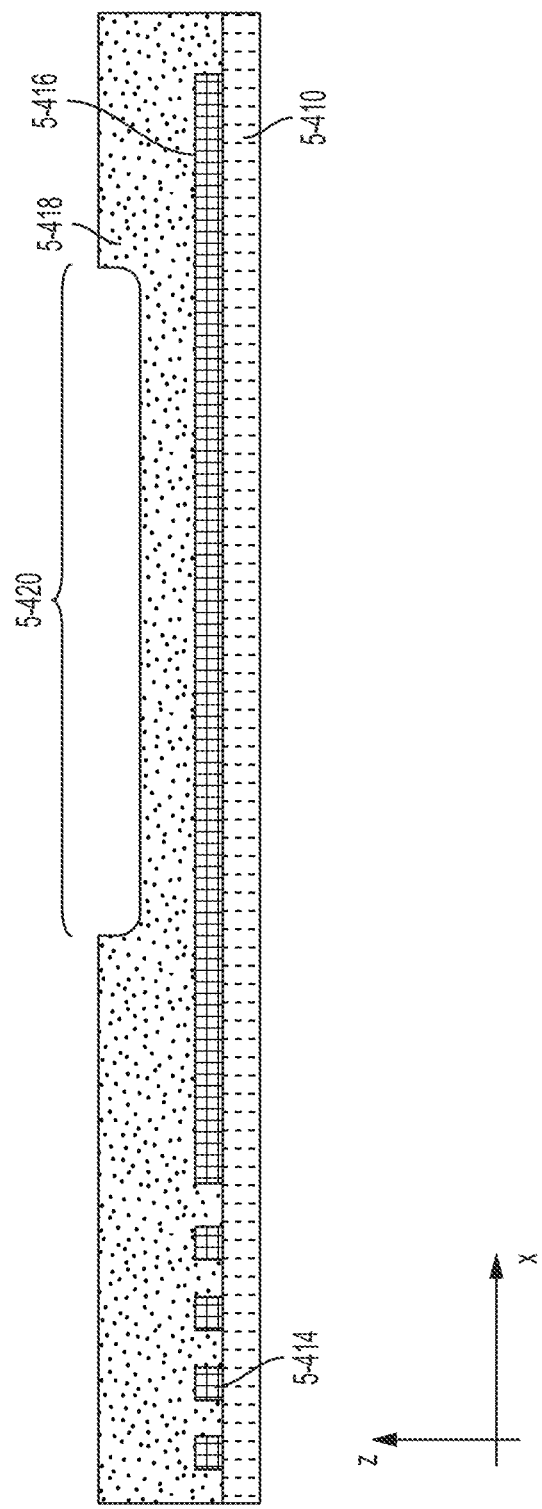
Figures 2A, 5:
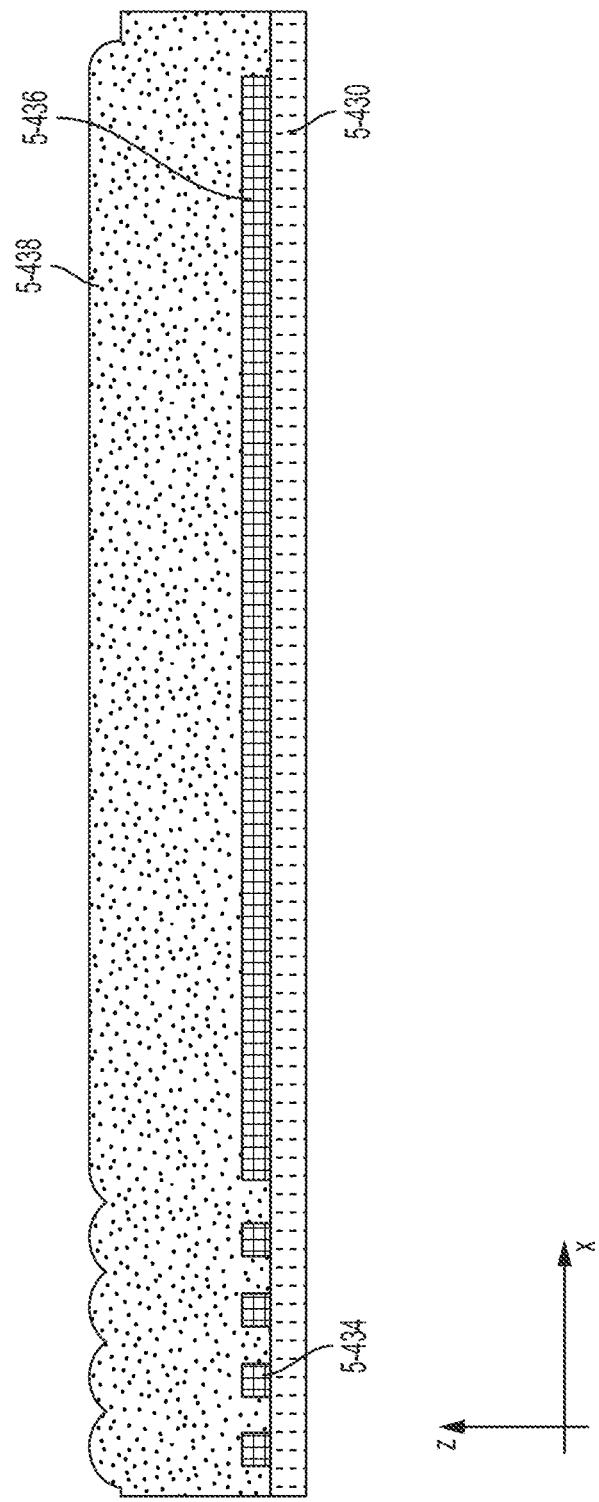
Figures 2B, 5:
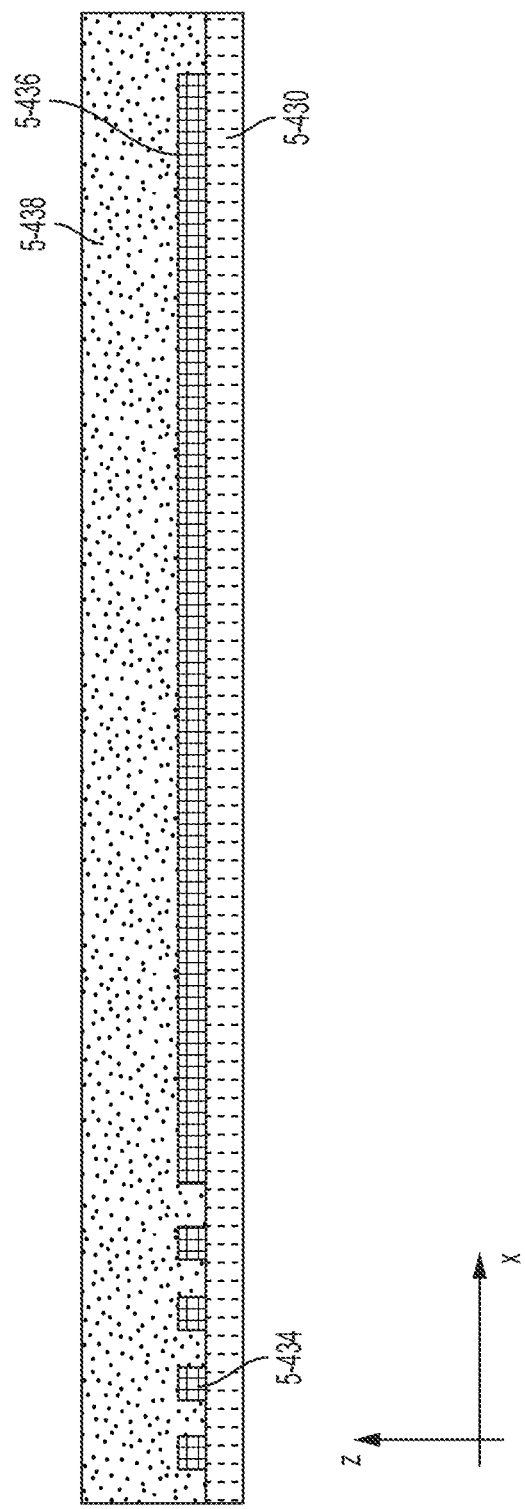
Figures 2C, 5:
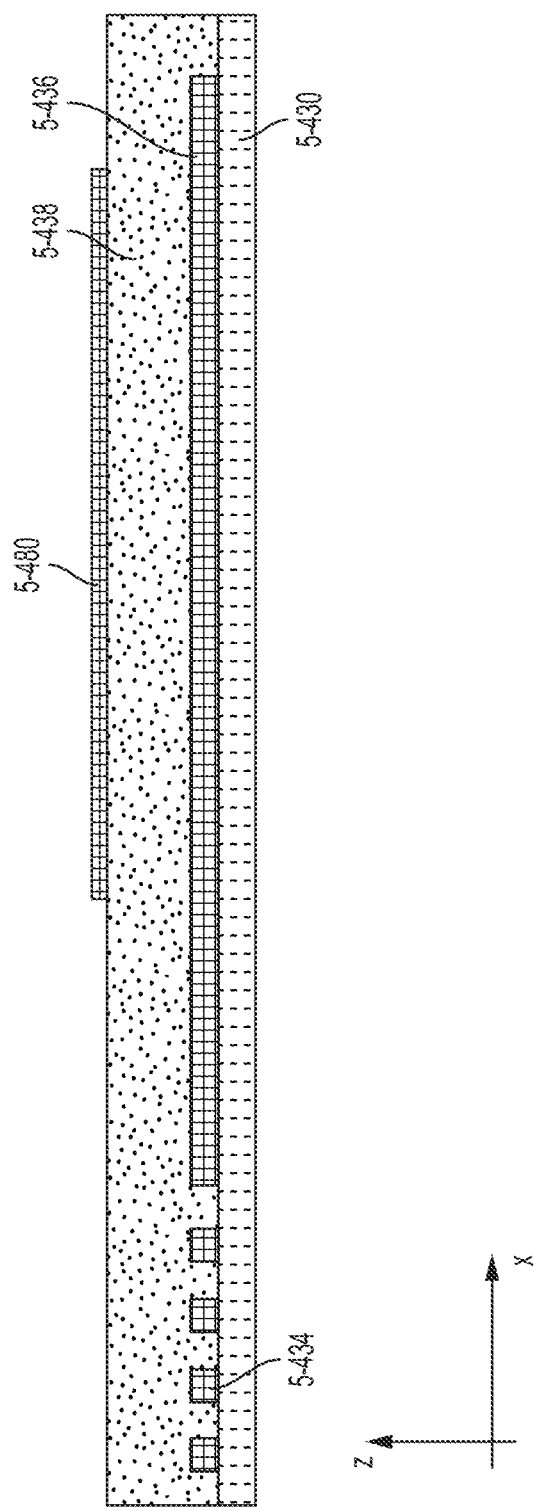
Figures 2D, 5:
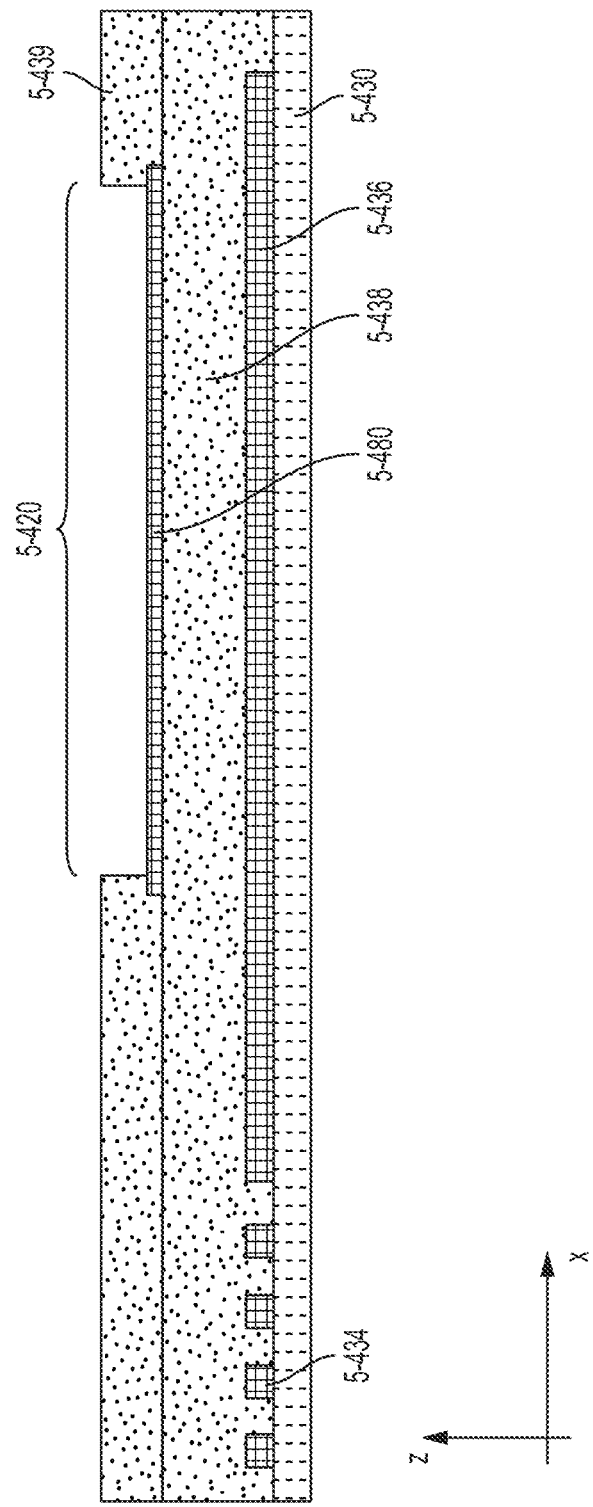
Figures 1A, 6:
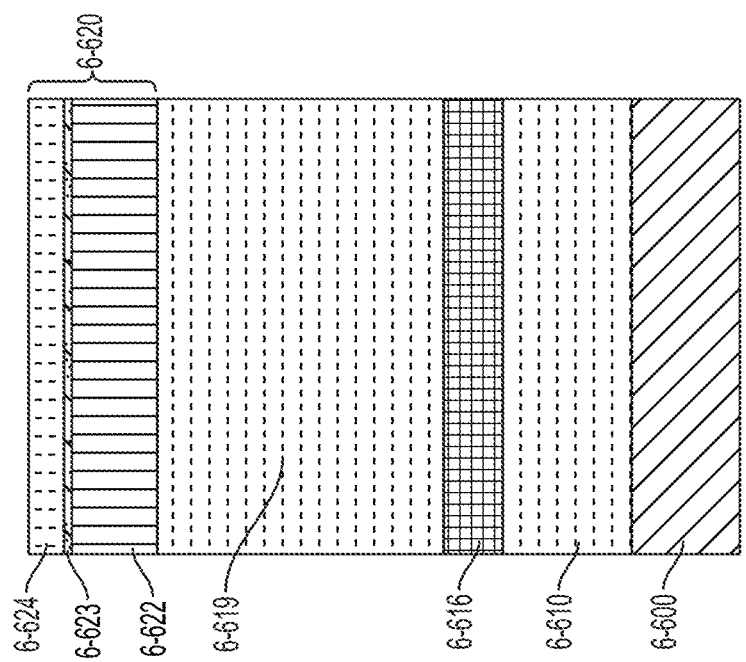
Figures 1B, 6:
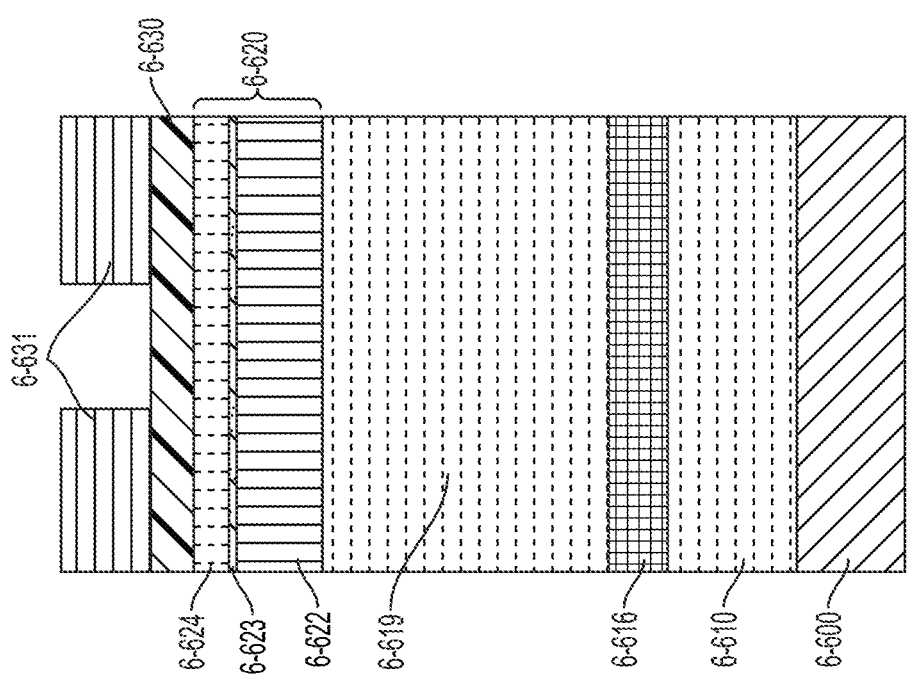
Figures 1C, 6:
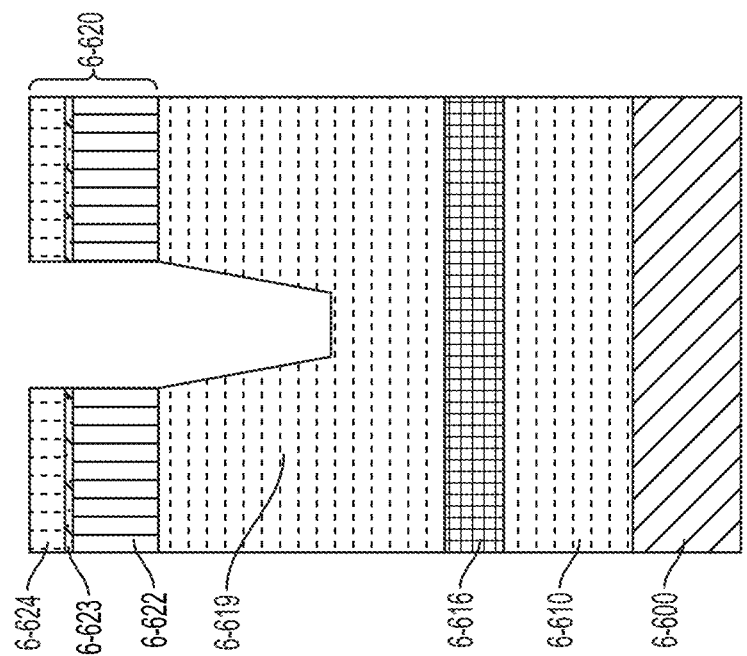
Figures 1D, 6:
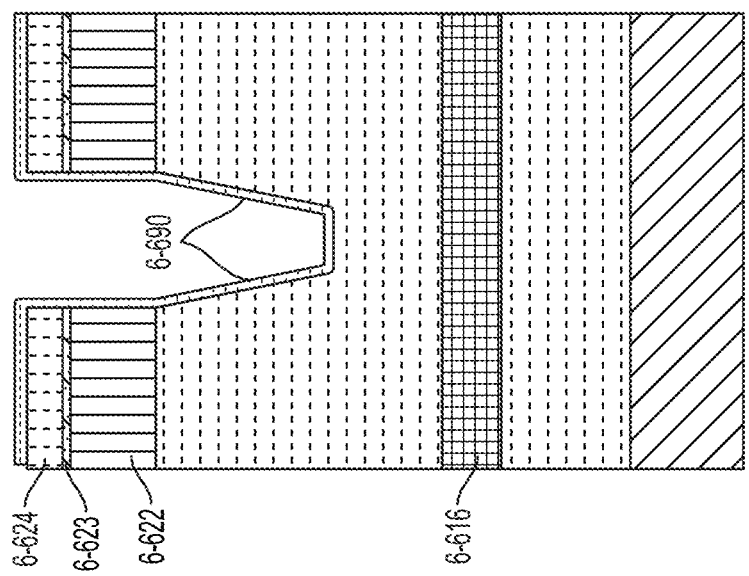

Trench regions may have any suitable size and shape (e.g., circular, rectangular) and be arranged in any suitable manner relative to sample wells and/or waveguides of the integrated device. A trench region may include any suitable number of sample wells and overlap with one or more waveguides of the integrated device. In some embodiments, there is a one-to-one correspondence between a trench region and a sample well such that only one sample well is disposed within a trench region. FIG. 4-1C is an exemplary planar view along a xy plane intersecting waveguide 4-136 shown in FIG. 4-1B. The relative positions of trench regions 4-130 and sample wells 4-128 disposed within individual trench regions are shown by dashed lines. In this exemplary configuration, trench regions 4-130 have a circular shape, although a trench region may have other suitable shapes (e.g., square, triangular) that may reduce optical loss. In some embodiments, multiple sample wells may be disposed within a single trench region. The trench region may overlap with multiple waveguides. FIG. 4-1D is another exemplary planar view along a xy-plane intersecting waveguide 4-136 shown in FIG. 4-1B. Trench regions 4-130 extend approximately perpendicular to the direction of light along waveguides 4-136 and include sample wells 4-128 positioned to couple excitation energy from different waveguides 4-136. As shown in FIG. 4-1D, sample wells 4-128a, 4-128b, and 4-128c are disposed within trench region 4-130b where sample wells 4-128a, 4-128b, and 4-128c are positioned to receive excitation energy from waveguides 4-136a, 4-136b, and 4-136c, respectively. Although only three waveguides are shown in FIGS. 4-1C and 4-1D, it should be appreciated that an integrated device may have any suitable number of waveguides and trench regions positioned to overlap with one or more waveguides.

The size and shape of a trench region may provide one or more benefits related to functionalization and/or modification of one or more surfaces of a sample well. As described herein, a surface of a sample well may be modified and/or functionalized to provide a certain type and/or level of interaction with another type of molecule (e.g., an interaction that improves the association of a polymerase to a surface). One type of technique for functionalizing a surface of a sample well may include using particles that have a dimension that allows the particles to reside within a trench region of the integrated device. The particles may carry one or more chemical species configured to functionalize and/or modify a surface of the sample well. The surface topography of the trench regions may act to retain the particles in proximity to surfaces of the integrated device where chemical functionalization and modification is desired. The particles may have a dimension that provides a favorable surface interaction with a surface of trench region. In some embodiments, the curvature of the particles may improve an amount of surface interaction between the particle and a surface of the trench region. In some embodiments, the particles may a have a diameter larger than a dimension of a trench region such that the portion of a particle may enter the trench region. In some embodiments, the particles may have a diameter in the range of 1 micron to 5 microns, or any value or range of values within that range. Examples of suitable materials for the particles include polystyrene and latex. In some embodiments, the particles are magnetic particles.

In some embodiments, template DNA strands are coupled to the particles and the interaction between the particles and the surface topography of the trench regions may improve the localization of the template DNA strands in proximity to the sample wells of the integrated device. A particle may be bound to multiple copies of a template DNA strand such that positioning of the particle relative to a sample well increases the local concentration of the template DNA strand, which may improve loading and retention of the template DNA strand in the sample well. In some embodiments, the template DNA strand is approximately 10 kb long.

Some embodiments of the present application relate to techniques for reducing the distance between a sample well and one or more sensors within a pixel of an integrated device. The closer the sample well is positioned relative to a sensor, the wider the solid angle from which radiation can be detected by the sensor. The wider collection angle may improve collection efficiency for emission energy emitted from a sample well positioned in the sample well. Such techniques for positioning sample wells at a closer distance to one or more sensors may reduce signal crosstalk between different pixels, such as a sensor detecting emission energy from a sample well in an adjacent pixel, for example.

One type of technique for reducing the distance between a sample well and a sensor may include forming one or more sample well layers within and/or below a plane of the integrated device that includes a metal layer configured to route electrical signals within the integrated device. Such a configuration may provide a distance between a surface of the sample well and the sensor to be in the range of 1 μm to 5 μm, or any value or range of values within that range. In some embodiments, a distance between a surface of a sample well and a sensor in a pixel of the integrated device may be in the range of 2 μm and 3 μm, or any value or range of values within that range. A waveguide configured to deliver excitation energy to the sample well may be positioned between the sample well and sensor. The waveguide may overlap or be positioned below a plane that includes a metal layer that may act as an electrical route for the integrated device. In this manner, waveguide may be considered to be embedded within the back-end-of-line (BEOL) wiring of the integrated device.

Some embodiments of the present application relate to an integrated device that includes a sample well positioned in a plane that overlaps with a metal layer and/or is positioned between a metal layer and a sensor of the integrated device. FIG. 4-2 is a cross-sectional view perpendicular to the propagation axis of excitation energy of an integrated device that includes sample well 4-208 positioned in a plane along the z-direction that overlaps with a region along the z-direction includes metal layers $4\text{-}203_A$, $4\text{-}203_B$, $4\text{-}203_C$, $4\text{-}203_D$. As shown in FIG. 4-2, sample well 4-208 is positioned in a xy plane between at least one metal layer 4-203 and a sensor located in substrate 4-200.

Integrated device 4-260 shown in FIG. 4-2 may include a substrate 4-200 (e.g., a silicon substrate), which may include one or more sensors configured to detect emission energy. Signals provided by a sensor may provide an indication of the lifetime, intensity, and/or spectra of the emission energy. Integrated device 4-260 may comprise dielectric layer 4-202 formed of any suitable dielectric material (e.g., doped silicon oxide, undoped silicon oxide). Integrated device 4-260 may include cladding 4-210 formed of any suitable material (e.g., silicon oxide). In some embodiments, cladding 4-210 may include undoped silicon oxide, which may reduce the amount of optical loss for excitation energy propagating along waveguide 4-216.

Integrated device 4-260 may comprise one or more metal layers $4\text{-}203_A$, $4\text{-}203_B$, $4\text{-}203_C$ and $4\text{-}203_D$ of integrated device 4-260 configured to route electrical signals within integrated device 4-260, transmit electrical signals to an external device (e.g., an instrument configured to interface with integrated device 4-260), and/or receive electrical signals from an external device (e.g., an instrument). In some embodiments, one or more metal layers of integrated device 4-260 may act to reduce the amount of light arriving from outside the pixel that includes sample well 4-208 from being detected by a sensor in the pixel. In this manner, a metal layer may reduce noise artifacts arising from background signal from light off of the integrated device and/or reduce crosstalk signal that may arise from light from other pixels being detected by the sensor. While FIG. 4-2 illustrates an integrated device with four metal wiring layers, the techniques of the present application are not limited in this respect and any other suitable number of metal wiring layers may be used. Metal wiring layers may be electrically connected through one or more vias (e.g., tungsten vias). For example, via $4\text{-}204_A$ may connect metal layer $4\text{-}203_A$ to substrate 4-200. Via $4\text{-}204_B$ may connect metal layer $4\text{-}203_A$ to metal layer $4\text{-}203_B$. Via $4\text{-}204_C$ may connect metal layer $4\text{-}203_B$ to metal layer $4\text{-}203_C$. Via $4\text{-}204_D$ may connect metal layer $4\text{-}203_C$ to metal layer $4\text{-}203_D$.

Waveguide 4-216 of integrated device 4-260 may have a configuration that allows light to propagate in a direction perpendicular to the plane of FIG. 4-2. In some embodiments, at least one metal layer is disposed at a distance from substrate 4-200 along the z-axis that is less than the distance along the z-axis between a surface of waveguide 4-216 and substrate 4-200. Metal layer $4\text{-}203_A$, as shown in FIG. 4-2, is positioned at be a distance from substrate 4-200 along the z-axis that is less than the distance along the z-axis between a surface of waveguide 4-216 and substrate 4-200. In some embodiments, at least one metal layer is disposed at a distance from substrate 4-200 along the z-axis that is greater than the distance along the z-axis between a surface of waveguide 4-216 and substrate 4-200. Metal layers $4\text{-}203_C$ and $4\text{-}203_D$ may be disposed at a distance from substrate 4-200 along the z-axis that is greater than the distance along the z-axis between a surface of waveguide 4-216 and substrate 4-200.

Integrated device 4-260 may include trench region 4-220. Trench region 4-220 may have a dimension along the z-direction such that trench region 4-220 overlaps in a xy plane with one or more metal layers 4-203. In some embodiments, trench region 4-220 may have a rectangular shape (e.g., square). A surface of trench region 4-220 may include at least one sample well, including sample well 4-208. In some embodiments, trench region 4-220 may comprise a plurality of sample wells 4-208 disposed in a row along the x-axis. In other embodiments, trench 4-220 may comprise a single sample well.

Integrated device 4-260 may include metal layer 4-222 disposed on top of cladding 4-210. Metal layer 4-222 may have one or more discontinuities corresponding to the etched portions of cladding 4-210 that form sample well 4-208. Metal layer 4-222 may comprise one or more sub-layers of one or more suitable materials. Examples of suitable materials that may be used to form metal layer 4-222 may include aluminum, titanium, and titanium nitride.

A sample well of an integrated device may have a configuration of a cavity in one or more layers of the integrated device. The sample well may extend through a metal layer disposed on a surface of the integrated device. The sample well may be formed through a portion of a dielectric material, which may be formed between the metal layer and a waveguide. The metal layer may act as a reflector for emission energy and may improve collection of photons of emission energy by a sensor of the pixel that includes the sample well.

The sample well may be suitably sized and shaped to receive a sample and contain the sample for a duration of time to allow for analysis of the sample. One or more surfaces of a sample well may be configured to preferentially retain the sample at a distance from a waveguide of the integrated device. In some embodiments, the sample may adhere to a surface of the sample well approximately parallel to the direction of light propagation along a waveguide. A sample well may have an aperture with a cross-sectional dimension that reduces the impact of light from off the integrated device from reaching a sample and/or a sensor of the integrated device. The sample well may form an opening at a surface of the integrated device where the area of the opening at the surface forms the aperture of the sample well. A dimension of the aperture may act to provide a suitable number and/or concentration of luminescent labels present in the sample well. The opening of the sample well may be formed in one or more metal layers of the surface of the integrated device. The one or more metal layers may act to reduce the amount of excitation energy that reaches a bulk solution deposited on the integrated device and illuminates the bulk solution, which may reduce the amount of light emitted from luminescent markers present in the bulk solution contributing to a background signal.

Aspects of the present application relate to techniques for positioning a sample within a sample well of an integrated device at a suitable distance from a metal layer disposed on a surface of the integrated device. The metal layer may impact the detected lifetime of a marker (e.g., fluorophore) because the conditions surrounding the marker can impact the photon emission events of the marker. For example, a lifetime detected for a marker closer to a metal layer may be smaller than a lifetime detected for the same marker located further away. As the lifetime values for different markers become smaller due to the presence of the metal layer, it can be challenging to distinguish among the different markers based on an indication of lifetime because the lifetime values are compressed into a narrower range. Distinguishing among different markers based on an indication of a lifetime may be improved by an integrated device that broadens variation of the individual lifetimes for the different markers. Some embodiments of the present application relate to an integrated device configured to reduce lifetime compression for markers used to detect a sample by positioning the sample at a suitable distance from a metal layer of the integrated device. In some embodiments, a first surface of a sample well distal to a metal layer may have different surface chemistry than a second surface of the sample well such that a sample preferentially is associated with the first surface over the second surface.

FIG. 4-3 is a cross-sectional view of integrated device that includes sample well 4-308, according to some embodiments. Sample well 4-308 may be configured to receive sample 4-391, which may be retained at a surface of sample well 4-308. A surface of sample well 4-308 proximate to waveguide 4-316 may have a composition that adheres to the sample, at least temporarily for a duration of time. A surface of sample well 4-308 proximate to waveguide 4-316 may have one or more materials that provide selectivity for sample 4-391 to adhere to the surface rather than a side wall of sample well 4-308, as shown in FIG. 4-3. Such a configuration may maintain sample 4-391 proximate to waveguide 4-316. In some embodiments, a surface of sample well 4-308 proximate to waveguide 4-316 may allow for photoactivated binding of sample 4-391 to sample well 4-308. In some embodiments, a surface of sample well 4-308 proximate to waveguide 4-316 may be formed of silicon oxide, which may be terminated with one or more silanol groups (Si—OH). A silanol group may interact with another material (e.g., a chemical having a structure with one or more silane groups) to create a certain type of surface chemistry for the surface. Sample 4-391 may be disposed within sample well through a top aperture of sample well 4-308. The top aperture may be configured to reduce ambient light or stray light from illuminating sample 4-391 and/or sensor 4-300. In some embodiments, sample well 4-308 may have a sub-wavelength cross-sectional dimension, which may inhibit or reduce light incident on the integrated device. The top aperture of sample well 4-308 may have a width $w_A$ that is in the range of 50 nm and 300 nm, or any value or range of values within that range.

Sample well 4-308 may have dimension $d_W$ between a surface of sample well 4-308 parallel or approximately parallel to the direction of light propagation along waveguide 4-316 and interface 4-327 between cladding 4-318 and metal layer 4-322. Dimension $d_W$ may provide a suitable distance between a sample positioned at the surface from metal layer 4-322. Dimension $d_W$ may impact the timing of photon emission events of a marker (e.g., lifetime) associated with sample 4-391 due to the confinement of the sample in the sample well. Accordingly, dimension $d_W$ may allow for distinguishing among different markers in sample well 4-308 based on timing characteristics associated with the individual lifetimes of the different markers. In some embodiments, dimension $d_W$ of sample well 4-308 may impact the amount of excitation energy received from waveguide 4-316. Dimension $d_W$ may be in the range of 50 nm to 450 nm, or any value or range of values within that range. In some embodiments, dimension $d_W$ is between 95 nm and 150 nm. In some embodiments, dimension $d_W$ is between 250 nm and 350 nm.

A metal layer of an integrated device may include one or more layers of material. Examples of suitable materials to be used as layers of a metal layer may include aluminum, copper, titanium, and titanium nitride. As shown in FIG. 4-3, metal layer 4-322 includes at least two sub-layers. In some embodiments, a first sub-layer positioned to interface with cladding 4-318 may include aluminum. The aluminum may be alloyed with silicon or copper in some embodiments. By having aluminum in the first sub-layer, optical loss of excitation energy propagating along waveguide 4-176 may be reduced. The thickness of the first sub-layer may be in the range of 30 nm to 165 nm, or any value or range of values within that range.

In some embodiments, metal layer 4-322 may include a second sub-layer disposed over the first sub-layer. In some embodiments, the second sub-layer may include titanium. Titanium may reduce the amount of corrosion that occurs within metal layer 4-322. The thickness of the second sub-layer may be in the range of 5 nm to 100 nm, or any value or range of values within that range. In some embodiments, the thickness of the second sub-layer may be approximately 10 nm.

In some embodiments, metal layer 4-322 may include a third sub-layer disposed over the second sub-layer and/or over the first sub-layer. The third sub-layer may include titanium nitride. The third sub-layer may have a thickness in the range of 5 nm to 100 nm, or any value or range of values within that range. In some embodiments, the third sub-layer may have a thickness of approximately 30 nm.

Sample well 4-308 may have one or more sidewalls covered, at least partially, with a sidewall spacer 4-390. The composition of sidewall spacer 4-390 may be configured to enable a certain type of interaction with sample 4-391. In some embodiments, sidewall spacer 4-390 may have a composition configured to passivate the sidewalls of sample well 4-308 to reduce the amount of sample that adheres to the sidewall of sample well 4-308. By coating only the sidewalls of the sample wall with the spacer, a different type of interaction with sample 4-391 may be provided at a different area of sample well 4-308. In some embodiments, the surface of sample well 4-308 parallel or approximately parallel to the direction of light propagation along waveguide 4-316 may be coated with a silane to improve adherence of sample 4-391 to the surface. By coating the sidewalls with spacer 4-390, one or more surfaces of the sample well 4-308 may be selectively coated with the silane. The composition of sidewall spacer 4-390 may be selected to provide selective coatings of sidewall spacer 4-390 relative to the surface of sample well 4-308 that is parallel or approximately parallel to the waveguide. Sidewall spacer 4-390 may have a thickness in the range of 3 nm to 30 nm, or any value or range of values within that range. In some embodiments, sidewall spacer 4-390 may have a thickness of approximately 10 nm. Examples of suitable materials used to form sidewall spacer 4-390 include $TiO_2$, TiN, TiON, TaN, $Ta_2O_5$, $Zr_2O_5$, and $HfO_2$. In some embodiments, sidewall spacer 4-390 includes TiN, which may provide a desired level of directionality of emission energy towards sensor 4-300 due to the refractive index of TiN. Sidewall spacer 4-390 may be configured to block scattered light, including scattered emission energy from waveguide 4-316, thus reducing the amount of scattered light that may illuminate sample 4-391.

III. Fabrication Techniques

In some embodiments, formation of an integrated device may include forming an upper stack and a lower stack from a single substrate. In some embodiments, an integrated device can be formed by forming an upper stack from a first substrate and a lower stack from a second substrate and bonding the upper stack and the lower stack together. Bonding of the lower stack and the upper stack may occur at any suitable stage of forming the integrated device. In some embodiments, bonding of the lower stack and the upper stack may occur at the wafer-level prior to forming individual integrated circuits. In some embodiments, bonding of the lower stack and the upper stack may occur at the die-level where the upper stack and the lower stack are diced prior to bonding. In some embodiments, bonding of the upper stack and the lower stack may occur through a flip-chip bonding process.

Some embodiments of the present application relate to techniques for forming a trench region by forming a layer of material that results in a cladding layer of the integrated device and selectively removing a portion of the layer to form the trench region. FIG. 5-1A, FIG. 5-1B, and FIG. 5-1C illustrate steps of a method for forming a trench region of an upper stack of an integrated device, such as integrated device 4-100, according to some embodiments. Bottom cladding 5-410 may be formed using any suitable technique. In some embodiments, bottom cladding 5-410 may be formed on a substrate (e.g., silicon substrate). In some embodiments, bottom cladding 5-410 may be formed on a lower stack of an integrated device, such as lower stack 4-150 of integrated device 4-100.

Waveguide 5-416 and grating coupler 5-414 may be formed over bottom cladding 5-410 by forming a layer of one or more materials (e.g., silicon nitride). Layer may have a suitable refractive index to provide desired optical properties for propagating excitation energy by the waveguide. Any suitable fabrication techniques may be used to pattern waveguide 5-416 and/or grating coupler 5-414. In some embodiments, a layer of material may be formed over bottom cladding 5-410 and a mask may be patterned over the layer such that the exposed regions of the layer may be selectively etched to form the desired pattern for waveguide 5-416 and grating coupler 5-414.

Layer of material 5-418 may be formed over waveguide 5-416, as shown in FIG. 5-1A, as a top cladding layer of the integrated device. Layer 5-418 may be formed by growing a material and/or depositing the material to a desired thickness. Layer 5-418 may include any suitable dielectric material having a desired level of transparency to excitation energy and emission energy. Examples of suitable materials used to form layer 5-418 include silicon oxide, aluminum oxide, and titanium oxide. In some embodiments, the thickness, along the z-axis, of the layer formed over waveguide 5-416 shown in FIG. 5-1A may be in the range of 500 nm to 1200 nm, or any value or range of values within that range. In some embodiments, the thickness of layer 5-418 may be approximately 850 nm. Layer 5-418 may have variation in thickness by being formed over a patterned layer (e.g., grating coupler 5-414).

Layer 5-418 may be planarized to form a surface of a top cladding of an integrated device, as is shown in FIG. 5-1B. In some embodiments, the cladding may be planarized through a chemical mechanical planarization (CMP) process. The CMP process may reduce the surface roughness of the surface of the top cladding, which may reduce optical loss of excitation energy as it propagates along a waveguide proximate to the surface, such as waveguide 5-416. The thickness of layer 5-418 along the z-direction may be reduced as a result of the planarization process. In some embodiments, the thickness of the top cladding may be decreased by 250 nm. A thickness of the resulting top cladding may have a dimension along the z-direction in the range of 100 nm to 500 nm, or any value or range of values within that range.

A trench region 5-420 may be formed in layer 5-418, as shown in FIG. 5-1C, trench 5-420. Trench region 5-420 may be formed by exposing the top surface of layer 5-418 through a photo-mask and by selectively etching a region of the layer. In some embodiments, the etching processed may be timed so as to etch the layer by a desired amount to achieve a resulting dimension along the z-direction of the resulting trench region. In some embodiments, layer 5-418 may be time etched by a duration of time used to achieve a dimension along the z-direction corresponding to a value in the range of 100 nm to 500 nm, or any value or range of values within that range. The resulting distance between a surface of trench region 5-420 parallel or approximately parallel to the direction of light propagation along waveguide 5-416 and waveguide 5-416 may be in the range of 200 nm to 800 nm, or any value or range of values within that range. In some embodiments, a distance between the surface of trench region 5-420 and waveguide 5-416 may be approximately 400 nm.

In some embodiments, formation of trench region 5-420 may include multiple etching processes. A first time etch process used to form trench region 5-420 may be a dry etch or any suitable anisotropic etch. The first etch process may be used to define an area of trench region 5-420. The first etch process may remove a thickness from a portion of layer 5-418 corresponding to trench region 5-420 in the range of 100 nm to 400 nm, or any value or range of values within that range. In some embodiments, the first etch process may remove approximately 190 nm. A second etch process used to form trench region 5-420 may be a wet etch or any suitable isotropic etch. The second etch process may be used to refine one or more features of trench region 5-420 after the first etch process. In some embodiments, the second etch process may round the corners of trench region 5-420. The second etch process may remove a thickness from a portion of layer 5-418 corresponding to trench region 5-420 in the range of 5 nm to 100 nm, or any value or range of values within that range. In some embodiments, the second etch process may remove approximately 10 nm.

Some embodiments of the present application relate to techniques for forming a trench region by forming a layer of material that results in a cladding layer of the integrated device having a desired thickness. A method for forming the trench region may include forming one or more etch stop layers to improve the accuracy of the thickness of the cladding layer. FIG. 5-2A, FIG. 5-2B, FIG. 5-2C, FIG. 5-2D, FIG. 5-2E and FIG. 5-2F illustrate steps of a method for forming a trench region in an upper stack of an integrated device, such as integrated device 5-102. Bottom cladding 5-430 may be formed using any suitable technique. In some embodiments, bottom cladding 5-430 may be formed on a substrate (e.g., silicon substrate). In some embodiments, bottom cladding 5-430 may be formed on a lower stack of an integrated device, such as lower stack 4-150 of integrated device 4-100.

Waveguide 5-436 and grating coupler 5-434 may be formed over bottom cladding 5-430 by forming a layer of one or more materials (e.g., silicon nitride). Layer may have a suitable refractive index to provide desired optical properties for propagating excitation energy by the waveguide. Any suitable fabrication techniques may be used to pattern waveguide 5-436 and/or grating coupler 5-434. In some embodiments, a layer of material may be formed over bottom cladding 5-430 and a mask may be patterned over the layer such that the exposed regions of the layer may be selectively etched to form the desired pattern for waveguide 5-436 and grating coupler 5-434.

Layer of material 5-438 may be formed over waveguide 5-436, as shown in FIG. 5-2A, which may result in a top cladding layer of an integrated device. Layer 5-438 may be formed by growing a material and/or depositing the material to a desired thickness. Layer 5-438 may include any suitable dielectric material having a desired level of transparency to excitation energy and emission energy. Examples of suitable materials used to form layer 5-438 include silicon oxide, aluminum oxide, and titanium oxide. In some embodiments, the thickness, along the z-axis, of the layer formed over waveguide 5-436 shown in FIG. 5-2A may be in the range of 500 nm to 1200 nm, or any value or range of values within that range. In some embodiments, the thickness of layer 5-438 may be approximately 750 nm. Layer 5-438 may have variation in thickness by being formed over a patterned layer (e.g., grating coupler 5-434).

Layer 5-438 may be planarized to form a surface of a top cladding of an integrated device, as is shown in FIG. 5-2B. In some embodiments, the cladding may be planarized through a chemical mechanical planarization (CMP) process. The CMP process may reduce the surface roughness of the surface of the top cladding, which may reduce optical loss of excitation energy as it propagates along a waveguide proximate to the surface, such as waveguide 5-436. The thickness of layer 5-438 along the z-direction may be reduced as a result of the planarization process. In some embodiments, the thickness of the top cladding may be decreased by 350 nm. A thickness of the resulting top cladding may have a dimension along the z-direction in the range of 100 nm to 500 nm, or any value or range of values within that range.

An etch stop layer 5-480 may be deposited on a surface of layer 5-438, as shown in FIG. 5-2C. The etch stop layer may be patterned to define regions corresponding to a trench region of the integrated device. The etch stop layer may be selectively removed through a lithographic process in some regions while it may be maintained in the region where a trench region is to be formed. Examples of suitable materials used to form etch stop layer 5-480 include SiN, SiON, $SiO_xN_y$, Al, Ti, and TiN. In some embodiments, etch stop layer 5-480 may include layered combinations of multiple materials.

Figures 2E, 5:
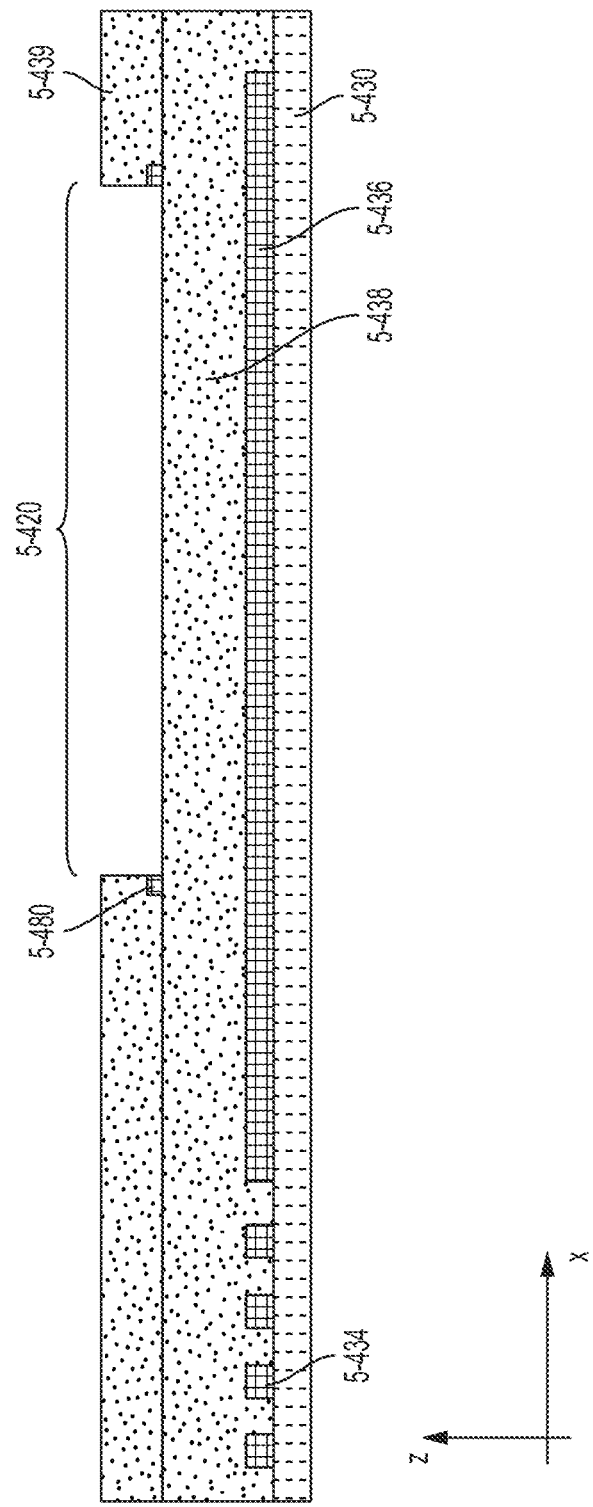

A dielectric layer 5-439 may be formed on a surface of layer 5-438, as shown in FIG. 5-2D. Dielectric layer 5-439 may be grown and/or deposited on the surface of layer 5-438. Examples of suitable materials used to form dielectric layer 5-439 include silicon oxide, aluminum oxide, and titanium oxide. In some embodiments, dielectric layer 5-439 may be deposited through a chemical vapor deposition (CVD) process. In some embodiments, dielectric layer 5-439 may be deposited through a high-density plasma chemical vapor deposition (HDPCVD) process. Dielectric layer 5-439 may be selectively etched in a region that at least partially overlaps with etch stop layer 5-480. During etching, the presence of etch stop layer 5-480 may reduce etching beyond etch stop layer 5-480 and/or into layer 5-438. The etch process using etch stop layer 5-480 may provide formation of dielectric layer 5-439 of a desired dimension along the z-axis. Such a technique may improve the accuracy of the dimensions of layers within the integrated device without using of a time etching process as part of the fabrication process. The etch stop layer may be at least partially removed using any suitable lithography techniques, as shown in FIG. 5-2E. Removal of some or all of the etch stop layer may occur through a strip process configured to reduce the formation of undercut regions at the edge of the trench region and/or oxidation of the surface of layer 5-438. The remaining portion of dielectric layer 5-439 and layer 5-348 may act as a top cladding layer of an integrated device.

Figures 2F, 5:
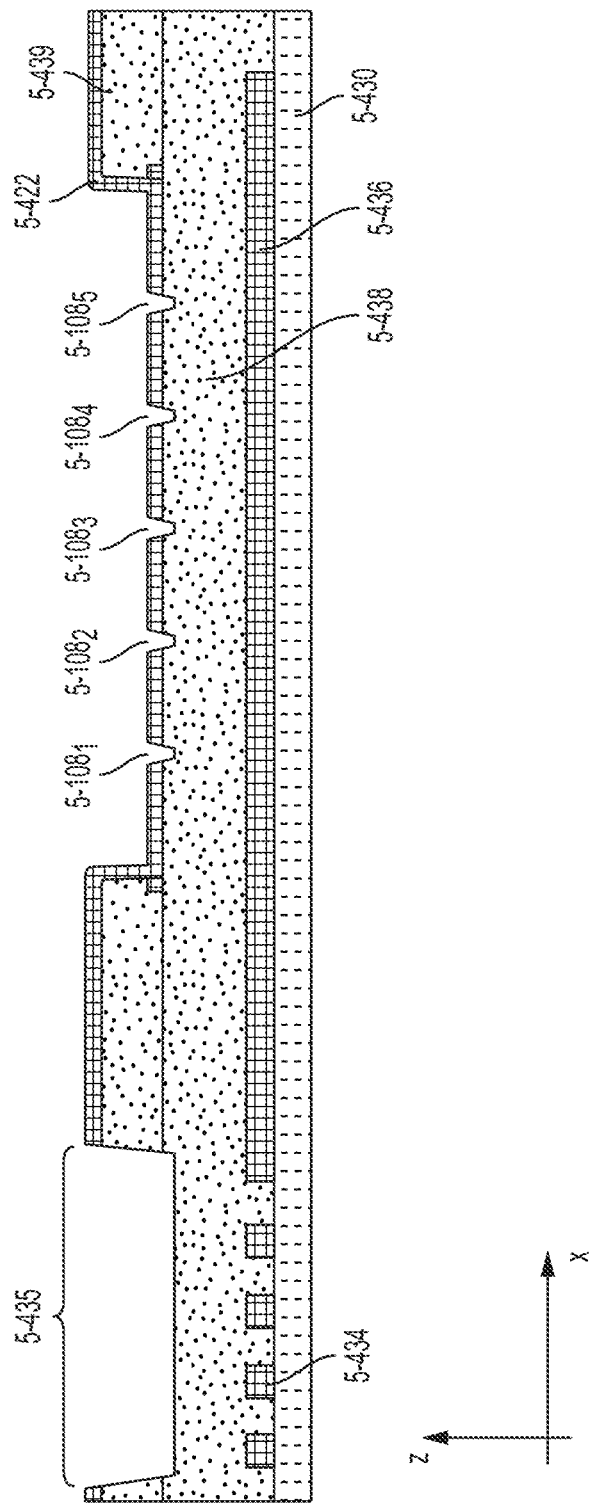
Figures 3A, 5:
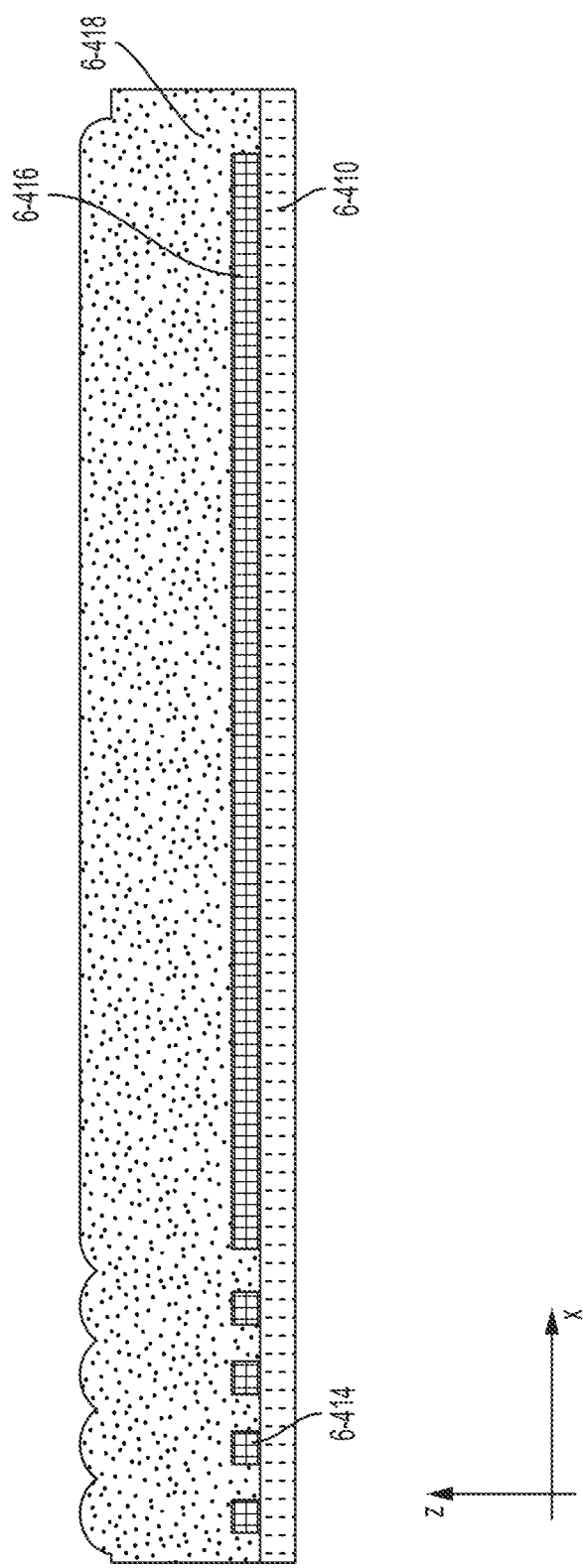
Figures 3B, 5:
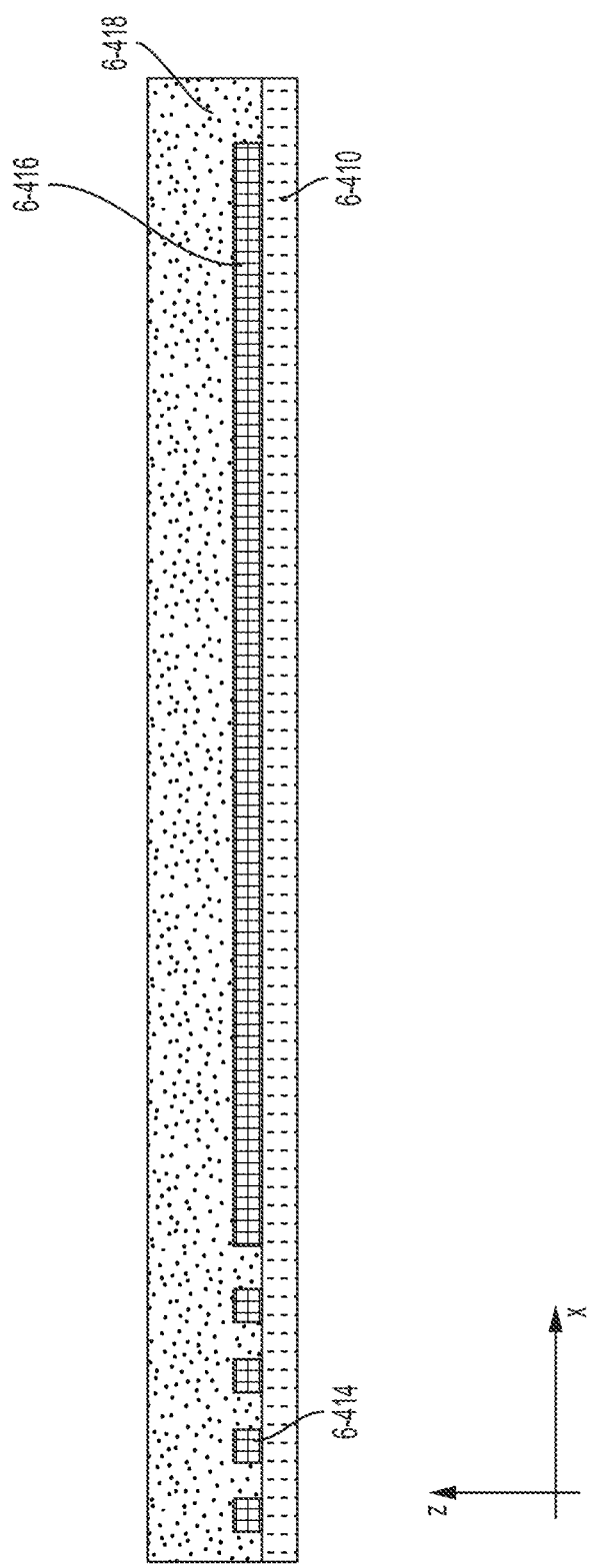

Metal layer 5-422 may be formed over dielectric layer 5-439 and/or on a surface of layer 5-438. As shown in FIG. 5-2F, metal layer 5-422 may be deposited on a surface of dielectric layer 5-439 and on the exposed surface of layer 5-438. Metal layer 5-422 may include aluminum, titanium, titanium nitride, or any suitable combination thereof. Sample wells $5-108_1$, $5-108_2$, $5-108_3$, $5-108_4$, and $5-108_5$ may be formed by selectively removing regions of metal layer 5-422 and layer 5-438. Sample wells $5-108_1$, $5-108_2$, $5-108_3$, $5-108_4$, and $5-108_5$ may be formed using a photo-lithographic process step by applying a photo-mask exposing the desired regions for formation of the sample wells and exposing the surface to selectively etch those regions. While FIG. 5-2F illustrates five sample wells, the techniques of the present application are not limited in this respect and any suitable number of sample wells may be formed. The etching process may comprise a first etch through metal layer 5-422 and a second etch in layer 5-438. Excitation energy coupling region 5-435 may be formed by removing a portion of metal layer 5-435, dielectric layer 5-439, and/or layer 5-438 that overlaps at least partially with grating coupler 4-114 along the z-axis.

Some embodiments of the present application relate to forming an integrated device by using an etch stop process as part of forming one or more sample wells of the integrated device. FIG. 5-3A, FIG. 5-3B, FIG. 5-3C, FIG. 5-3D, FIG. 5-3E, FIG. 5-3F and FIG. 5-3G illustrate steps of a method for forming a trench region in an upper stack of an integrated device, such as integrated device 5-102. Bottom cladding 6-410 may be formed using any suitable technique. In some embodiments, bottom cladding 6-410 may be formed on a substrate (e.g., silicon substrate). In some embodiments, bottom cladding 6-410 may be formed on a lower stack of an integrated device, such as lower stack 4-150 of integrated device 4-100.

Waveguide 6-416 and grating coupler 6-414 may be formed over bottom cladding 6-410 by forming a layer of one or more materials (e.g., silicon nitride). Layer may have a suitable refractive index to provide desired optical properties for propagating excitation energy by the waveguide. Any suitable fabrication techniques may be used to pattern waveguide 6-416 and/or grating coupler 6-414. In some embodiments, a layer of material may be formed over bottom cladding 6-410 and a mask may be patterned over the layer such that the exposed regions of the layer may be selectively etched to form the desired pattern for waveguide 6-416 and grating coupler 6-414.

Layer of material 6-418 may be formed over waveguide 6-416, as shown in FIG. 5-3A, which may result in a top cladding layer of an integrated device. Layer 6-418 may be formed by growing a material and/or depositing the material to a desired thickness. Layer 6-418 may include any suitable dielectric material having a desired level of transparency to excitation energy and emission energy. Examples of suitable materials used to form layer 6-418 include silicon oxide, aluminum oxide, and titanium oxide. In some embodiments, the thickness, along the z-axis, of the layer formed over waveguide 6-416 shown in FIG. 5-3A may be in the range of 500 nm to 1200 nm, or any value or range of values within that range. In some embodiments, the thickness of layer 6-418 may be approximately 750 nm. Layer 6-418 may have variation in thickness by being formed over a patterned layer (e.g., grating coupler 6-414).

Layer 6-418 may be planarized to form a surface of a top cladding of an integrated device, as is shown in FIG. 5-3B. In some embodiments, the cladding may be planarized through a chemical mechanical planarization (CMP) process. The CMP process may reduce the surface roughness of the surface of the top cladding, which may reduce optical loss of excitation energy as it propagates along a waveguide proximate to the surface, such as waveguide 6-416. The thickness of layer 6-418 along the z-direction may be reduced as a result of the planarization process. In some embodiments, the thickness of the top cladding may be decreased by 350 nm. A thickness of the resulting top cladding may have a dimension along the z-direction in the range of 100 nm to 500 nm, or any value or range of values within that range.

Figures 3C, 5:
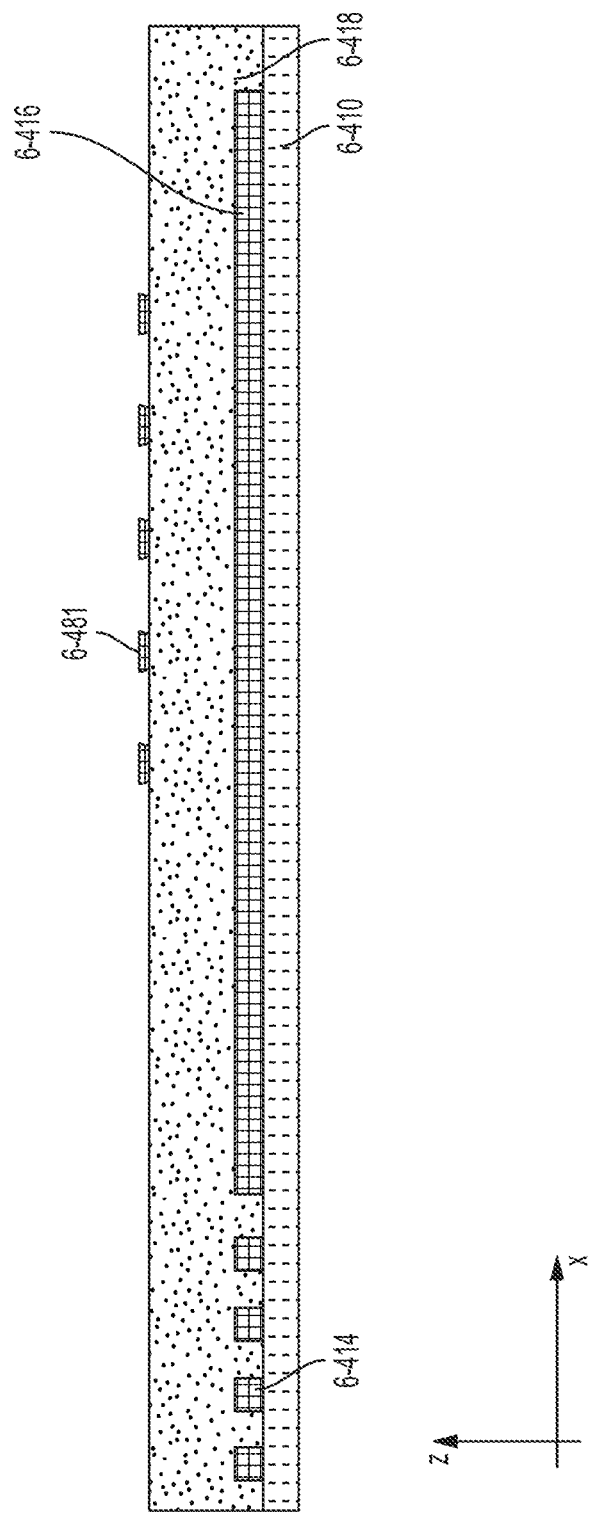

An etch stop layer 6-481 may be deposited on a surface of layer 6-418, as shown in FIG. 5-3C. The etch stop layer may be patterned to define regions corresponding to individual sample wells of the integrated device. In some embodiments, the etch stop layer may be selectively removed through a lithographic process in some regions while it may be maintained in the region where the sample wells are to be formed. Examples of suitable materials used to form etch stop layer 6-481 include SiN, SiON, $SiO_xN_y$, Al, Ti, and TiN. In some embodiments, etch stop layer 6-481 may include layered combinations of different materials. The thickness of etch stop layer 6-481 may have a dimension along the z-direction that may reduce the impact of the presence of the etch stop material proximate to waveguide 6-416 on optical loss of excitation energy. The thickness of etch stop layer 6-481 may be in the range of 20 nm to 200 nm, or any value or range of values within that range.

Figures 3D, 5:
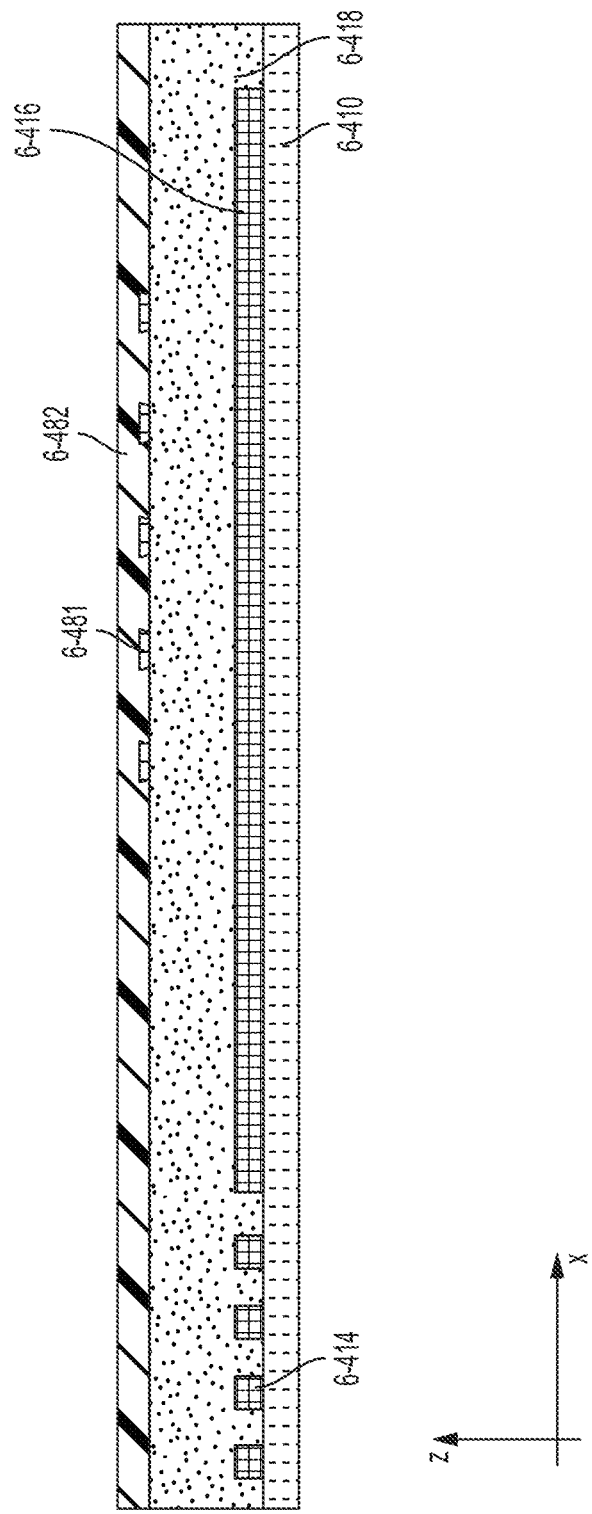

A dielectric layer 6-482 may be formed over etch stop layer 6-481 and/or layer 6-418, as shown in FIG. 5-3D. Dielectric layer 6-482 may be grown and/or deposited over etch stop layer 6-481 and/or layer 6-418. Examples of suitable materials used to form dielectric layer 6-482 include silicon oxide, aluminum oxide, and titanium oxide. In some embodiments, dielectric layer 6-482 may be deposited through a chemical vapor deposition (CVD) process. In some embodiments, dielectric layer 6-482 may be deposited through a high-density plasma chemical vapor deposition (HDPCVD) process.

Dielectric layer 6-482 may be planarized using any suitable fabrication techniques to form a surface. Dielectric layer 6-482 may be planarized through a chemical mechanical planarization (CMP) process. The resulting height of dielectric layer 6-482 may be in a range of 50 nm to 200 nm, or any value or range of values within that range. In some embodiments, the resulting height of dielectric layer 6-482 may be in a range of 95 nm to 100 nm, or any value or range of values within that range.

Figures 3E, 5:
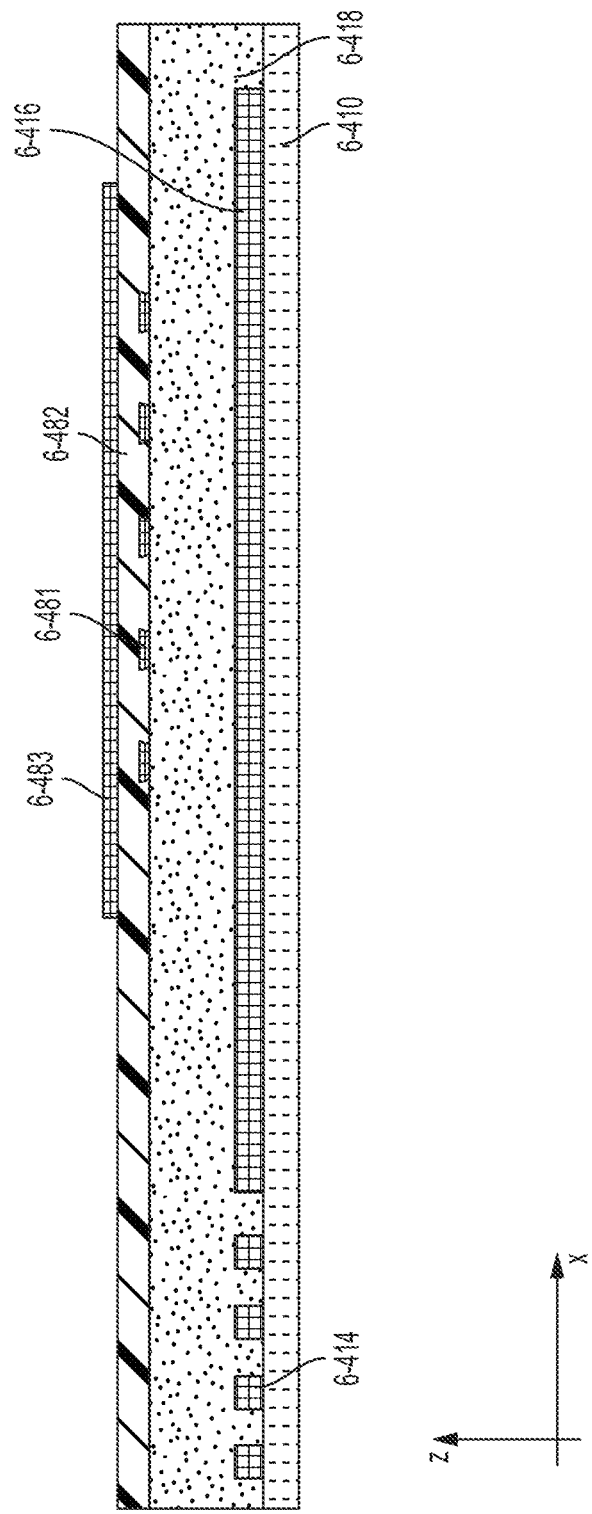

An etch stop layer 6-483 may be deposited on a surface of dielectric layer 6-482, as shown in FIG. 5-3E. The etch stop layer may be patterned to define regions corresponding to a trench region of the integrated device. The etch stop layer may be selectively removed through a lithographic process in some regions while it may be maintained in the region where a trench region is to be formed. Etch stop layer 6-483 may be maintained at least in a region overlapping with at least a portion of etch stop layer 6-481 along the z-axis. Examples of suitable materials used to form etch stop layer 6-483 include SiN, SiON, $SiO_xN_y$, Al, Ti, and TiN. In some embodiments, etch stop layer 6-483 may include layered combinations of multiple materials.

Figures 3F, 5:
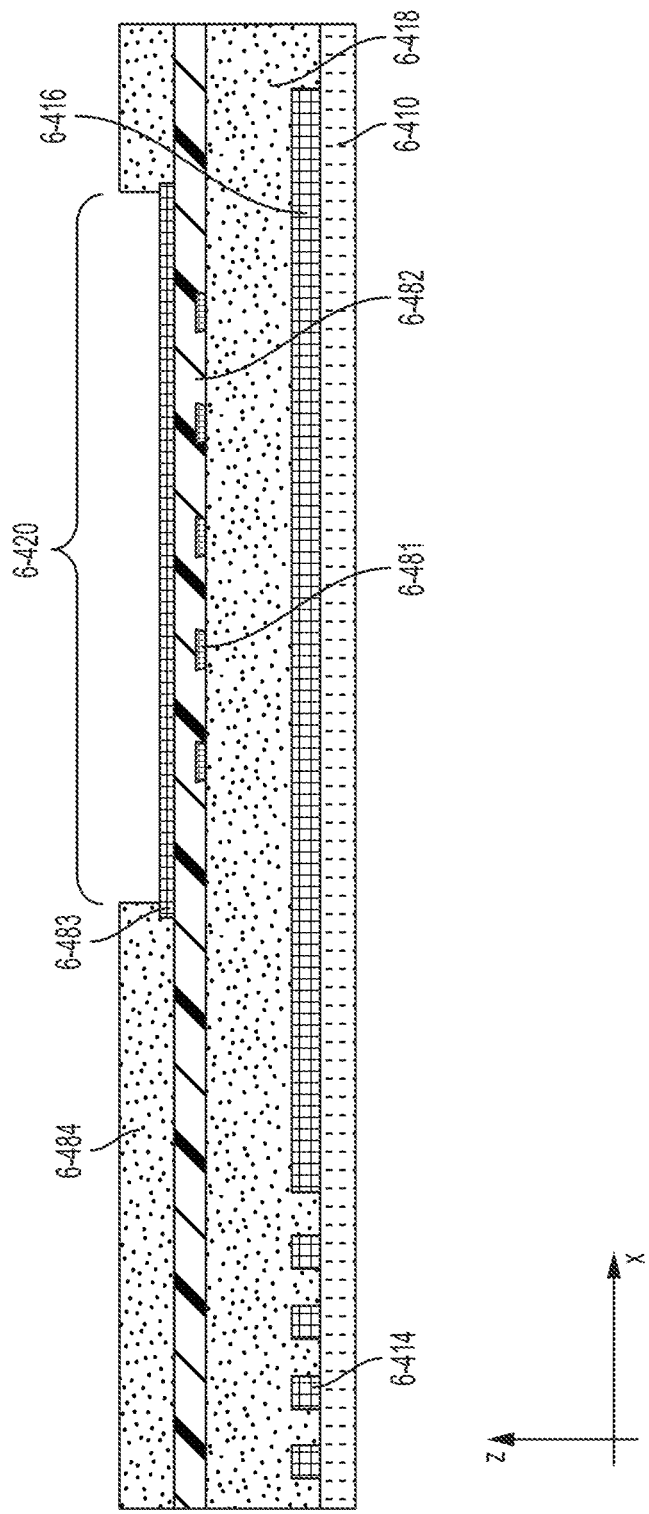

A dielectric layer 6-484 may be formed over etch stop layer 6-483 and/or layer 6-418, as shown in FIG. 5-3F. Dielectric layer 6-482 may be grown and/or deposited over etch stop layer 6-483 and/or layer 6-482. Examples of suitable materials used to form dielectric layer 6-483 include silicon oxide, aluminum oxide, and titanium oxide. In some embodiments, dielectric layer 6-483 may be deposited through a chemical vapor deposition (CVD) process. In some embodiments, dielectric layer 6-483 may be deposited through a high-density plasma chemical vapor deposition (HDPCVD) process.

Dielectric layer 6-484 may be selectively etched in a region that at least partially overlaps with etch stop layer 6-483. During etching, the presence of etch stop layer 6-483 may reduce etching beyond etch stop layer 6-483 and into layer 6-482. The etch process using etch stop layer 6-483 may provide formation of dielectric layer 6-484 having a desired dimension along the z-axis. Such a technique may improve the accuracy of the dimensions of layers within the integrated device without using of a time etching process as part of the fabrication process. Etch stop layer 6-483 may be removed using any suitable lithography techniques. The remaining portions of dielectric layer 6-484, layer 6-482, and layer 6-418 may act as a top cladding layer of an integrated device.

Figures 3G, 5:
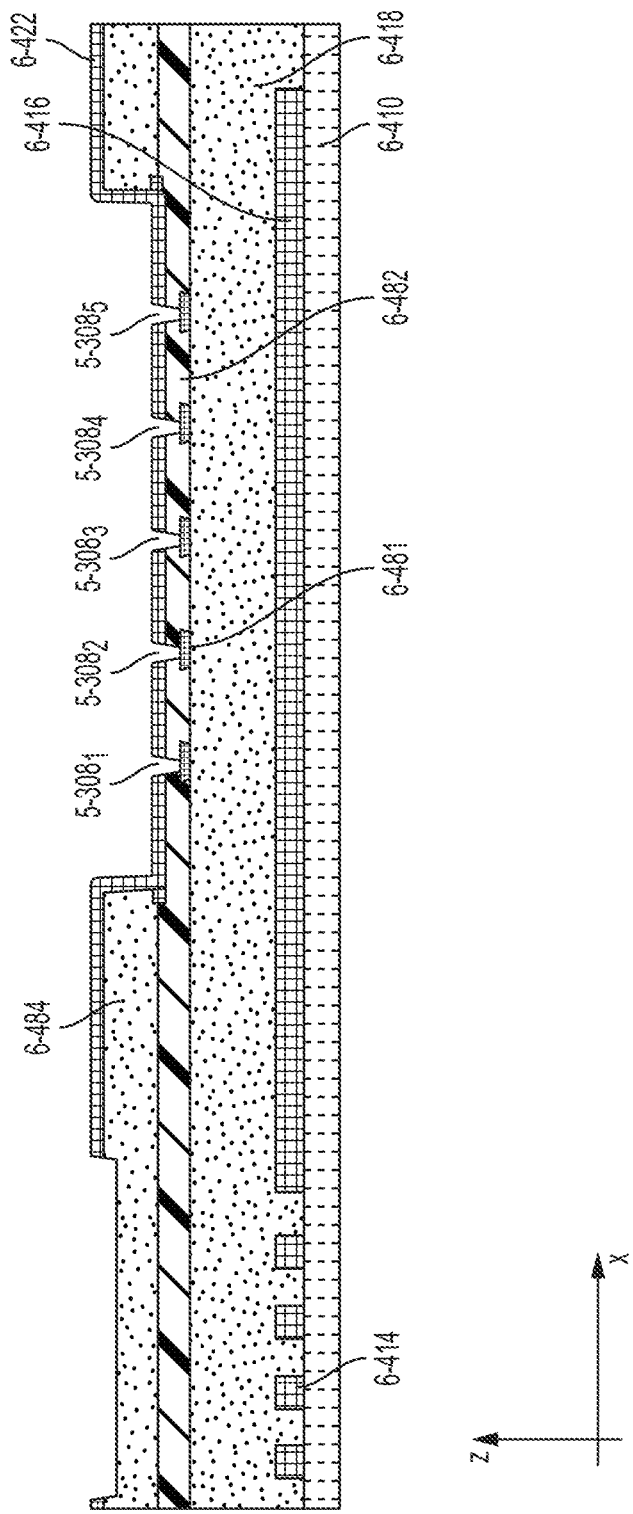

Metal layer 6-422 may be formed over dielectric layer 6-484 and/or on a surface of layer 6-482. As shown in FIG. 5-3G, metal layer 6-422 may be deposited on a surface of dielectric layer 6-484 and on the exposed surface of layer 6-482. Metal layer 6-422 may comprise aluminum, titanium, titanium nitride, or any suitable combination thereof. Sample wells 5-308₁, 5-308₂, 5-308₃, 5-308₄, and 5-308₅ may be formed by selectively removing regions of metal layer 6-422 and layer 6-482. While FIG. 5-3G illustrates five sample wells, the techniques of the present application are not limited in this respect and any suitable number of sample wells may be formed. Sample wells 5-308₁, 5-308₂, 5-308₃, 5-308₄, and 5-308₅ may be formed using a photolithographic process step by applying a photo-mask exposing the desired regions for formation of the sample wells and exposing the surface to selectively etch those regions. During etching, the presence of etch stop layer 6-481 may reduce etching beyond etch stop layer 6-481 and/or into layer 6-418. The etch process using etch stop layer 6-481 may provide formation of layer 6-482 having a desired dimension along the z-axis. The etching process may comprise a first etch through metal layer 6-422 and a second etch in layer 6-482. Excitation energy coupling region may be formed by removing a portion of metal layer 6-422, dielectric layer 6-484, and/or layer 6-482 that overlaps at least partially with grating coupler 6-114 along the z-axis.

In some embodiments, a sample well of an integrated device may be formed by forming a metal stack that includes at least one layer of a metal material on a top cladding and removing a portion of the metal stack and the top cladding. The metal stack may include a layer of aluminum positioned proximate to the top cladding. The aluminum layer may include copper and/or silicon. In some embodiments, aluminum layer may include less than approximately 2% of copper and/or silicon. The aluminum layer may have a thickness in the range of 30 nm to 150 nm, or any value or range of values within that range. In some embodiments, the aluminum layer is approximately 65 nm. In some embodiments, the metal stack may include a layer of titanium nitride over the aluminum layer. The titanium nitride layer may have a thickness of in the range of 1 nm to 50 nm, or any value or range of values within that range. In some embodiments, the thickness of titanium nitride layer is approximately 10 nm. In some embodiments, the metal stack may also include a layer of titanium over the aluminum layer. In embodiments where the metal stack includes a layer of titanium nitride, the layer of titanium may be positioned between an aluminum layer and the layer of titanium nitride. The titanium layer may have a thickness in the range of 1 nm to 50 nm, or any value or range of values within that range. In some embodiments, the thickness of the titanium layer is approximately 30 nm.

FIG. 6-1A, FIG. 6-1B, FIG. 6-1C, FIG. 6-1D and FIG. 6-1E illustrate steps for forming a sample well, according to some embodiments. As shown in FIG. 6-1A, metal stack 6-620 may be formed over top cladding layer 6-619, waveguide 6-616, bottom cladding layer 6-610, and substrate 6-600. Prior to forming the metal stack, a surface of top cladding layer 6-619 onto which the metal stack is to be formed may be planarized using a suitable process (e.g., a CMP process).

Metal stack 6-620 may include first sub-layer 6-622, second sub-layer 6-623, and/or third sub-layer 6-624. First sub-layer 6-622 may have a thickness in the range of 30 nm to 165 nm, or any value or range of values within that range. In some embodiments, the thickness of first sub-layer 6-622 may be approximately 65 nm. Second sub-layer 6-623 may have a thickness in the range of 1 nm to 50 nm, or any value or range of values within that range. In some embodiments, the thickness of second sub-layer 6-623 may be approximately 10 nm. Third sub-layer 6-624 may be in contact with second sub-layer 6-623. In embodiments of metal stack 6-620 that include only first sub-layer 6-622 and third sub-layer 6-624, third sub-layer 6-624 may be in contact with first sub-layer 6-622. Third sub-layer 6-624 may have a thickness in the range of 1 nm to 50 nm, or any value or range of values within that range. In some embodiments, third sub-layer 6-624 may have a thickness of approximately 30 nm. In some embodiments, first sub-layer 6-622 includes aluminum, second sub-layer 6-623 includes titanium, and third sub-layer 6-624 includes titanium nitride.

In some embodiments, metal stack 6-620 may be annealed to improve the stability of the materials included in metal stack 6-620 and may reduce the amount of corrosion that may occur. Metal stack 6-620 may be annealed at a temperature in the range of 300° C. to 500° C., or any temperature or range of temperatures within that range. In some embodiments, the substrate may be annealed at a temperature of approximately 400° C. Annealing of metal stack 6-620 may occur for a period of time in the range of 10 minutes to 60 minutes, or any time period within that range. In some embodiments, the stack may be annealed for approximately 40 minutes.

Photoresist layer 6-631 may be formed over metal stack 6-620, as shown in FIG. 6-1B. Photoresist layer 6-631 may be patterned to have one or more openings, which may correspond to a location of where a sample well is to be formed within metal stack 6-620. Photoresist layer 6-631 may act to protect material where the photoresist is present from an etching process while exposed material, such as through an opening, may be removed during the etching process. In some embodiments, photoresist layer 6-631 may include a positive photoresist. In some embodiments, photoresist layer 6-631 may include a negative photoresist. Anti-reflection coating layer 6-630 may be formed between photoresist layer 6-631 and metal stack 6-620. Photoresist 6-631 may be selectively etched following a photolithographic exposure so as to remove a region of the photoresist corresponding to the area where the sample well is to be formed.

Anti-reflection coating 6-630 may be selectively removed using a plasma etching process, or any suitable technique. Metal stack 6-622 may also be selectively removed using any suitable technique, including the sample process used to selectively remove anti-reflection coating 6-630. A cross-sectional area of the opening formed in metal stack 6-622 by removing a portion of metal stack 6-622 may form an aperture of the resulting sample well. In some embodiments, anti-reflection coating 6-630 and metal stack 6-622 may be removed through plasma etching process that includes $Cl_2$ and/or $BCl_2$. The plasma etching process may remove a portion of anti-reflection coating 6-630 and metal stack 6-622 that overlaps with an opening of photoresist layer 6-631.

Top cladding 6-619 may be selectively removed using a dry etching process, or any suitable technique, to form a cavity within top cladding 6-619 that overlaps with an opening of photoresist layer 6-631. In some embodiments, a dry etching process used to remove a portion of top cladding 6-619 may include the use of one or more fluorocarbon gases (e.g., $CF_4$, $CHF_3$, $C_4F_8$, $C_3H_2F_6$). In some embodiments, the dry etching process may occur for a duration of time to achieve a desired etch depth. In some embodiments, an etch stop layer may be positioned at a location within top cladding 6-619 to achieve a desired etch depth using the dry etching process. In some embodiments, one or more sidewalls of the cavity formed by the etching process may be at an angle to the normal of a surface of the cavity parallel or approximately parallel to waveguide 6-616. A sidewall of the cavity may be at an angle in the range of 1° to 15°, or any value within that range, from a normal to surface of the cavity parallel or approximately parallel to waveguide 6-616. In some embodiments, a sidewall of the resulting cavity may be approximately vertical to a surface of the cavity parallel or approximately parallel to waveguide 6-616. The cavity that results from the removal of metal stack 6-620 and top cladding 6-619 may form a sample well.

Photoresist layer 6-631 and/or anti-reflection coating 6-630 may be removed from metal stack 6-622 using a plasma removal process (e.g., ashing, cleaning), or any suitable technique. In some embodiments, photoresist layer 6-631 and/or anti-reflection coating 6-630 may be removed using an oxygen plasma removal process. In some embodiments, photoresist layer 6-631 and anti-reflection coating 6-630 are removed after etching of metal stack 6-622 and prior to etching of top cladding 6-619. In such embodiments, the opening in metal stack 6-622 that may form an aperture of the resulting sample well may be used as a mask (e.g., hard mask) for the removal process of top cladding 6-619. In some embodiments, photoresist layer 6-631 and anti-reflection coating 6-630 are removed after etching of metal stack 6-622 and top cladding 6-619.

Residues, including oxide and metal residues, may be removed using a wet solution, or any suitable process. In some embodiments, the resulting structure may be placed in a wet solution to reduce the presence of metal and/or oxide residues within the resulting sample well and/or on a surface of the resulting sample well. In some embodiments, the wet solution may comprise ACT 114 from Air Products.

A sidewall spacer may be formed on one or more surfaces of the resulting sample well. Examples of suitable materials used to form the sidewall spacer include $TiO_2$, TiN, TiON, TaN, $Ta_2O_5$, $ZrO_2$, and $HfO_2$. A sidewall spacer may have a thickness in the range of 3 nm to 30 nm, or any value or range of values within that range. In some embodiments, sidewall spacer 6-690 may have a thickness of approximately 10 nm.

As shown in FIG. 6-1D, spacer 6-690 may be deposited on metal stack 6-620 and one or more surfaces of the cavity formed in metal stack 6-620 and top cladding 6-619. Spacer 6-690 may be deposited through a suitable deposition process including atomic layer deposition (ALD), metal organic chemical vapor deposition (MOCVD), and ionized physical vapor deposition (IPVD). The deposition process may provide uniform or approximately uniform formation of material that forms sidewall spacer on an exposed surface of the structure.

Figures 1E, 6:
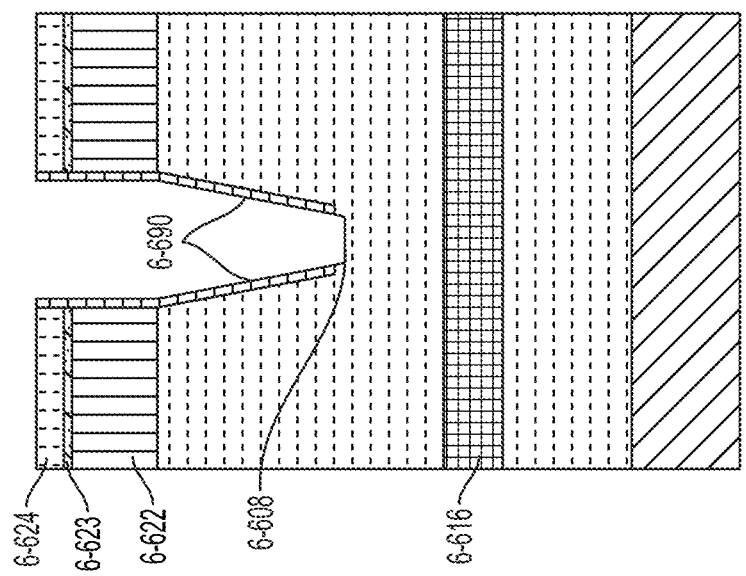
Figures 1B, 7:
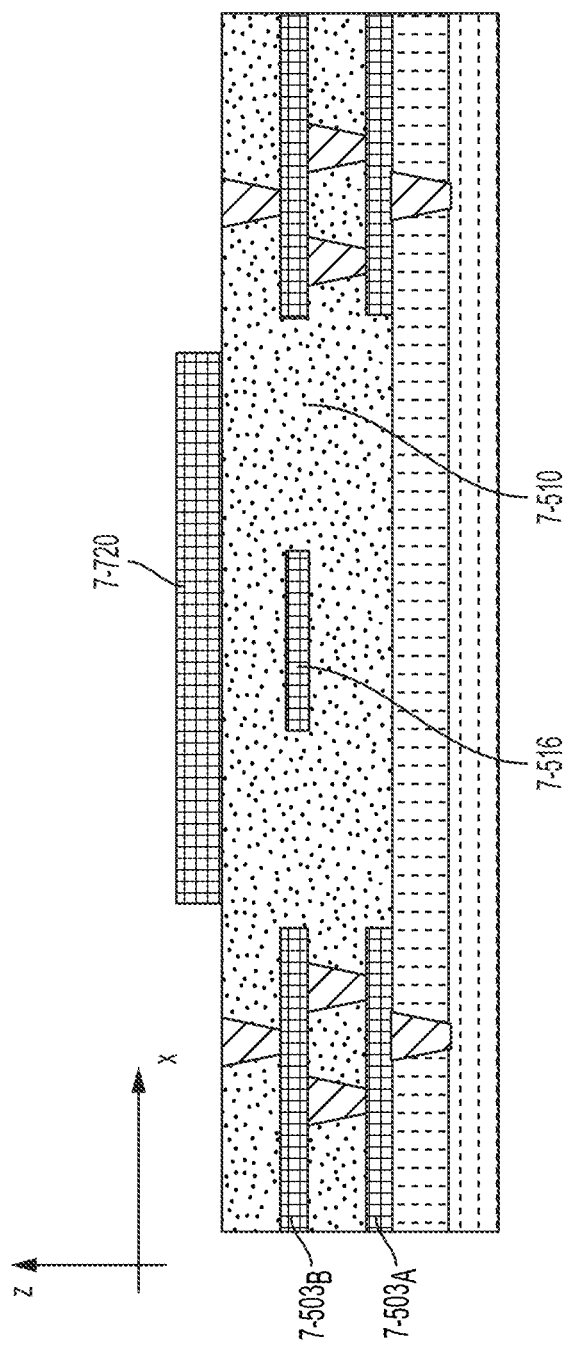
Figures 1C, 7:
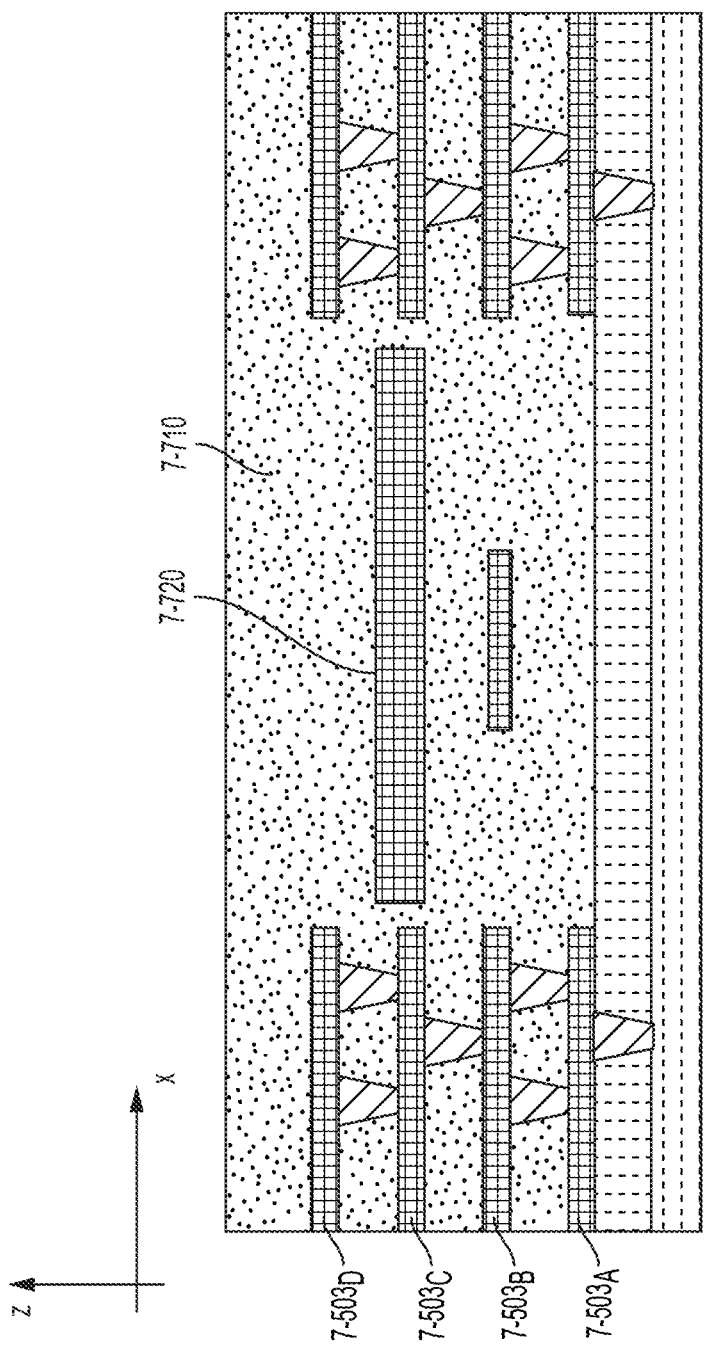
Figures 1D, 7:
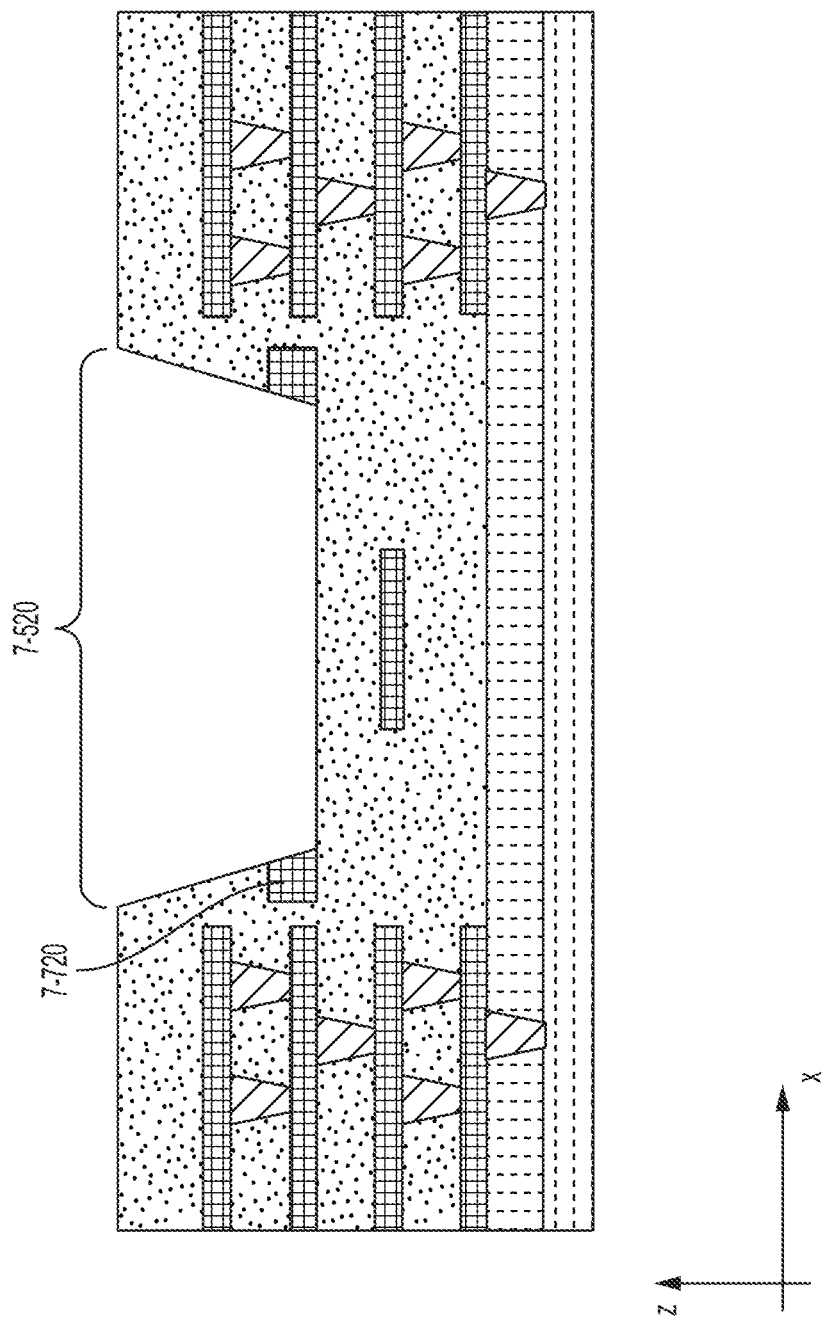
Figures 1E, 7:
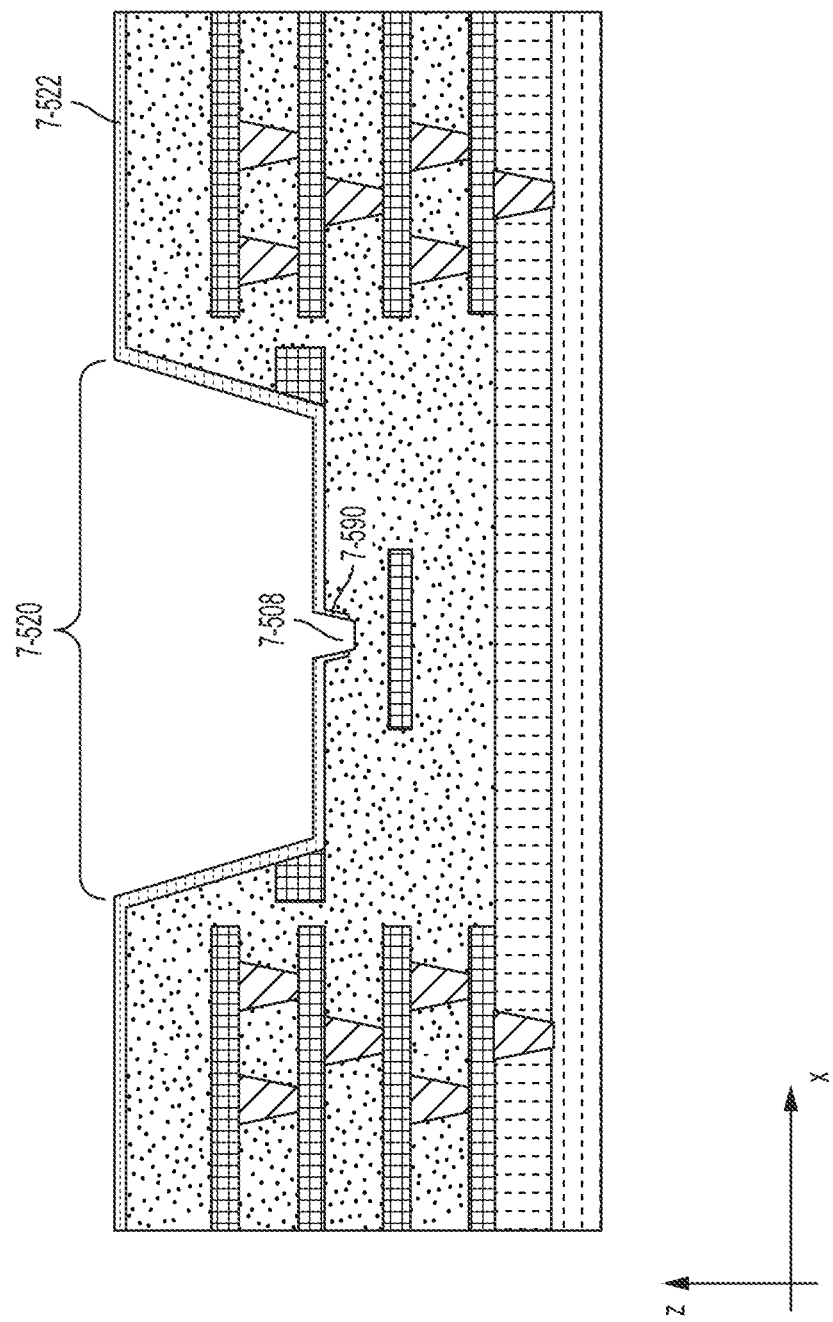
Figures 2A, 7:
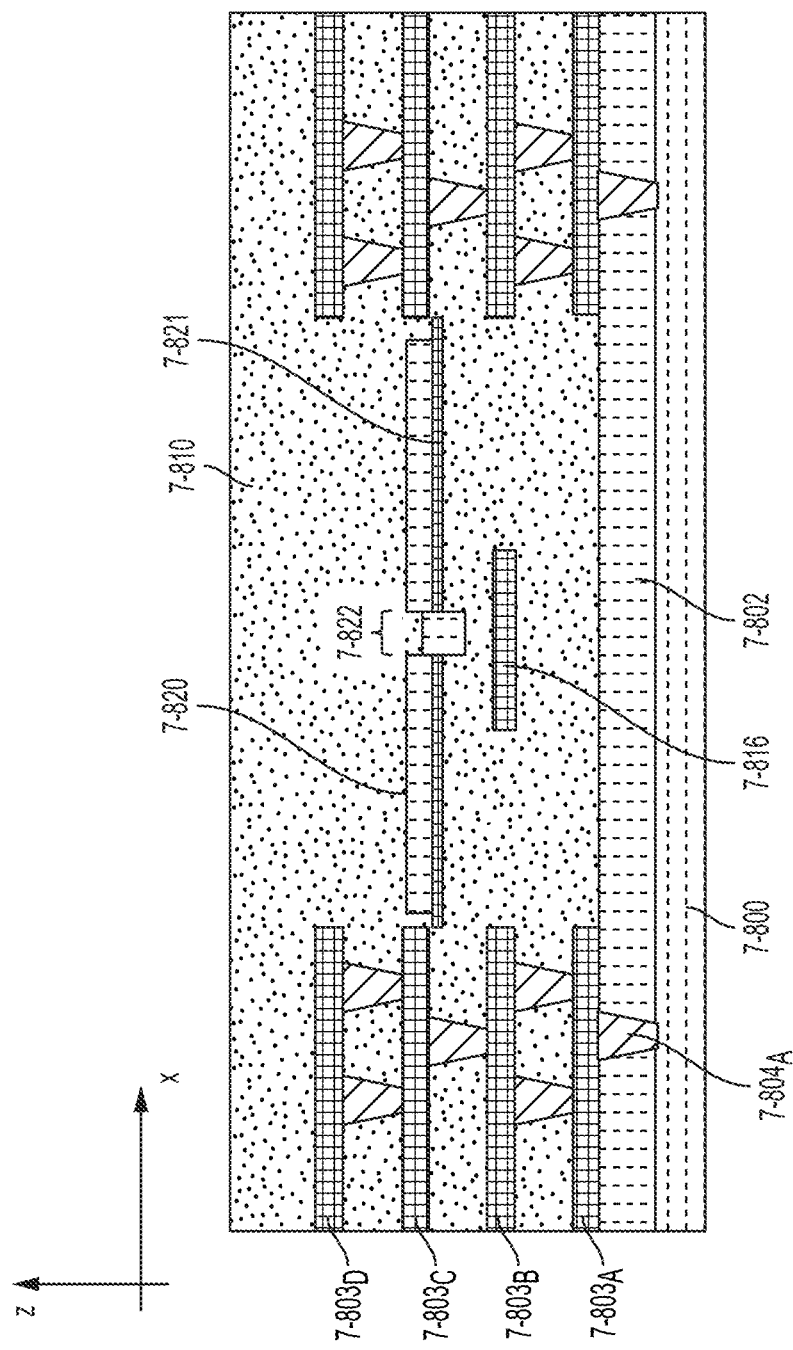
Figures 2B, 7:
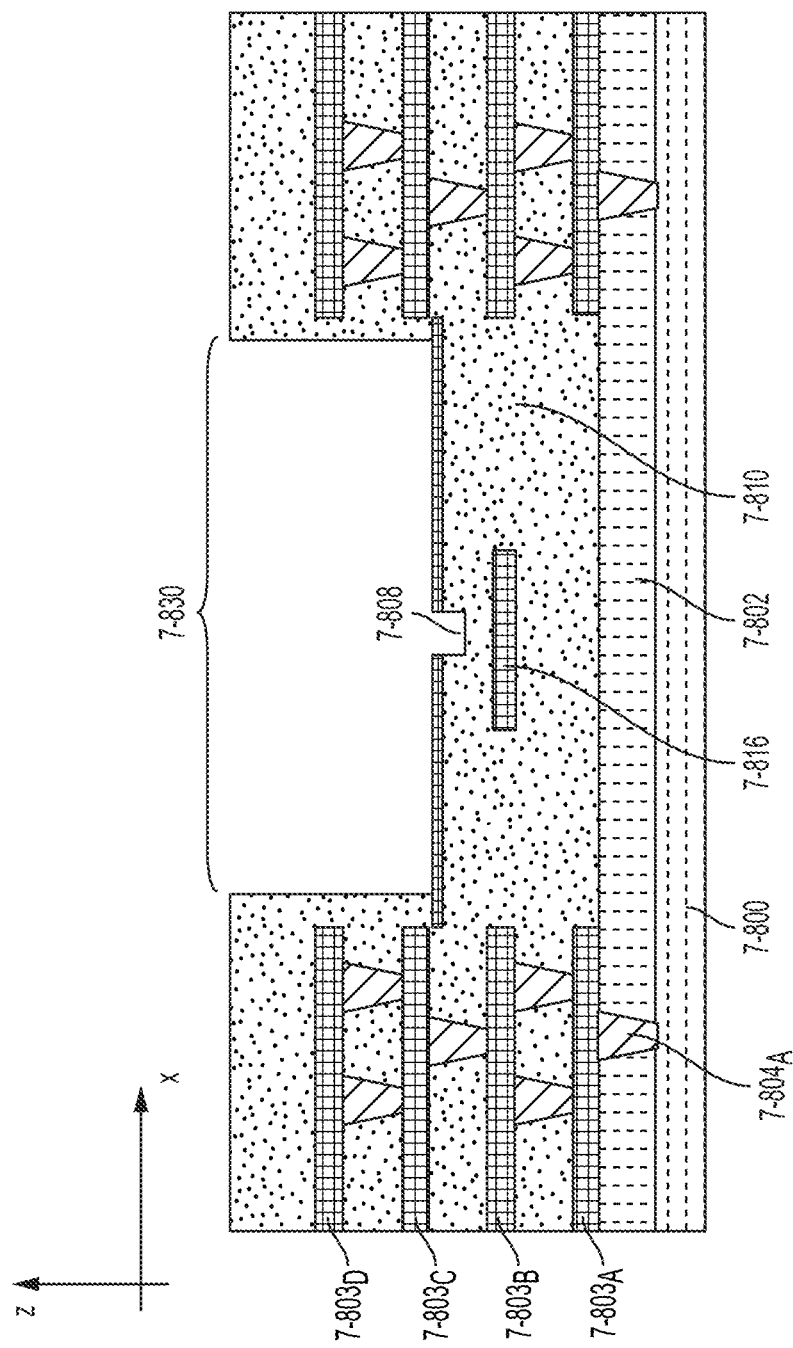

In some embodiments, the spacer material is removed from a surface of the sample well proximate to a waveguide. The surface may be approximately parallel to a direction of light propagation along the waveguide. As shown in FIG. 6-1E, the spacer material may be removed from the bottom surface 6-608 of the sample well. The sidewall spacer may be removed from the bottom surface of the sample well through an anisotropic etch process, which may remove material on horizontal surfaces (e.g., bottom surface of the sample well, surface of the metal stack). The anisotropic etch process may remove the sidewall spacer from the bottom surface while maintaining the sidewall spacer on at least a portion of the sidewalls of the sample well. The resulting structure may provide a different functionality for binding of a sample to the bottom surface 6-608 in comparison to the sidewalls of the sample well. Such functionality may allow a sample to preferentially adhere to bottom surface 6-608 over a sidewall of the sample well.

One or more openings through the integrated device may be formed to provide electrical contact to electrical circuitry within the device. An opening may provide access to one or more metal pads electrically coupled to a sensor of the integrated device. An opening may be formed by using any suitable removal process, including a lithography process followed by an etching process. In some embodiments, one or more openings may be formed using a photolithographic process. The photolithographic process may include the use of an Mine photoresist for a wavelength of 365 nm. The photolithographic process may form photoluminescent residues, which may form artifacts during analysis of a sample by the resulting integrated device. Such photoluminescent residues may be removed or reduced by an anisotropic etch process. Accordingly, in some embodiments, one or more openings may be formed in the integrated device prior to removal of spacer material formed on a bottom surface of the sample well by an anisotropic etch process. Such fabrication techniques may reduce the number of steps used to form an integrated device.

In some embodiments, formation of a sample well may include removal of top cladding 6-619 to extend a bottom surface of the sample well closer to waveguide 6-619, which may improve coupling of excitation energy from waveguide 6-619 and reduce the impact of metal stack 6-622 on optical loss of excitation energy. The removal process may occur after formation a spacer material on one or more sidewalls of the sample well and may be considered an "over-etch" process and may remove a thickness of top cladding 6-619 in the range of 20 nm to 50 nm, or any value within that range. The resulting sample well structure may have a portion proximate to waveguide 6-616 that lacks spacer material on the sidewalls in addition to the bottom surface of the sample well, as shown in FIG. 6-1F. The distance between the bottom surface and sidewall spacer may be in the range of 20 nm to 50 nm, or any value or range of values within that range. In some embodiments, the over-etch process may use $CF_4$. The removal process may also reduce the presence of residues in the resulting sample well.

Some embodiments relate to methods of forming an integrated device where a sample well is positioned proximate to a sensor by forming the sample well within and/or below a plane of the integrated device that includes a metal layer configured to route electrical signals within the integrated device. In such embodiments, the distance between a surface of the sample well and the sensor may be in the range of 2 µm to 3 µm, or any value or range of values within that range. A waveguide configured to deliver excitation energy to the sample well may be formed between the sample well and sensor. The waveguide may be formed in a plane of the integrated device that overlaps and/or is positioned below a plane includes a metal layer that may act as an electrical route for the integrated device. In this manner, waveguide may be considered to be embedded within the back-end-of-line (BEOL) wiring of the integrated device.

FIG. 7-1A, FIG. 7-1B, FIG. 7-1C, FIG. 7-1D and FIG. 7-1E illustrate steps of forming an integrated device where a waveguide and a sample well are embedded within the BEOL of the integrated device. Waveguide 7-516 may be formed over substrate 7-500 with one or more layers of a cladding material in between waveguide 7-516 and substrate 7-500. A distance between waveguide 7-516 and substrate 7-500 may be in the range of 1 µm to 2 µm, or any value or range of values within that range. In some embodiments, the distance between waveguide 7-516 and substrate 7-500 may be in the range of 1.2 µm to 1.7 µm, or any value or range of values within that range.

Figures 4, 5, 6, 7, 7C:
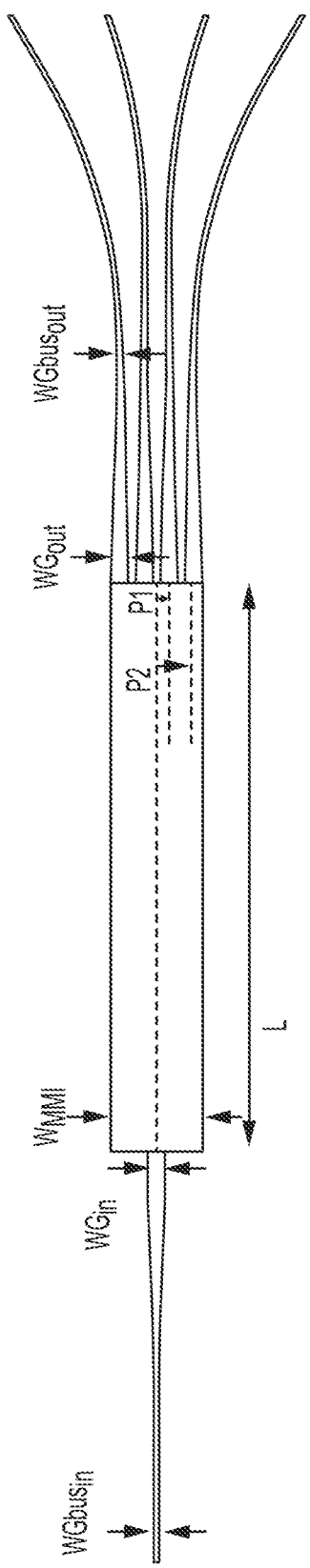
Figures 4, 5, 6, 7, 8, 9, 9B:
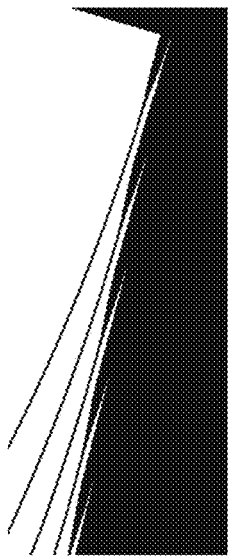
Figures 4, 5, 6, 7, 8, 9, 9A:
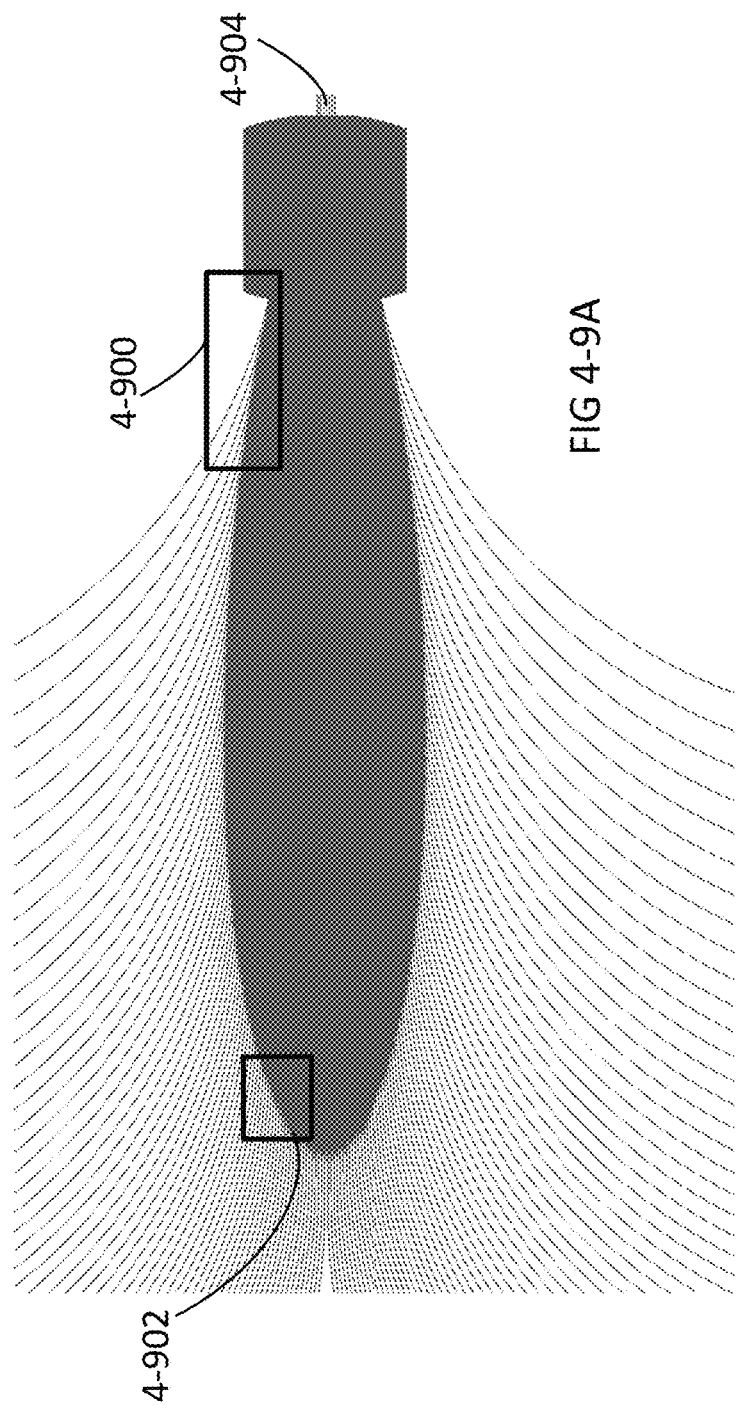
Figures 4, 5, 6, 7, 8, 9, 9C:
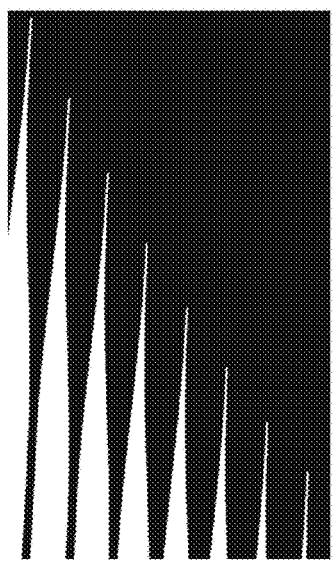
Figures 4, 5, 6, 7, 8, 9, 10:
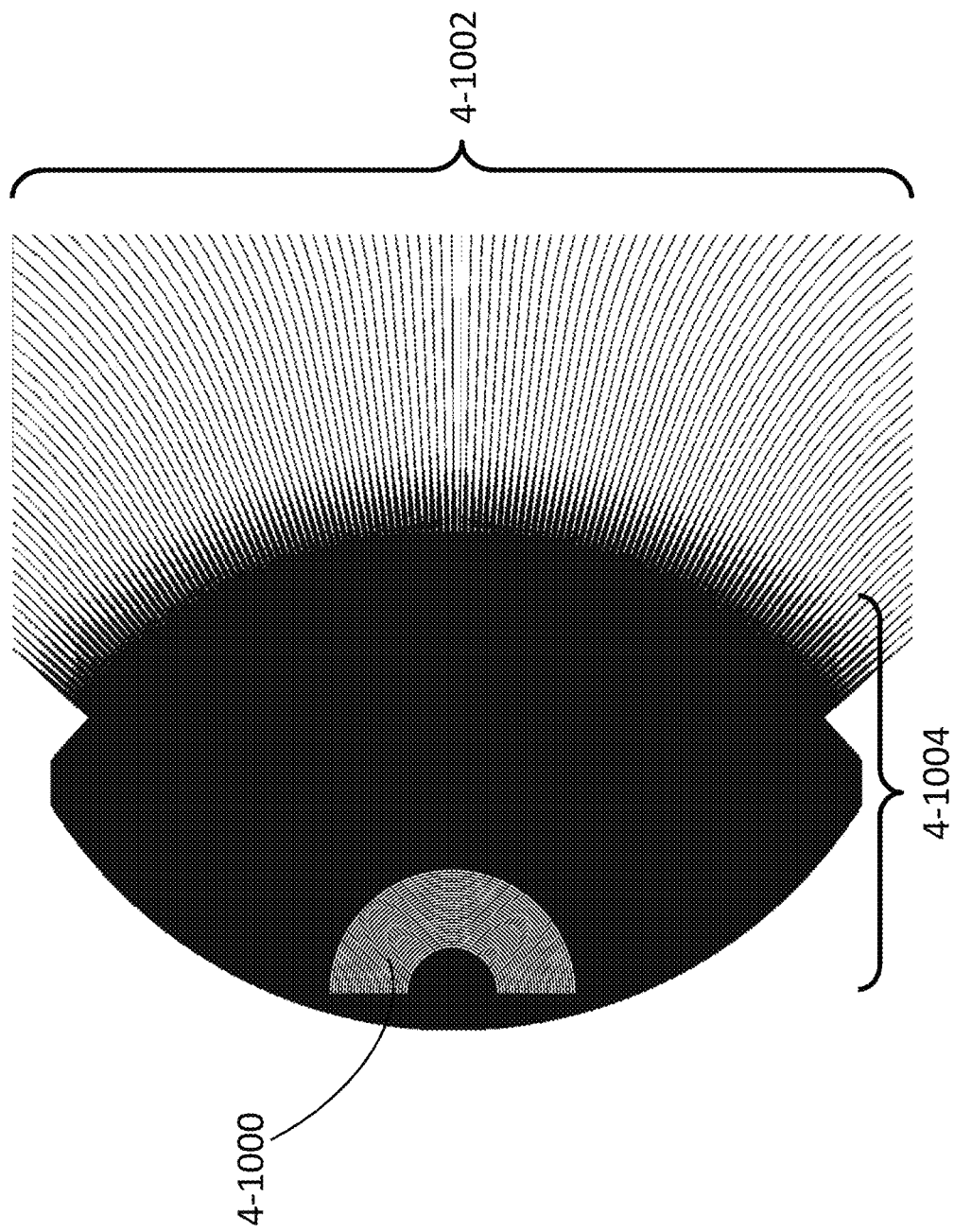
Figures 4, 5, 6, 7, 8, 9, 10, 11:
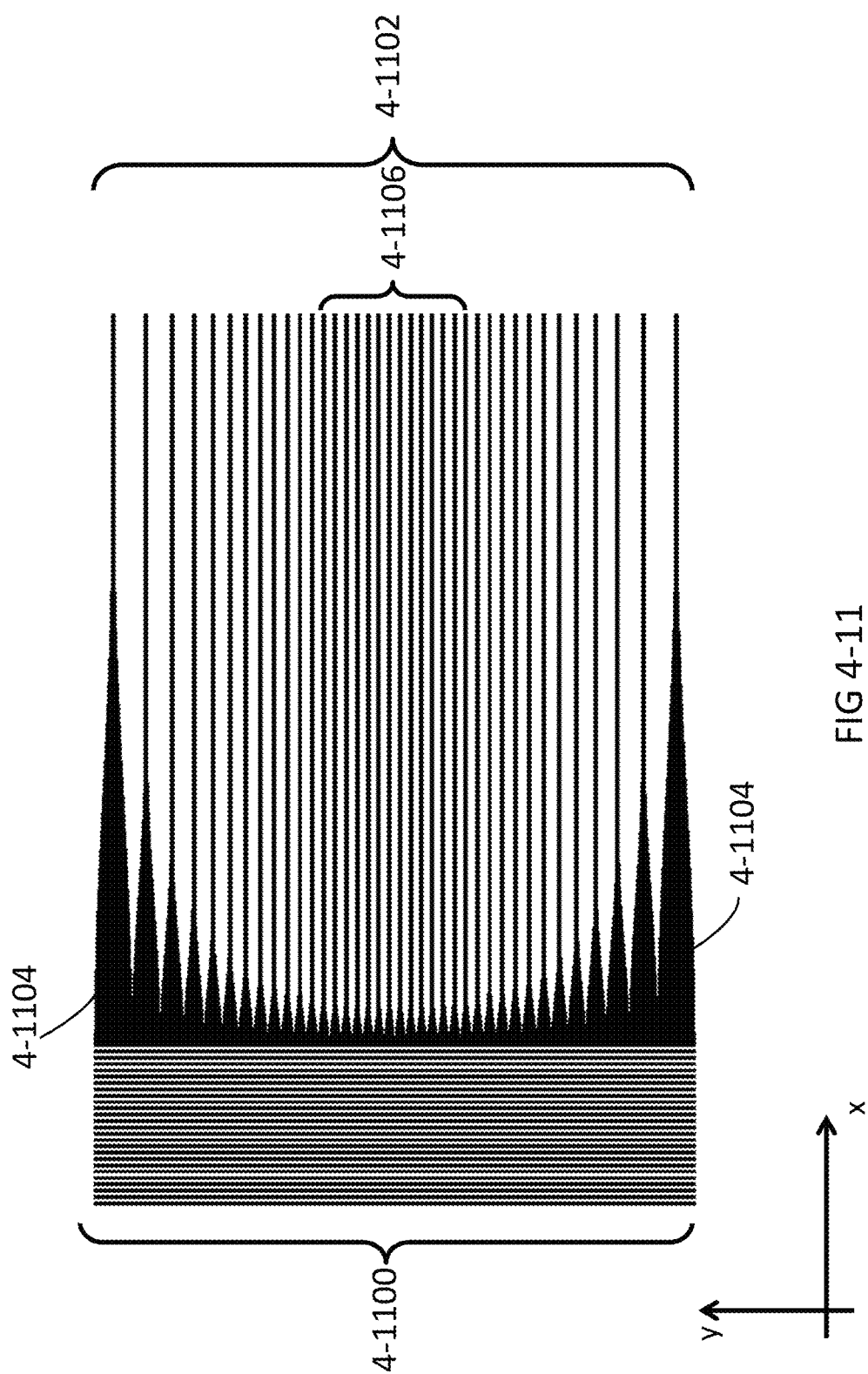

As shown in FIG. 7-1A, dielectric layer 7-502 and cladding layer 7-510 may be formed on substrate 7-500 with metal layer 7-503$_A$ between dielectric layer 7-502 and cladding layer 7-510. Dielectric layer 7-502 and/or cladding layer 7-510 may be formed by growing or depositing (e.g., plasma-enhanced chemical vapor deposition (PECVD), high density plasma chemical vapor deposition (HDPCVD)) a suitable material (e.g., dielectric material). Dielectric layer 7-502 may include undoped silicon dioxide. Examples of suitable materials used to form cladding layer 7-510 include silicon oxide, aluminum oxide, and titanium oxide. Via 7-504$_A$ may be formed through dielectric layer 7-502, such as by etching a portion of dielectric layer 7-502 to expose substrate 7-500 and filling the opening with a metal (e.g., tungsten).

Waveguide 7-516 may be formed over cladding layer 7-510, and additional cladding may be formed over waveguide 7-516. As shown in FIG. 7-1B, one or more metal layers 7-503 and vias 7-504 may be formed within the cladding layer. Etch stop layer 7-720 may be formed over cladding 7-510 at a desired distance from waveguide 7-516. Etch stop layer 7-720 may include silicon oxynitride (e.g., SiON). In some embodiments, a distance along the z-direction between etch stop layer 7-720 and waveguide 7-516 may be in the range of 2 µm to 3 µm, or any value or range of values within that range. Additional cladding 7-710 may be formed over etch stop layer 7-720, as shown in FIG. 7-1C. One or more metal layers 7-503 and vias 7-504 may be formed in an xy-plane over an xy-plane of etch stop layer 7-720.

One or more metal layers 7-503 may be electrically connected to substrate 7-500 through one or more vias 7-504. A value of a dimension along the z-dimension of a metal layer may be in the range of 450 nm to 650 nm, or any value or range of values within that range. In some embodiments, a dimension of a metal layer along the z-dimension is approximately 555 nm. A distance separating adjacent metal layers, such as metal layers 7-503$_A$ and 7-503$_B$ along the z-dimension may be in the range of 750 nm to 950 nm, or any value or range of values within that range. In some embodiments, a dimension of cladding 7-710 along the z-dimension between adjacent metal layers may be approximately 850 nm.

As shown in FIG. 7-1D, trench region 7-520 may be formed by removing a portion of cladding 7-710. The removed portion of cladding 7-710 may extend to etch stop layer 7-720. In some embodiments, the process used to remove cladding 7-710 may also be used to remove at least a portion of etch stop layer 7-720. Trench region 7-520 may be formed by etching cladding 7-710 until etch stop layer 7-720 is exposed. Etch stop layer 7-720 may improve the accuracy in achieving the desired depth of trench region 7-520.

As shown in FIG. 7-1E, metal layer 7-522 may be formed over trench region 7-520. Metal layer 7-522 may be formed using techniques described herein. Sample well 7-508 may be formed as a cavity within metal layer 7-522 and cladding 7-710 using the techniques described herein. In some embodiments, one or more surfaces of sample well 7-508 may be coated with sidewall spacer 7-590 using the techniques described herein.

In some embodiments, formation of an integrated device may include embedding a metal layer and a waveguide within the BEOL of the integrated device by forming the metal layer and an etch stop layer over the metal layer, forming a cladding layer over the etch stop layer, and removing a portion of the cladding layer to create the metal layer as a surface of the integrated device. FIG. 7-2A and FIG. 7-2B illustrate steps of forming an integrated device where a waveguide and a sample well are embedded within the BEOL of the integrated device.

As shown in FIG. 7-2A, dielectric layer 7-802 and cladding layer 7-810 may be formed on substrate 7-800 with metal layers 7-803$_A$, 7-803$_B$, 7-803$_C$, and 7-803$_D$ disposed within dielectric layer 7-802 and/or cladding layer 7-810. Dielectric layer 7-802 and/or cladding layer 7-810 may be formed by growing or depositing (e.g., plasma-enhanced chemical vapor deposition (PECVD), high density plasma chemical vapor deposition (HDPCVD)) a dielectric material. In some embodiments, dielectric layer 7-802 may include undoped silicon dioxide. Examples of suitable materials used to form cladding layer 7-810 include silicon oxide, aluminum oxide, and titanium oxide. Vias, such as via 7-804$_A$, may be formed through dielectric layer 7-802, such as by etching a portion of dielectric layer 7-802 to expose substrate 7-800 and filling the opening with a metal (e.g., tungsten).

Waveguide 7-816 may be formed within cladding layer 7-810, and metal layer 7-821 may be formed over waveguide 7-816 with a region of cladding layer 7-810 between waveguide 7-816 and metal layer 7-821. Opening 7-822 may be formed within metal layer 7-821, which may correspond to a location of an aperture for a sample well in the resulting device. A portion of cladding layer 7-810 may also be removed from a region that overlaps with the opening 7-822. Opening 7-822 and the removed region of cladding layer 7-810 may form a sample well in the resulting integrated device. Sacrificial layer 7-820 may be formed over metal layer 7-821 and fill, at least partially, opening 7-822 of metal layer 7-821 and the removed portion of cladding layer 7-810. Sacrificial layer 7-820 may include silicon oxynitride (e.g., SiON), Ti, and/or TiN. In some embodiments, a distance along the z-direction between sacrificial layer 7-820 and waveguide 7-816 may be in the range of 2 μm to 3 μm, or any value or range of values within that range. Additional cladding 7-810 may be formed over etch stop layer 7-820.

One or more metal layers 7-803 and vias 7-804 may be formed in an xy-plane over an xy-plane of sacrificial layer 7-820. One or more metal layers 7-803 may be electrically connected to substrate 7-800 through one or more vias 7-804. A value of a dimension along the z-dimension of a metal layer may be in the range of 450 nm to 650 nm, or any value or range of values within that range. In some embodiments, a dimension of a metal layer along the z-dimension is approximately 555 nm. A distance separating adjacent metal layers, such as metal layers 7-803$_A$ and 7-803$_B$ along the z-dimension may be in the range of 750 nm to 950 nm, or any value or range of values within that range. In some embodiments, a dimension of cladding 7-810 along the z-dimension between adjacent metal layers may be approximately 850 nm.

As shown in FIG. 7-2B, trench region 7-830 and/or sample well 7-808 may be formed by removing a portion of cladding layer 7-810 to sacrificial layer 7-820 and at least a portion of sacrificial layer 7-820. In embodiments where sacrificial layer 7-820 includes Ti and/or TiN, sacrificial layer 7-820 may be removed to expose a portion of metal layer 7-821 and/or a portion of cladding layer 7-810 using peroxide containing wet chemistry. Trench region 7-830 may be formed by etching cladding 7-810 until the sacrificial etch stop layer is exposed. The sacrificial etch stop layer may then be etched through a second etching process, until metal layer 7-821 is exposed.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. An integrated device comprising:
   a surface of the integrated device having a trench region recessed from a portion of the surface;
   an array of sample wells disposed in the trench region and recessed from a bottom surface of the trench region, wherein a sample well of the array of sample wells is configured to receive a sample; and
   a waveguide configured to couple excitation energy to at least one sample well in the array and positioned at a first distance from the bottom surface of the trench region and at a second distance from the surface of the integrated device in a region separate from the trench region, wherein the first distance is smaller than the second distance.

2. The integrated device of claim 1, wherein the first distance is between 150 nm and 600 nm.

3. The integrated device of claim 1, wherein the second distance is between 250 nm and 2000 nm.

4. The integrated device of claim 1, wherein the sample well has a surface at a distance less than 300 nm from the waveguide.

5. The integrated device of claim 1, wherein the integrated device further comprises at least one grating coupler configured to receive excitation energy from an excitation source separate from the integrated device and to direct excitation energy to the waveguide.

6. The integrated device of claim 5, wherein the integrated device further comprises a reflector configured to reflect excitation energy towards the at least one grating coupler.

7. The integrated device of claim 5, wherein the integrated device further comprises a splitter structure configured to receive excitation energy from the at least one grating coupler and direct excitation energy to a plurality of waveguides.

8. The integrated device of claim 7, wherein the splitter structure includes at least one multi-mode interference splitter.

9. The integrated device of claim 7, wherein the splitter structure includes a star coupler.

10. The integrated device of claim 7, wherein the splitter structure includes a sliced grating coupler.

11. The integrated device of claim 1, wherein the waveguide has a tapered dimension in a direction perpendicular to a direction of light propagation along the waveguide such that the tapered dimension is larger at a location proximate to a grating coupler than at a distal location.

12. The integrated device of claim 1, wherein the sample well includes a sidewall spacer formed on at least a portion of a sidewall of the sample well.

13. The integrated device of claim 12, wherein a surface of the sample well proximate to the waveguide is configured to interact with the sample in a different manner than the sidewall spacer.

14. The integrated device of claim 1, wherein the integrated device further comprises a metal stack formed on the bottom surface of the trench region, such that the metal stack has an opening that overlaps with an aperture of a sample well of the array.

15. The integrated device of claim 14, wherein the metal stack includes an aluminum layer and a titanium nitride layer, and the aluminum layer is proximate to the waveguide.

16. The integrated device of claim 1, wherein the waveguide includes silicon nitride.

17. The integrated device of claim 1, the integrated device further comprises a sensor configured to receive emission energy emitted by the sample located in the sample well.

18. An integrated device comprising:
a substrate having circuitry;
a waveguide having a first side facing the substrate and a second side opposite the first side; and
a plurality of metal layers formed over the substrate and configured to support a plurality of electrical signals, wherein a first metal layer of the plurality of metal layers is positioned at a distance closer to the substrate than the first side of the waveguide, and wherein the waveguide is positioned at a distance closer to the substrate than a second metal layer of the plurality of metal layers.

19. The integrated device of claim 18, further comprising:
a surface of the integrated device having a trench region recessed from a portion of the surface of the integrated device; and
an array of sample wells, disposed in the trench region, wherein a sample well of the array of sample wells is configured to receive a sample; and
wherein the waveguide is positioned at a first distance from a bottom surface of the trench region and at a second distance from the surface of the integrated device in a region separate from the trench region, wherein the first distance is smaller than the second distance.

20. An integrated device comprising:
a substrate having circuitry;
a waveguide having a first side facing the substrate and a second side opposite the first side;
a plurality of metal layers formed over the substrate and configured to support a plurality of electrical signals, wherein a first metal layer of the plurality of metal layers is positioned at a distance closer to the substrate than the first side of the waveguide;
a surface of the integrated device having a trench region recessed from a portion of the surface of the integrated device; and
an array of sample wells, disposed in the trench region, wherein a sample well of the array of sample wells is configured to receive a sample; and
wherein the waveguide is positioned at a first distance from a bottom surface of the trench region and at a second distance from the surface of the integrated device in a region separate from the trench region, wherein the first distance is smaller than the second distance.

* * * * *